(12) United States Patent
Johnson et al.

(10) Patent No.: US 11,614,610 B2
(45) Date of Patent: *Mar. 28, 2023

(54) SYSTEMS, DEVICES, AND METHODS FOR IMAGE PROCESSING TO GENERATE AN IMAGE HAVING PREDICTIVE TAGGING

(71) Applicant: ALLEN INSTITUTE, Seattle, WA (US)

(72) Inventors: Gregory Johnson, Seattle, WA (US); Chawin Ounkomol, Seattle, WA (US); Forrest Collman, Seattle, WA (US); Sharmishtaa Seshamani, Shoreline, WA (US)

(73) Assignee: ALLEN INSTITUTE, Seattle, WA (US)

( * ) Notice: Subject to any disclaimer, the term of this patent is extended or adjusted under 35 U.S.C. 154(b) by 109 days.

This patent is subject to a terminal disclaimer.

(21) Appl. No.: 17/148,192

(22) Filed: Jan. 13, 2021

(65) Prior Publication Data

US 2021/0173188 A1 Jun. 10, 2021

Related U.S. Application Data

(62) Division of application No. 16/304,021, filed as application No. PCT/US2018/045840 on Aug. 8, 2018, now Pat. No. 10,935,773.

(Continued)

(51) Int. Cl.
*G02B 21/00* (2006.01)
*G06T 7/187* (2017.01)
(Continued)

(52) U.S. Cl.
CPC ......... *G02B 21/008* (2013.01); *G06N 3/0454* (2013.01); *G06N 3/08* (2013.01);
(Continued)

(58) Field of Classification Search
CPC ...... G02B 21/008; G06N 3/0454; G06N 3/08; G06N 20/20; G06T 7/11; G06T 7/174;
(Continued)

(56) References Cited

U.S. PATENT DOCUMENTS 8,379,962 B2 2/2013 Hoyt et al.
9,002,077 B2 4/2015 Hoyt et al.
(Continued)

FOREIGN PATENT DOCUMENTS

EP 2921990 A2 9/2015
WO 2004/042392 A1 5/2004
(Continued)

OTHER PUBLICATIONS

El-Gamal et al., "Current Trends in Medical Image Registration and Fusion," Egyptian Informatics Journal. 2016. 17: p. 99-124.
(Continued)

*Primary Examiner* — Diane D Mizrahi
(74) *Attorney, Agent, or Firm* — Medler Ferro Woodhouse & Mills

(57) ABSTRACT

A computing device, method, system, and instructions in a non-transitory computer-readable medium for performing image analysis on 3D microscopy images to predict localization and/or labeling of various structures or objects of interest, by predicting the location in such images at which a dye or other marker associated with such structures would appear. The computing device, method, and system receives sets of 3D images that include unlabeled images, such as transmitted light images or electron microscope images, and labeled images, such as images captured with fluorescence tagging. The computing device trains a statistical model to associate structures in the labeled images with the same structures in the unlabeled light images. The processor further applies the statistical model to a new unlabeled
(Continued)

image to generate a predictive labeled image that predicts the location of a structure of interest in the new image.

16 Claims, 37 Drawing Sheets

Related U.S. Application Data

(60) Provisional application No. 62/651,765, filed on Apr. 3, 2018, provisional application No. 62/647,456, filed on Mar. 23, 2018, provisional application No. 62/568,749, filed on Oct. 5, 2017, provisional application No. 62/560,043, filed on Sep. 18, 2017, provisional application No. 62/543,333, filed on Aug. 9, 2017.

(51) Int. Cl.
  *G06T 7/11* (2017.01)
  *G06T 7/174* (2017.01)
  *G06N 20/20* (2019.01)
  *G06N 3/04* (2023.01)
  *G06N 3/08* (2023.01)

(52) U.S. Cl.
  CPC ............. *G06N 20/20* (2019.01); *G06T 7/11* (2017.01); *G06T 7/174* (2017.01); *G06T 7/187* (2017.01); *G06T 2207/10061* (2013.01); *G06T 2207/10064* (2013.01); *G06T 2207/30024* (2013.01)

(58) Field of Classification Search
  CPC ........... G06T 7/187; G06T 2207/10061; G06T 2207/10064; G06T 2207/30024; G06T 2207/10016; G06T 2207/10056; G06T 2207/20081; G06T 2207/20084; G01N 2015/1006; G01N 2015/1488; G01N 15/1429; G01N 15/1475; G06V 10/25; G06V 10/50; G06V 20/695; G06V 20/698; G06K 9/627; A61B 5/0275
  See application file for complete search history.

(56) References Cited

U.S. PATENT DOCUMENTS

| | | | |
|---|---|---|---|
| 9,008,378 B2 | 4/2015 | Micheva et al. | |
| 9,625,387 B2 | 4/2017 | Demos et al. | |
| 9,770,172 B2 | 9/2017 | Sturm | |
| 9,786,050 B2 | 10/2017 | Bhargava | |
| 9,971,966 B2 | 5/2018 | Nelson et al. | |
| 10,935,773 B2 * | 3/2021 | Johnson | G06T 7/187 |
| 2007/0025606 A1 | 2/2007 | Gholap | |
| 2007/0109874 A1 | 5/2007 | Padfield et al. | |
| 2010/0183217 A1 | 7/2010 | Seung et al. | |
| 2012/0269417 A1 | 10/2012 | Bautista et al. | |
| 2013/0317369 A1 | 11/2013 | Bryant-Greenwood et al. | |
| 2014/0126801 A1 | 5/2014 | Callahan et al. | |
| 2014/0270457 A1 | 9/2014 | Bhargava | |
| 2018/0349770 A1 | 12/2018 | Nelson et al. | |
| 2020/0199555 A1 | 6/2020 | Zhang | |

FOREIGN PATENT DOCUMENTS

| | | |
|---|---|---|
| WO | 2010056409 A1 | 5/2010 |
| WO | 2017/087847 A1 | 5/2017 |
| WO | 2017146813 A1 | 8/2017 |

OTHER PUBLICATIONS

Lucas et al., "Bridging Microscopes: 3D Correlative Light and Scanning Electron Microscopy of Complex Biological Structures," Methods in Cell Biology. Elsevier Inc. 2012. 111: p. 325-356.

Myronenko et al., "Intensity-Based Image Registration by Minimizing Residual Complexity," IEEE Transactions on Medical Imaging. 2010. 29(11): p. 1882-1891.

Li et al., "Deep Learning Based Imaging Data Completion for Improved Brain Disease Diagnosis," Med. Image Comput. Assist Interv. 2014. 17(0 3): p. 305-312.

International Search Report and Written Opinion of the International Searching Authority dated Oct. 19, 2018, PCT Appl. No. PCT/US18/45840.

Any reference or information that is not included with this Information Disclosure Statement can be found in U.S. Appl. No. 16/304,021, to which this application claims priority.

Saya Katafuchi, Motohide Yoshimura "Corneal Endothelial Cell Recognition by CNN Based on Cell Region Features", 22th Symposium on Sensing via Image Information SSII 2016, Japan, Image Sensing Technology Study Group, Jun. 8, 2016, pp. 1-4.

Riku Sakuta, et al., "Vehicle License Number Estimation from Low-Resolution Image Using Convolutional Neural Network", Journal of The Institute of Electrical Engineers of Japan, Japan, The Institute of Electrical Engineers of Japan, Jun. 10, 2016, pp. 15-19.

Reasons for Refusal in corresponding Japanese Patent Application No. 2020-530428 dated Aug. 4, 2022.

\* cited by examiner

⇨ Conv 3 px, stride 1 → batch norm → ReLU
⇩ Conv 2 px, stride 2 → batch norm → ReLU
⇧ Transposed Conv 2 px, stride 2 → batch norm → ReLU
⇨ Concatenate Fluorescence image of a DNA model, showing condensation of chromatin just before and during mitosis

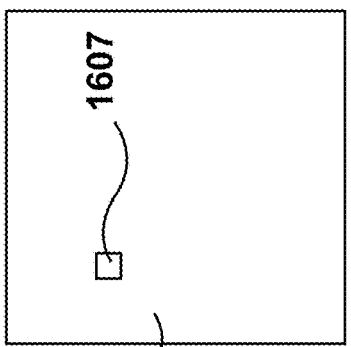
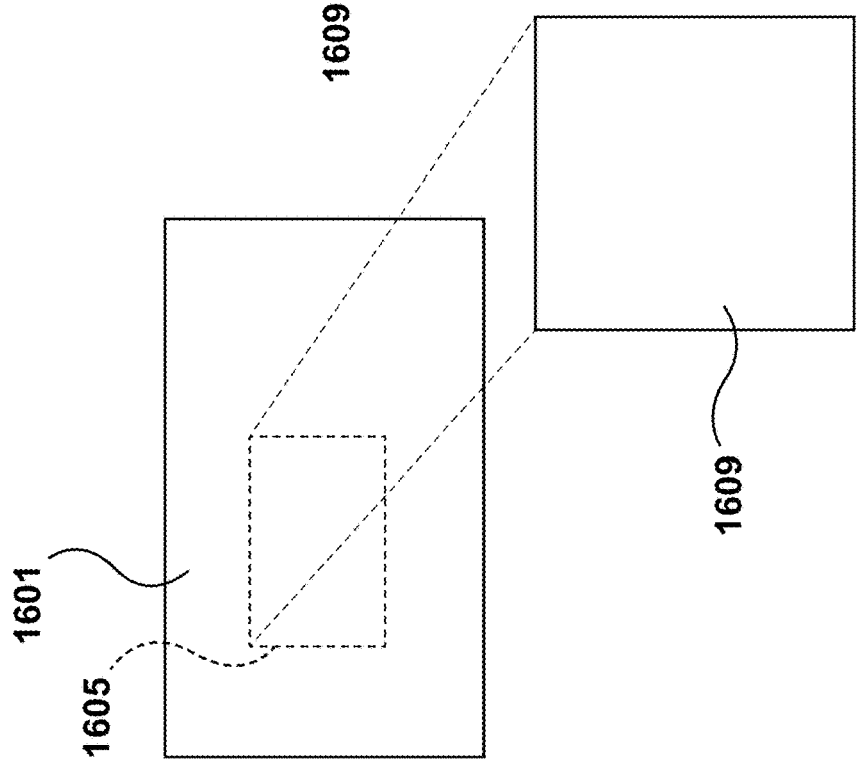
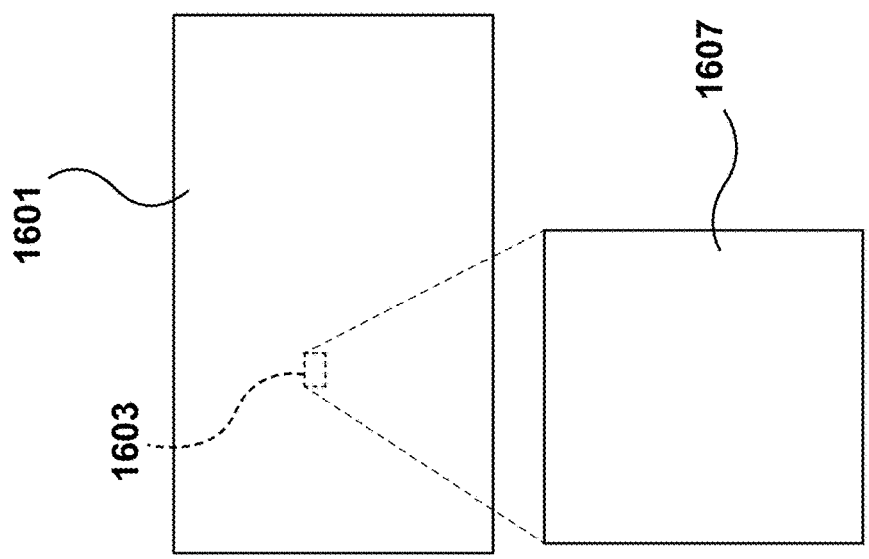
FIG. 16A
FIG. 16B
FIG. 16C

Receive a first pair of images, wherein the first pair of images include a first image that is a fluorescence image of one or more cellular structures, and include a second image that is an electron micrograph (EM) image of the one or more cellular structures, wherein the first image and the second image are registered with each other, such that they are aligned with each other and represent the same scale, or have associated registration information also received by the communication interface indicating how the first image and the second image can be aligned with each other 1611

Generate a statistical model to associate the one or more cellular structures in the first image with the one or more cellular structures in the second image 1613

Receive a second pair of images, wherein the second pair of images include a third image that is a fluorescence image, and a fourth image that is an electron microscope (EM) image, wherein the third image and the fourth image are both of the one or more cellular structures, or of another one or more cellular structures, and wherein the third image and the fourth image are not registered with each other 1615

Apply the statistical model to the fourth image generate an estimated fluorescence image of the fourth image 1616

Determine registration information between the estimated fluorescence image and the third image 1617

Register the third image and the fourth image with each other based on the registration information 1619

FIG. 16D

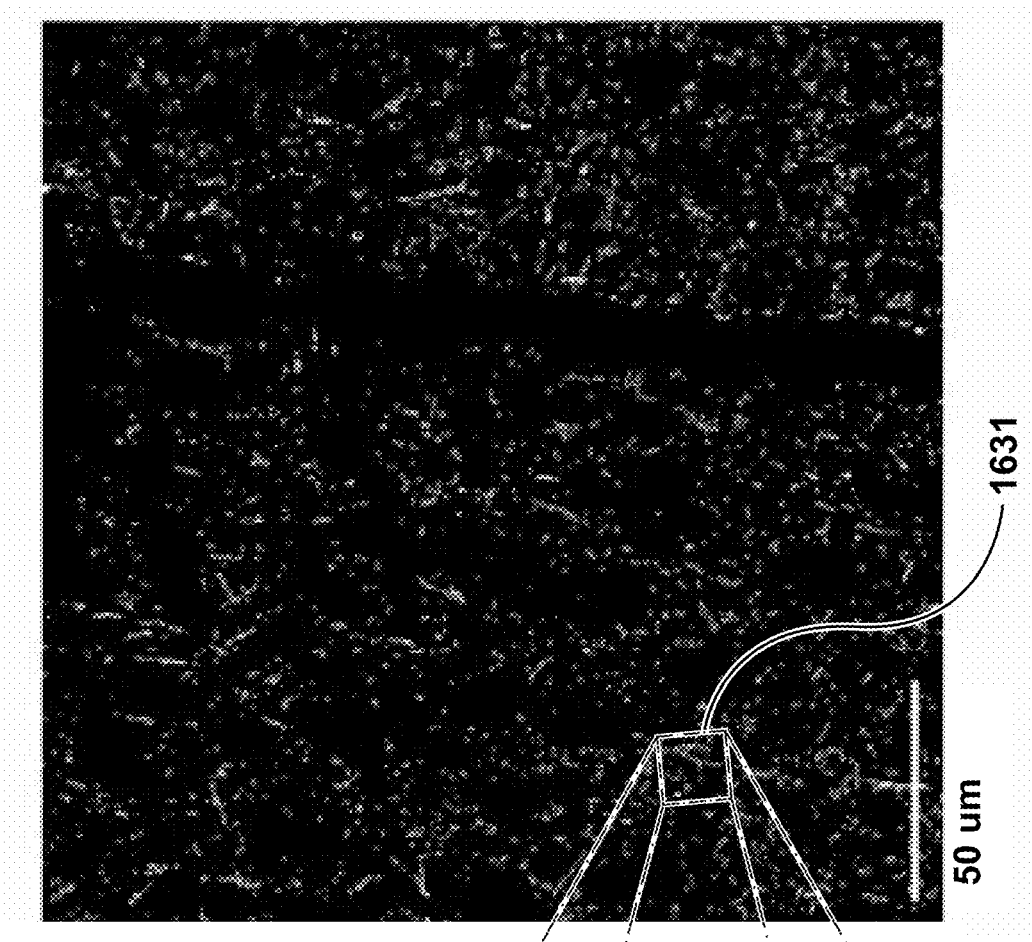
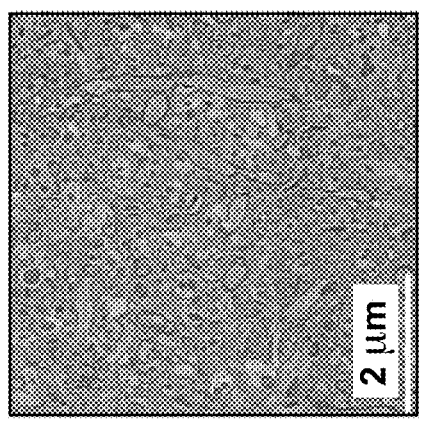
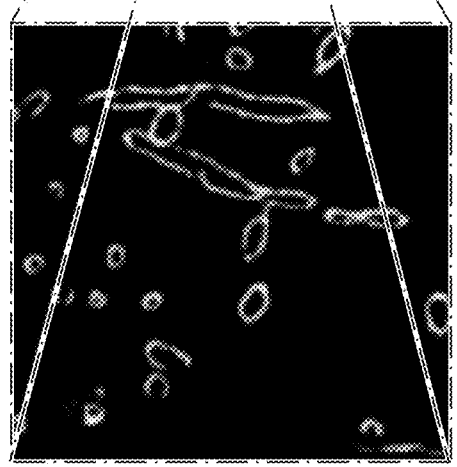
FIG. 16H
FIG. 16G

SYSTEMS, DEVICES, AND METHODS FOR IMAGE PROCESSING TO GENERATE AN IMAGE HAVING PREDICTIVE TAGGING

CROSS-REFERENCE TO RELATED APPLICATIONS

This application is a divisional of U.S. application Ser. No. 16/304,021, filed on Feb. 14, 2019, which is a National Stage of International Patent Application No. PCT/US2018/045840, filed on Aug. 8, 2018, which claims benefit of U.S. Provisional Application No. 62/543,333, filed on Aug. 9, 2017; U.S. Provisional Application No. 62/560,043, filed on Sep. 18, 2017; U.S. Provisional Application No. 62/568,749, filed on Oct. 5, 2017; U.S. Provisional Application No. 62/647,456, filed on Mar. 23, 2018; and U.S. Provisional Application No. 62/651,765, filed on Apr. 3, 2018. The disclosures of the above applications are incorporated herein by reference in their entirety.

STATEMENT REGARDING FEDERALLY-SPONSORED RESEARCH AND DEVELOPMENT

This invention was supported by grants from the National Institutes of Health, NIH/NINDS (R01NS092474) and NIH/NIMH (R01MH104227). As such, the government may have certain rights in the invention.

BACKGROUND

The methods, systems, and devices described herein relate to the visualization of intracellular objects in living or non-living (e.g., fixed specimens) cells, cell lines, or tissues that have not been exposed to labels, tags, or dyes for localization of those intracellular objects. Also provided are systems, devices, and methods for predicting the location of intracellular objects in unlabeled images using training data sets that include labeled, dyed, or tagged image stacks. Aspects disclosed herein can be further useful for predicting the spatiotemporal location of cellular objects over three dimensional (3D) stacks, or time-lapse stacks of imaging data without any labeling, based on statistical models generated by training with labeled 3D stacks or time-lapse stacks of imaging data.

Fluorescence microscopy is useful for identification of specific objects in imaging data. For example, fluorescence imaging can be used to identify and locate specific molecules or cellular structures in cells, cell lines, or tissue. The cellular structures may refer to sub-cellular structures (e.g., cell membrane, nucleus, or organelles), to cells, or to super-cellular structures. This is done by binding sub-cellular structures using structure-specific tags containing fluorescent proteins or chemical dyes and imaging using fluorescence microscopy.

However, sample preparation for fluorescent microscopy, which includes fluorescent labelling of the living tissue, is often time-consuming. Furthermore, the fluorescent labels can perturb the living tissue structure under study, such as by, for example, having a toxic effect or interference by the fluorescent tag. Chemical dyes, in contrast, often lack specificity, and also can be highly toxic. Additionally, the presence of fluorophores makes living tissue more susceptible to incident light used during fluorescence imaging (for example, when laser light is used for sample excitation), and the fluorophores tend to "bleach" due to repeated excitation, thus limiting light exposure, resolution, and imaging time for collecting image data. In contrast, bright-field images may contain substantial information about the structures of interest, are considerably more straightforward to acquire, and involve lower perturbation of the sample. It is thus desirable to combine the structure specific properties of fluorescence imaging that allow object identification, with the less invasive, ease-of-use properties of bright-field imaging.

The methods, systems, and devices described herein provide easily accessible, inexpensive visualization of intracellular objects (also referred to as sub-cellular objects) without expensive microscopes. Moreover, these methods, systems, and devices have the added benefit of greatly facilitating drug and toxicity screening and testing, assessments of cellular state, cellular differentiation, and activities in the fields of regenerative medicine and pharmaceutical drug selection and development.

Furthermore, three dimensional stacks of imaging data collected from living tissue integrate images from different structures into a composite image providing more thorough and complete information about the tissue. Additionally, using 3D stacks also can provide an internal metric for verifying accuracy of predictions, by having to account for contiguity of image properties.

SUMMARY

A method, system, or device includes a communication interface configured to receive multiple sets of 3-dimensional (3D) images. A first set of 3D images includes fluorescence images of a cellular or molecular structure, and a second set of 3D images includes transmitted light (bright field, phase contrast, differential interference, etc.) images of the cellular structure (e.g., sub-cellular structure). The device also includes a memory communicably coupled to the communication interface and configured to store the sets of 3D images. The memory is further configured to store computer executable instructions. The device also includes a processor communicably coupled to the memory and configured to execute the computer executable instructions to generate a statistical model to associate the cellular structure (e.g., sub-cellular structure) in the first set of 3D images with the cellular structure (e.g., sub-cellular structure) in the second set of 3D images. The processor is further configured to apply the statistical model to a third set of 3D images to estimate the location of the cellular structure (e.g., sub-cellular structure) in the third set of 3D images. The processor is further configured generate a fourth set of 3D images, the fourth set of 3D images including an indication of the estimated location of the cellular structure (e.g., sub-cellular structure) in the third set of 3D images. The method, system, or device can be used for visualizing intracellular objects in cells that have not been labelled, dyed, or tagged for the detection of the intracellular objects.

BRIEF DESCRIPTION OF THE FIGURES

FIGS. 16A-16K illustrate an example of a method for performing image registration by using a model prediction, according to an embodiment.

DETAILED DESCRIPTION

Figure 1A:
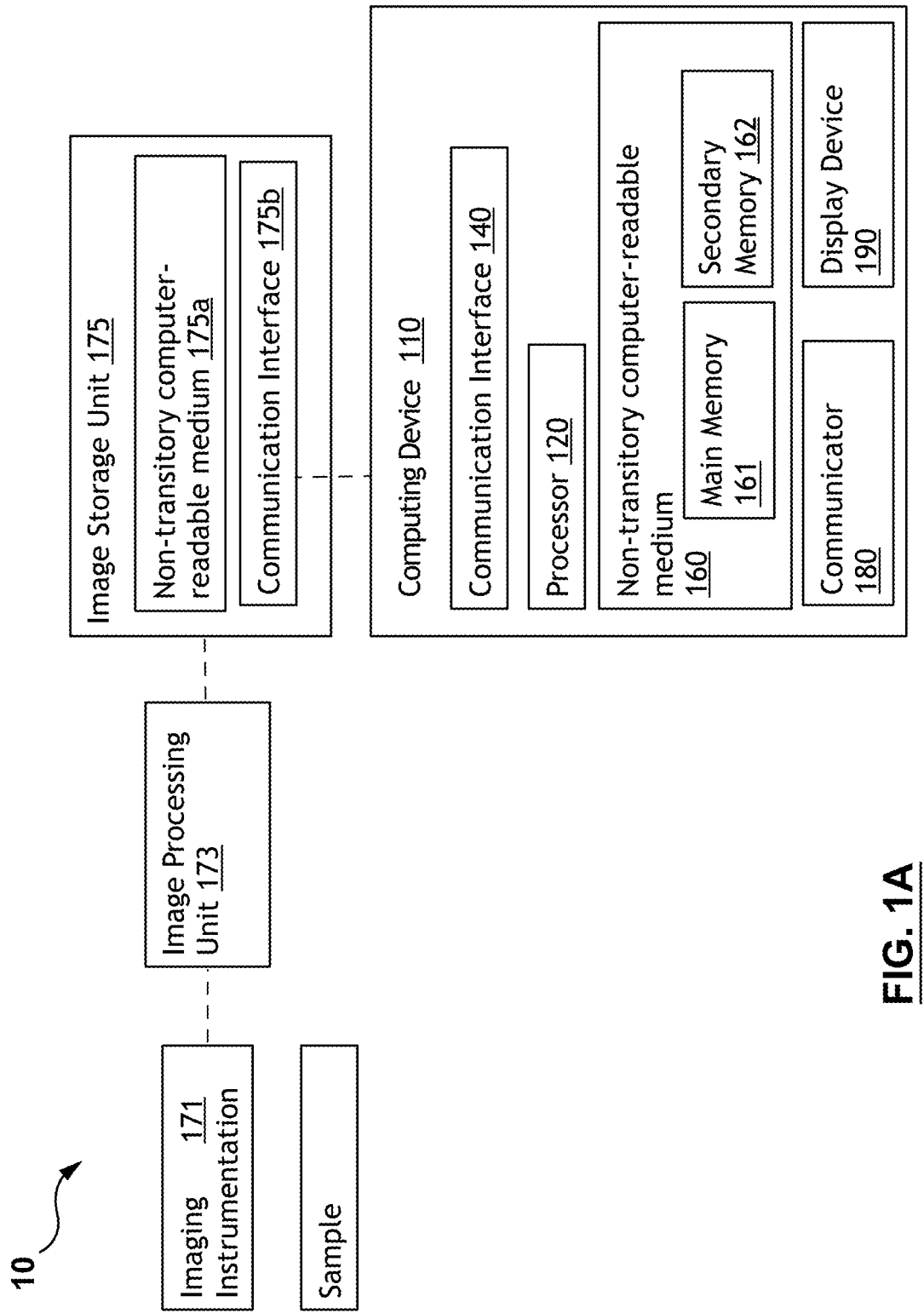
FIG. 1A is an illustrative example of a system for obtaining an image and for performing image analysis.

One aspect of the embodiments described herein relate to systems, devices, and methods for performing image analysis on microscopy images to predict localization of various structures or objects of interest, or more specifically to predict the location in such images at which a dye or other marker associated with such structures would appear. Because the appearance of the dye or other marker is used to visually label the structures or other objects of interest in an image, the result of the image analysis may be referred to as predictive labeling. The labeling may be predictive in that the dye or other marker is not actually applied to a sample that was imaged. Rather, the predictive labeling may predict (e.g., estimate or approximate) how the image would have been labeled by the dye or other marker (e.g., where the dye would appear) if the dye or other marker had been applied to the sample before the sample was imaged. In an embodiment, the image analysis may predict how image data in one imaging modality (e.g., transmitted light imaging) would appear if the image had instead been captured in another imaging modality (e.g., fluorescence imaging). The former imaging modality (e.g., transmitted light imaging) may omit the use of a fluorescence marker (the term fluorescence and fluorescent may be used interchangeably herein), wherein the fluorescence marker would have been used to tag various structures in an imaged sample, while the latter imaging modality may employ the use of a fluorescence marker to tag various structures in the imaged sample. The latter imaging modality (e.g., fluorescence imaging) may be referred to as a first imaging modality, while the former imaging modality (e.g., transmitted light imaging) may be referred to as a second imaging modality in this passage, though in other passages this nomenclature may be reversed. In some cases, the first imaging modality may use a dye or other marker to stain, tag, or otherwise label some structures being imaged, such as certain cells or sub-cellular structures in a tissue sample. In some cases, the tagging may use a dye or other marker that will selectively attach to or associate with a particular structure of interest. Stain from the marker may provide contrast between the structure of interest (e.g., cell nucleus) and the rest of the image, and thus may be used to visually label the structure in the image. Such a first imaging modality (e.g., fluorescence imaging) may have drawbacks, however, in terms of cost of the marker, complexity in applying the marker to a tissue sample, and/or damage that the dye (or other marker) may cause to the cell or other structures in the tissue sample being imaged. Meanwhile, the second imaging modality, such as transmitted light imaging, may produce images with less visual contrast between various sub-cellular structures or other features, making such structures harder to see for users. Examples of the transmitted light imaging include bright-field imaging, dark-field imaging, and differential interference contrast (DIC) imaging (which may also be referred to as bright-field microscopy, darkfield microscopy, and DIC microscopy). However, the second imaging modality may be less expensive, faster, and leave a tissue sample unperturbed. Thus, one aspect of the embodiments herein relate to obtaining a fast and inexpensive image using the second imaging modality, such as bright-field imaging, and predicting where a dye or other marker would appear in the image in order to visually label structures of interest as if the image had instead been obtained using the first imaging modality. The predictive labeling that is obtained may be sufficiently accurate to closely approximate the labeling that would have been obtained from actually tagging a sample with a marker. Thus, the predictive labeling may provide the benefits of the second imaging modality, which includes its low cost and minimal perturbation to an imaged sample, while substantially removing one of the drawbacks of the second imaging modality, namely that of low contrast between features.

The predictive labeling may have a variety of applications. In some aspects of the embodiments herein, the predictive labeling may be used to provide fast and efficient visualization of various sub-cellular structures (which are also referred to as intracellular structures), such as cell membranes, nucleus, organelles, and other structures. In some aspects of the embodiments herein, the predictive labeling may be used to assist in cell segmentation or to facilitate other aspects of performing cytometry. In some aspects of the embodiments herein, the predictive labeling may be used to assist in evaluating kinetics screening of drugs or other chemicals. In some aspects of the embodiments herein, the predictive labeling may be used to further facilitate automated image registration between different imaging modalities, such as between an electron microscopy (EM) imaging modality and a fluorescence imaging modality. Such image registration may be used to enhance conjugate array tomography, or may be used in other contexts.

In an embodiment, the predictive labeling may be done by examining a first image captured from a sample using the first imaging modality, and examining a second image captured from the sample using the second imaging modality, and determining a relationship between them. This relationship may be reflected in a statistical model that is trained to correlate images of the first imaging modality with images of the second imaging modality. In some implementations, the statistical model may be a convolutional neural network (CNN), and determining this relationship may involve training the CNN to convert an image type that includes the second imaging modality (e.g., brightfield images) to an image type that includes the first imaging modality (e.g., fluorescence images). The trained model can then be used to convert new images that were obtained using the second imaging modality into images that predict (e.g., approximate) how the structures in the new images would appear if they had instead been captured using the first imaging modality. The converted images may, for instance, display a region having high contrast with its surroundings, wherein the region represents a fluorescence marker tagging a structure of interest, or more directly represent the structure of interest.

In an embodiment, the predictive labeling may be applied on 3D images, which may be especially useful for structures smaller than the cellular level. Such structures, such as cell membranes, nucleus, and organelles, may be referred to as sub-cellular or intracellular structures. The 3D images may, for instance, be more suitable for training and yield a model that reflects a more accurate relationship between two imaging modalities. However, applying the predictive labeling to 3D images may be especially challenging because the 3D images may consume much more memory space relative to 2D images. In some instances, inexpensive, commodity computing hardware such as desktops, laptops, or a graphics processing unit (GPU) cluster may have a limited amount of main memory (e.g., dynamic RAM (DRAM)) that cannot accommodate all of the 3D images at the same time, and thus may be constrained in its ability to train a statistical model with the 3D images. Thus, one aspect of the embodiments herein relate to providing a technical solution that overcomes the technical limitations that some computing platforms may have in implementing the predictive labeling. For instance, the technical solution may involve storing the 3D images in secondary memory, such as a hard disk drive (HDD), and loading only a portion of the 3D images into the main memory at a time. The technical solution may further divide the training of the statistical model over several iterations. During each iteration, the computing platform may load a new portion of the 3D images from the secondary memory into main memory, and update the statistical model with the new portion of the 3D images. In some cases, the technical solution may involve downsampling the 3D images before they are used in training the statistical model. Thus, the solutions described herein overcome the particular and significant technical challenges involved in implementing predictive labeling for 3D images. While the statistical model described above is a convolutional neural network, other types of statistical models, including deterministic or stochastic models, may be used.

Aspects disclosed herein combine the benefits of detecting or visualizing specific cellular objects (which can include: intracellular structures, molecules, and foreign bodies, and super-cellular structures, for example groups of cells, networks of cells, regions of living tissue) with the ease and non-invasive nature of, e.g., bright-field imaging or other transmitted light imaging. Aspects disclosed herein are useful for visualizing the predictive localization of cellular structures by training statistical models using fluorescence images of one or more labeled structures of interest, (e.g., as a first set of 3D images of a plurality of sets of 3D images), to predict the labeling of those structures in three dimensional microscopy images without any structural labeling (e.g., as a second set of 3D images). In some cases, the trained model may be used to convert an image obtained using, e.g., bright-field imaging of a sample, into an image that approximates or otherwise predicts a fluorescence image of that sample. The first set of 3D images is labeled by a fluorescence marker or other chemical or biological marker, and thus may be referred to as labeled 3D images. The second set of 3D images is not labeled by any fluorescence marker or other chemical or biological markers, and thus may be referred to as unlabeled 3D images. The unlabeled imaging modality may include transmitted light imaging, such as bright-field microscopy, darkfield microscopy, differential interference contrast (DIC) imaging, and may also include Dodt microscopy, electron microscopy, radiography, array tomography, and/or the like. Thus, the methods, systems, and devices described herein relate to the visualization of intracellular objects in living cells or tissues that have not been exposed to labels, tags, or dyes for localization of those intracellular objects and provide easily accessible, inexpensive visualization of intracellular objects without expensive microscopes in facilitating drug and toxicity screening and testing, assessments of cellular state, cellular differentiation and segmentation, image registration, and activities in the fields of regenerative medicine and pharmaceutical drug selection/development.

The presented systems, devices, and/or methods, sometimes characterized as systems, devices and/or methods for three-dimensional image modality transfer or for predictive localization, can be characterized by quantifying the relationship between transmitted light images and the localization of dye and fluorescence-labeled nuclei and other intracellular objects. Aspects disclosed herein are further useful for accurately predicting, estimating, or otherwise identifying the spatiotemporal position of a variety of intracellular structures, such as cell membrane, plasma membrane, nucleus, mitochondria, endoplasmic reticulum, vacuole, Golgi Apparatus, lysosomes, nucleolus, DNA material, etc., from the bright-field light images in three dimensions. In an embodiment, the devices, methods, or systems herein may be used to identify structures of a cell during live cell imaging sessions, thus allowing users to visualize and quantify nuclei and other structures of interest without the addition of labels. Such a live cell imaging session may not be possible or may have only a very limited duration, such as a few minutes, if performed with a technique such as fluorescence imaging. The technique used by the devices, methods, or systems herein, on the other hand, can identify structures from images obtained using other imaging modalities, such as, for example, transmitted light microscopy, which can be used in live imaging sessions for a considerably longer amount of time, such as many hours or days. Thus, the devices, methods, or systems herein can facilitate an extended live cell imaging session to better allow a user to visualize movement or other changes in a cell over time.

In an embodiment, the systems, devices, and methods disclosed herein include the use of deep learning (deep structural learning, hierarchical learning, machine learning, and architecture) to predict the localization of cells or specific sub-cellular structures from three dimensional bright-field microscopy images or other transmitted light images. The deep learning can involve training using data collected though a labeled imaging method such as fluorescence microscopy of one or more cells or sub-cellular structures or molecules of interest. The disclosed systems, devices, and methods serve to transfer information (e.g., object or structure specific labeling) contained in a three dimensional stack of imaging data, in one imaging modality, to another imaging modality, thereby allowing using of the advantageous properties of both imaging modalities. The disclosed systems and methods can be characterized by quantifying the relationship between image stacks in each imaging modality. For example, an implementation of predictive localization of sub-cellular structures can be characterized by quantifying image information about specific structures predicted from transmitted light images and from the localization of dye and nuclei labelled with Green Fluorescent Protein (GFP). In example experiments, in some embodiments, the systems, devices and methods disclosed herein were used to generate statistical models based on training data set using bright field light images. The models were tested for performance on 3D time-lapse images obtained using bright-field imaging, and accurately predicted the spatiotemporal position of intracellular structures from the bright-field light images. As discussed above, in some embodiments, the systems, devices, and methods disclosed herein can be useful for extending live cell imaging sessions by allowing scientists to visualize and quantify nuclei and other desirable structures without fluorescent labels.

FIG. 1A illustrates a system 10 that facilitates the automated prediction of one type of image from another type of image. The latter type of image may include unlabeled images acquired using an imaging modality such as transmitted light imaging, while the former type of image may include labeled images acquired using an imaging modality, such as a fluorescence imaging, that uses a fluorescence marker to provide contrast or other visual labeling in an image. The system 10 includes imaging instrumentation 171 (e.g., a light microscopy microscope), an image processing unit 173, an image storage unit 175 (e.g., image server), and a computing device 110.

In an embodiment, the imaging instrumentation 171 (also referred to as an imaging instrument) may be configured to capture an image of a sample, such as a biological tissue sample. For instance, the imaging instrumentation 171 may be a transmitted light microscope that is configured to apply Kohler illumination to the sample and to capture an image resulting from the illumination. In an embodiment, the image processing unit 173 may operate with the imaging instrumentation 171 to perform any necessary image processing, and to store the image in a non-transitory computer-readable medium (e.g., memory 175a) of the image storage unit 175. In an embodiment, the image storage unit 175 may include a communication interface 175b, such as an I/O unit, for communicating an image to the computing device 110 via a direct interface (e.g., a USB connection), local area network (LAN), via the Internet, or in any other manner. In an embodiment, the system 10 may include the imaging instrumentation 171 as a first imaging instrumentation that is configured to capture, e.g., a transmitted light image of a sample, and may further include a second imaging instrumentation that is configured to capture, e.g., a fluorescence image of the sample.

In an embodiment, the computing device 110 includes a communication interface 140 for communicating with the image storage unit 175, and includes a processor 120, a non-transitory computer-readable medium 160 (e.g., memory), a communicator 180, and a display device 190. In an embodiment, the non-transitory computer-readable medium 160 may be configured to store both data, such as image data, and computer-executable instructions, such as computer code for performing the predictive labeling described below. In some cases, the non-transitory computer-readable medium 160 may include multiple levels of memory with different amounts of access latency. For instance, the non-transitory computer-readable medium may include a main memory 161 that has a first level of access latency, and may include a secondary memory 162 that has a second level of access latency higher than the first level. In one example, the main memory 161 comprises processor cache, dynamic random access memory (DRAM), and/or flash memory, while the secondary memory 162 includes a hard disk drive (HDD).

Figure 1B:
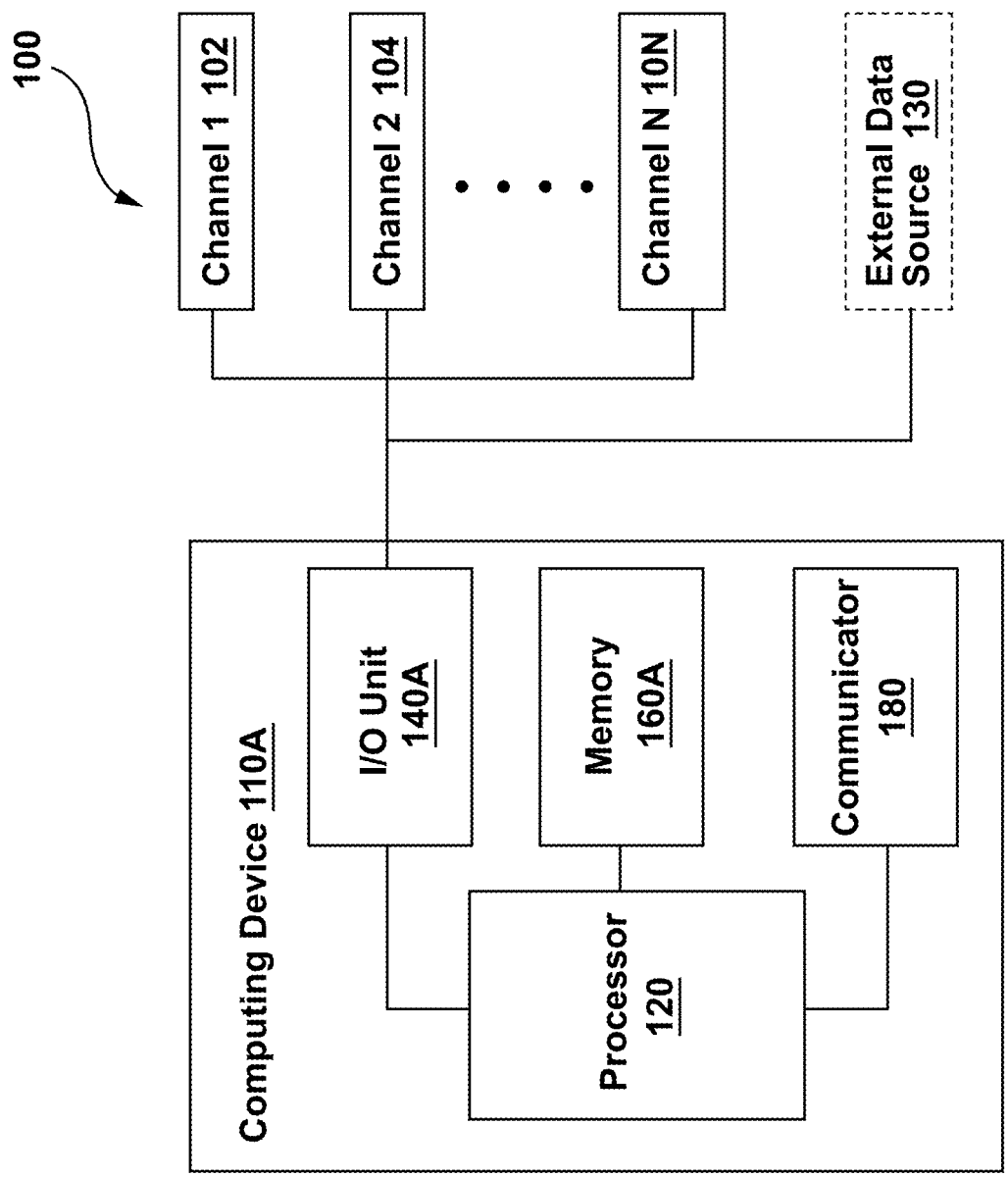
FIG. 1B is an illustrative example of a system for image analysis.

The computing device 110 can be part of a system 100 for image analysis. For instance, FIG. 1B shows a system 100 for image analysis, according to some embodiments. The system 100 includes a set of input channels 102, 104 . . . 10N. Each of the input channels 102, 104 . . . 10N can provide imaging data about cellular structures from one or more specific imaging modalities. For example, each channel 102, 104 . . . 10N can be an input source from an imager acquiring data through imaging modalities like bright-field imaging, darkfield imaging, fluorescence imaging, Dodt Contrast Imaging, Differential Interference Contrast (DIC) Imaging, etc. In some embodiments, the system 100 can include the instrumentation for the imaging modalities. For example, the system 100 can include instrumentation for fluorescence imaging which can include: a microscope, one or more light sources (e.g., UV source, confocal laser) for excitation of the sample, one or more optical elements (e.g., image sensor and grating filter or dichroic mirror) to collect the emitted fluorescence or transmitted light and to filter the collected light at appropriate wavelengths, one or more light detectors to transduce and register the collected light, one or more data acquisition and storage devices to obtain and store the transduced signals, etc.

In some embodiments, at least one of the channels 102, 104 . . . 10N can also be input sources of three dimensional imaging data labelled with one or more tags, each tag corresponding to a different identifiable cellular structures. For example, certain structures labelled with a green fluorescent label emitting fluorescence near the green wavelength (e.g. Green Fluorescent Protein (GFP) emitting maximally around 532 nm) can be acquired through channel 102, while certain other cellular structures labelled with a red fluorescent tag emitting fluorescent light at wavelengths corresponding to orange or red light (e.g. red fluorescent protein emitting maximally at around 588 nm) can be captured through imaging via Channel 104. The identification of a cellular structure bound by a known label or marker can also be referred to as an indication of the location of the cellular structure. Similarly, any channel N (10N) can be a source of imaging data labelling specific structures using specific fluorescent tags. While the system 100 is described in the context of imaging cellular structures, it must be noted that the system can be also used for imaging sub-cellular structures or other objects for example, imaging within sub-structures of cells like the nucleolus. The system can also be used to image super-cellular structures, for example groups of cells, networks of cells, regions of living tissue containing cells, etc.

In some embodiments, the system 100 can also optionally include an External Data base 130 containing any data (from imaging or otherwise) useful for predictive localization of cellular structures in three dimensional image stacks, by transferring information from one imaging modality to another.

The system 100 can include a computing device 110A, which may be an embodiment of the computing device 110. The computing device 110A may be configured to carry out the implementation of predictive localization of objects in image data, such as image data that was obtained using bright field microscopy or other form of unlabeled imaging. The computing device 110A can include an Input/Output Unit (I/O Unit) 140A, a memory 160A, a processor 120, and a communicator 180. The I/O unit 140A may be an embodiment of the communication interface 140, while the memory 160A may be an embodiment of the non-transitory computer-readable medium 160. The I/O unit 140 may be configured to receive and transmit information to and from the computing device 110A. For example, the device 110A can receive information from the Channels 102, 104, 10N, and from the External Data Source 130, via the I/O Unit 140A through any suitable wired or wireless connection. The I/O Unit 140A can receive analog and/or digitized signals. The I/O Unit 140A can also be equipped with one or more data acquisition boards to acquire analog signals and convert them to digitized signals. The I/O Unit 140A can also receive already digitized, pre-processed and/or processed digital data though any suitable communication wired or wireless channel. For example, wired data transfer can be mediated by the I/O Unit 140A through Ethernet, FireWire, or USB connections connected to one or more input ports. In some cases, the device 110A can be local to the instrumentation that is generating the image data. In some cases, the device 110A can be configured to communicate with the instrumentation via a network. The I/O Unit 140A can also be configured to receive and transmit information wirelessly though Bluetooth, or NFC channels.

As stated above, the device 110/110A of the system 100 can also include a processor 120 configured to carryout predictive localization of objects in image data of one modality based on information from image data of another modality. In some embodiments, the processor 120 can encompass a multiprocessor setup including one or more central processing units (CPUs) and/or Graphic Processing Units (GPUs). In an embodiment, the processor 120 can include a processing circuit such as a field programmable logic array (FPGA), application specific integrated circuit (ASIC), programmable logic array (PLA), a digital signal processor (DSP), or any combination thereof. The processor 120 can be configured to carry out predictive localization of cellular structures from images. For example, the processor 120 can be configured to carry out processes such as image segmentation to analyze labelled images, stack handling to handle 3D image stacks, data segmentation to select and allocate the training and testing data sets, to generate a statistical model, and to train the statistical model through iterative parameter optimization. In an embodiment, the processor can be configured to generate an output image from an input image, wherein the input image can be an unlabeled image of a cell obtained via bright field microscopy or another imaging modality, and the output image can show the estimated and/or predicted localization of objects, such as cellular structures and substructures within the cell. The processor 120 can also be configured for testing a statistical model to validate the accuracy of the statistical model at predicting localization. In an embodiment, the processor 120 can also be configured to perform other functions including, but not limited to, image rendering to visualize an original or generated image stack, overall development and validation of prediction and evaluation tools, by comparing the output of several models and loss functions based on different statistical methods, machine learning methods, or neural network topologies, etc.

The device 110A of the system 100 can also include a memory 160A. The memory 160A can include a hard disk drive (HDD), a solid state drive (SDD), a tape drive, DRAM, any other form of memory, or any combination thereof. In some cases, the memory 160A can be or can implement a database. As stated above, the memory 160A can be an embodiment of the non-transitory computer-readable medium 160, and may store one or more computer executable instructions executable by the processor 120 to perform the methods described herein, including a set of functions for executing the process of predictive localization of structures from image data and storing any information associated with the execution. In an embodiment, the memory 160A can store data such as acquired 3D image data, the statistical model discussed above, including any contained transform functions and their parameters of the model used to perform predictive localization, or any other data. In an embodiment, the memory 160A can also store a history of trained statistical models built to perform predictive localization, the accuracy of prediction with each trained statistical model, as well as the predicted image data. Further in FIG. 1B, the computing device 110A can also include a communicator 180, which may be another communication interface, and may be configured to mediate communication between the device 110A and any external source of information, such as a remote servers containing databases, etc. The communicator 180, the memory 160A, the processor 120 and the I/O Unit 140A can all be interconnected, and in direct communication with each other. The communication interface 180 can handle data exchange with external sources 130 either directly or through the I/O Unit 140A.

Figure 2A:
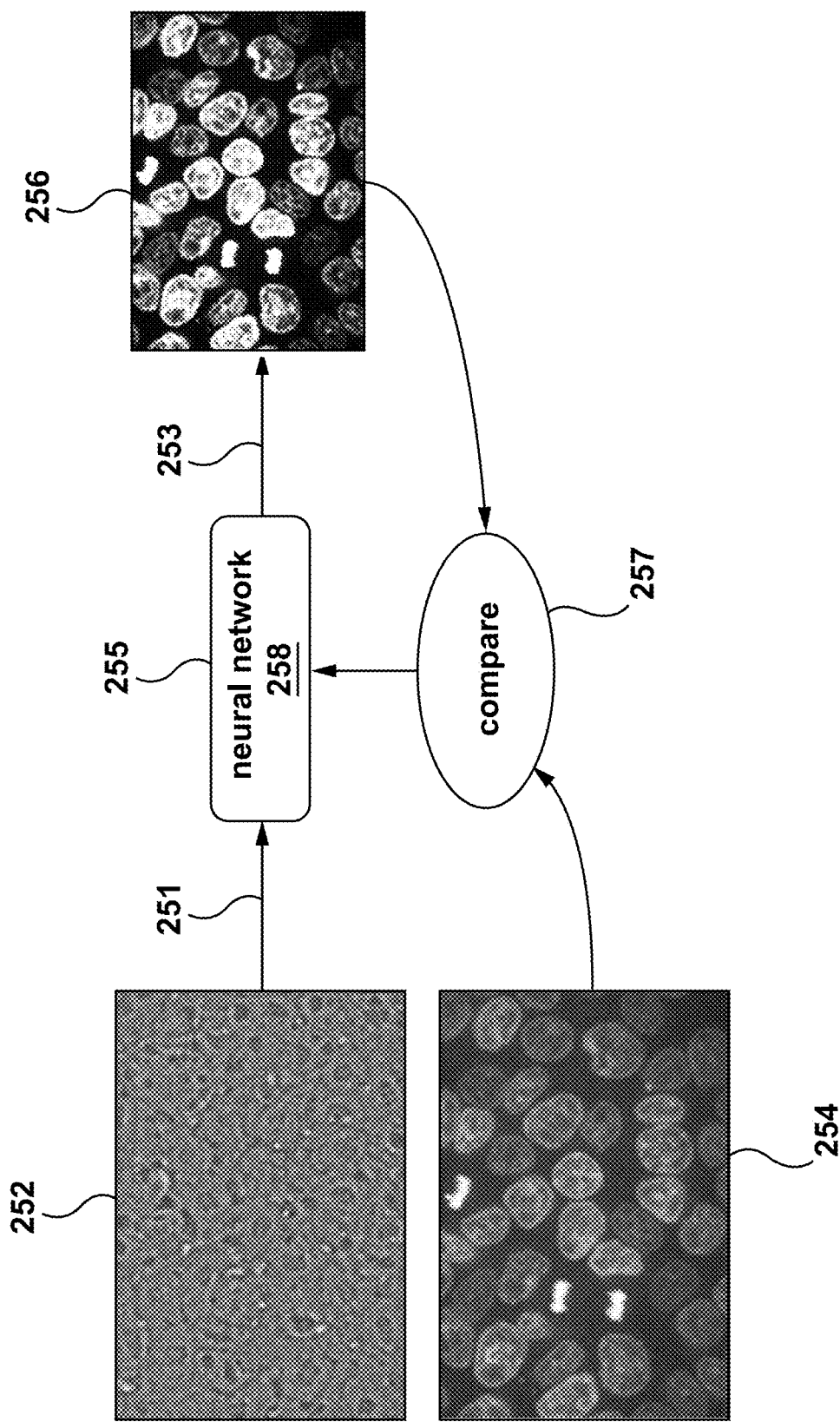
FIG. 2A is an illustrative schematic of a process of predictive localization in unlabeled images.

FIG. 2A illustrates an example of a system for generating and iteratively training a statistical model, which can also be referred to more generally as a model, for visualizing the localization of cellular structures by predicting or otherwise identifying the location of tags, dyes, and other labels for those cellular structures. In the example of FIG. 2A, the cellular structures can be DNA structures within a cell. More particularly, FIG. 2A illustrates some of the steps involved in each iteration of training the statistical model, to optimize the parameters of the statistical model for the predictive localization of the DNA structure within cells. For instance, the processor 120 discussed above can be configured to retrieve a transmitted light image 252 of a piece of tissue sample. The transmitted light image 252 can be considered an unlabeled image. The processor 120 can be configured to generate a statistical model, such as a neural network 258, using the unlabeled image 252 and a labeled image 254 of the tissue sample. The tissue sample can include living or non-living matter (e.g., fixed tissue, excised tissue, biopsy sample etc.,) capable of being stained, and can be of animal or plant origin. The tissue can be derived from cell lines and/or include natively—derived cells and tissues. In an embodiment, image 254 and image 252 are of the same section of tissue. Image 254 can be a fluorescent image (also referred to as a fluorescence image) of that same section of the tissue sample, wherein the DNA structure is labelled with a fluorescent Hoechst dye that binds to DNA material as an example, although other labels (e.g. dyes, and/or tags) could be used. In an embodiment, the image 252 and the image 254 may be brought into alignment with each other before being used to train the neural network 258.

At step 251, the processor 120 can generate and train the neural network 258 or other statistical model to learn the association between the unlabeled image 252 and the labeled image 254. At step 255, the processor 120 can use the trained neural network 258 to apply the trained statistical model on the unlabeled image 252 to generate, at step 253, a predicted labeling indicated by generated image 256. For instance, the predicted labeling can predict or otherwise estimate which portions of the unlabeled image 252 of a biological sample (e.g., tissue sample) would have a particular dye color if the image 252 had instead been obtained by performing fluorescence imaging on the same sample. This prediction can be used to generate a predicted (e.g., approximate or estimated) fluorescence image of the biological sample from an unlabeled image.

Any predictive approach, such as that of a statistical model trained, optimized and/or implemented by a processor as disclosed herein can be validated to evaluate its accuracy of prediction. Further, the performance of the statistical model can be improved with feedback from the results upon validation. In an embodiment, the processor can perform the validation by, among other things, comparing a labeled image, such as the actual fluorescence, tagged, or dyed image, which could be from a first set of 3D images of multiple sets of 3D images, with the predicted fluorescence image 256 generated in step 253, sometimes referred to as a third set of 3D images. More specifically, the processor 120 in step 257 can evaluate the accuracy of the prediction in step 255 and evaluate the accuracy of the predicted image generation in step 253 by comparing the true DNA labeled image 254, with the generated image 256 with predicted fluorescence labeling.

Figure 2B:
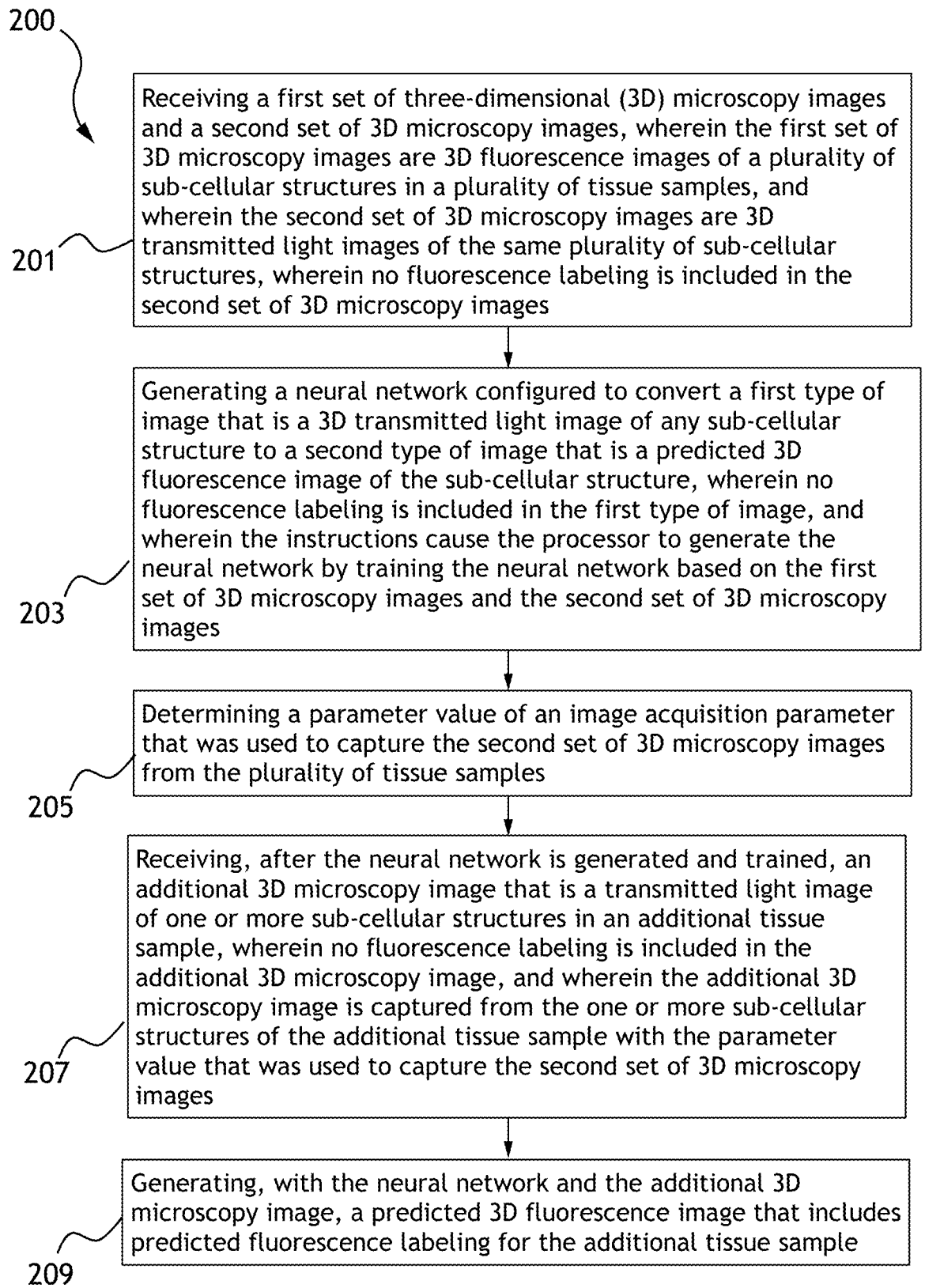
FIG. 2B is a flow diagram of an example method for generating a predictive 3D fluorescence image using a neural network.

FIG. 2B provides a flow diagram that depicts a method 200 for using a neural network to generate predictive fluorescence labeling. In an embodiment, the method 200 may be performed by a processor of a computing device executing computer-executable instructions stored in a non-transitory computer-readable medium, such as the processor 120 executing instructions stored in the non-transitory computer readable medium 160. As described below, the method 200 may focus on three-dimensional (3D) images of sub-cellular structures. The sub-cellular structures (also referred to as intracellular structures) may include cell components and other structures smaller than the cell level, such as cell membranes, nucleus, and cell organelles (e.g., mitochondria, endoplasmic reticulum, vacuole, Golgi Apparatus, or a lysosome). In some instances, the use of 3D images may be advantageous, because they may contain image data along an additional dimension (relative to 2D images), and thus may provide more image data for training the neural network described below. However, the use of 3D images may involve additional processing that deals with the significantly larger memory size of such 3D images.

In an embodiment, the method includes step 201, in which the processor 120 receive a first set of three-dimensional (3D) microscopy images and a second set of 3D microscopy images. In an embodiment, the first set of 3D microscopy images and the second set of 3D microscopy images are received via a communication interface, such as the I/O unit 140, from an image storage device or directly from an image sensor of a microscope.

In an embodiment, the first set of 3D microscopy images may be 3D fluorescence images of a plurality of sub-cellular structures in a plurality of tissue samples, and the second set of 3D microscopy images are 3D transmitted light images of the same plurality of sub-cellular structures, wherein no fluorescence labeling is included in the second set of 3D microscopy images. The plurality of sub-cellular structures may be divided among the plurality of tissue samples. For instance, a first subset of the plurality of sub-cellular structures may be in a first tissue sample, while a second subset of the plurality of sub-cellular structures may be in a second tissue sample.

In an embodiment, the first set of 3D microscopy images may include a single fluorescence channel, wherein each channel may correspond to a particular fluorescence marker or its emission spectrum. For instance, such a set of 3D microscopy images may include color (or, more generally, contrast information) from only green fluorescence protein (GFP), or from only a frequency filter band corresponding to the emission spectrum of GFP. Such 3D microscopy images may thus display or otherwise include only those sub-cellular structures in a particular tissue sample that are tagged by GFP. In an embodiment, the first set of 3D microscopy images may include multiple fluorescence channels.

In an embodiment, the second set of 3D microscopy images may have been captured with transmitted light using, e.g., Kohler illumination. In an embodiment, each of the second set of 3D microscopy images is at least one of a brightfield image, a darkfield image, or a differential interference contrast (DIC) image. In an embodiment, the sub-cellular structures to which method 300 is applied may include structures (e.g., mitochondria) having a lipid envelope, which may exhibit a different refractive index than its surrounding. As stated above, the second set of 3D microscopy images do not include any fluorescence labeling. More specifically, the second set of 3D microscopy images may have been captured from the plurality of tissue samples before any fluorescent markers were applied to those tissue samples.

In step 203, the processor 120 generates a neural network (e.g., a convolutional neural network having a u-net architecture) configured to convert a first type of image that is a 3D transmitted light image of any sub-cellular structure to a second type of image that is a predicted 3D fluorescence image of the sub-cellular structure, wherein no fluorescence labeling is included in the first type of image. The processor may generate the neural network by training the neural network based on the first set of 3D microscopy images and the second set of 3D microscopy images. In an embodiment, the training may be done on a channel-by-channel basis. For instance, the first set of 3D microscopy images may include a plurality of fluorescence images for a particular tissue sample, wherein each of the plurality of fluorescence images may correspond to a different respective fluorescence channel. In this example, the second set of 3D microscopy images may include a single brightfield image for the particular tissue sample. The training of the neural network may involve creating multiple pairs of images, wherein each pair includes the brightfield image and one of the plurality of fluorescence images. Each pair of images may be fed to the neural network in order to train the neural network for the fluorescence channel corresponding to that image pair. After such a neural network is trained, it may be able to convert a brightfield image into a predictive fluorescence image for all fluorescence channels, or for only certain fluorescence channels selected by a user.

The training of the neural network is described below in more detail. For instance, the training may involve feeding a transmitted light image into the neural network, generating an output using the neural network, comparing the output with a fluorescence image, and using a loss function to evaluate the accuracy of the output. The training may then use backpropagation to adjust weights in the neural network in order to reduce value of the loss function. In an embodiment, the total number of training images (e.g., total number of the first set of 3D microscopy images, or the total number of the second set of 3D microscopy images) used in step 203 may be in a range of 1 to 540. For instance, some implementations may rely on less than 500 transmitted light images and less than 500 fluorescence images (per fluorescence channel) to perform the training. In an embodiment, the fluorescence image and a transmitted light image for the same tissue sample may be in alignment before they are used to train the neural network. In an embodiment, each of the plurality of tissue samples may include live cells. Because the live cells may be moving, the amount of time spent capturing each of the 3D microscopy images may be limited to, e.g., 25 ms (25 ms/channel), so that the sub-cellular structures captured by a transmitted light image are still in substantially the same location or substantially the same shape when they are also captured by a fluorescence image.

In an embodiment, the training images are not normalized. In another embodiment, the training images are normalized using a z-score on only the first set of 3D microscopy images, on only the second set of 3D microscopy images, or on both. In an embodiment, the training may use a depth hyperparameter that is in a range of 1 to 4, and/or a channel expansion factor hyperparameter that is in a range of 16 to 40. In an embodiment, the training images are not augmented. In another embodiment, the training images augmented by being mirrored along a y-dimension, or rotated about a z-axis. In an embodiment, a learning rate of the model parameter optimizer may have a value that is in a range of 0.00001 to 0.1.

In step 205, the processor 120 determines a parameter value of an image acquisition parameter that was used to capture the second set of 3D microscopy images from the plurality of tissue samples. In one example, the image acquisition parameter is an exposure time parameter. In one example, the image acquisition parameter may be a thickness of each of the plurality of tissue samples.

In step 207, the processor 120 receives, after the neural network is generated and trained, an additional 3D microscopy image that is a transmitted light image of one or more sub-cellular structures in an additional tissue sample, wherein no fluorescence labeling is included in the additional 3D microscopy image (e.g., no fluorescence marker was applied to the additional tissue sample), and wherein the additional 3D microscopy image is captured from the one or more sub-cellular structures of the additional tissue sample with the parameter value that was used to capture the second set of 3D microscopy images. In some cases, the additional 3D microscopy image may have been captured from a live cell or live cells in the additional tissue sample.

In step 209, the processor 120 generates, with the neural network and the additional 3D microscopy image, a predicted 3D fluorescence image that includes predicted fluorescence labeling for the additional tissue sample. The predicted fluorescence image may include all the fluorescence channels for which the neural network was trained, or include only a subset of the fluorescence channels. In an embodiment, steps 207 and 209 may be performed multiple times over a time span of, e.g., hours or days, on one or more sub-cellular structures in a tissue sample, and the resulting set of predicted fluorescence images may be used to generate an animation of the one or more sub-cellular structures.

In some cases, the method 200 may omit one or more of the above steps. For instance, step 205 may in some instances be omitted, and the transmitted light images used to train the neural network may be captured with different image acquisition parameter values than those used to later capture a new transmitted light image.

As discussed above, the 3D microscopy images may pose significant technical challenges because of their large size. In many instances, the 3D microscopy images occupy significant memory space, and may not fit in the main memory (e.g., 161) of a computing device. Thus, one aspect of the embodiments herein relate to overcoming such technical challenges. In an embodiment, the non-transitory computer-readable medium (e.g., 160) of computing device (e.g., 110) may have a first memory portion (e.g., main memory 161) and a second memory portion (e.g., secondary memory), wherein the first memory portion has a first level of access latency, and the second memory portion has a second level of access latency longer than the first level. In this example, a total storage capacity of the first memory portion 161 is less than a total memory size of the first set of 3D microscopy images and the second set of 3D microscopy images. In a more specific example, an amount of memory space allocated in the first memory portion 161 is less than the total memory space of the 3D microscopy images.

In the above embodiments, the processor 120 may store the first set of 3D microscopy images and the second set of 3D microscopy images in the second memory portion. The processor 120 may train the neural network over a plurality of iterations with different respective portions (also referred to as different respective batches or sub-sampled chunks) of the first set of 3D microscopy images and different respective portions of the second set of 3D microscopy images. During each iteration, the processor may retrieve from the second memory portion only a respective portion (also referred to as a respective batch or chunk) of the first set of 3D microscopy images and only a respective portion of the second set of 3D microscopy images. The processor may store the respective portion of the first set of 3D microscopy images and the respective portion of the second set of 3D microscopy images in the first memory portion. The processor may then train the neural network during the iteration with the respective portion of the first set of 3D microscopy images currently stored in the first memory portion, and with the respective portion of the second set of 3D microscopy images currently stored in the first memory portion. Thus, the processor in this embodiment may load different batches of image data of the 3D microscopy images from the secondary memory 162 into main memory 161, in order to make the batches available for training on that batch of image data. After a training iteration is completed for a particular batch or chunk, the processor may overwrite that batch or chunk in the first memory portion with a different batch or chunk of image data, and perform training on that batch or chunk. Thus, such a manner of performing the training may accelerate training speed and reduce the amount of main memory that is needed to perform the training, which may allow the training to be performed on commodity hardware, such as a desktop computer.

In an embodiment, the processor may also conserve memory space by downsampling each of the first set of 3D microscopy images and each of the second set of 3D microscopy images, before they are used to train the neural network. For instance, the 3D microscopy images, after being downsampled, may represent a range of 0.108 μm to 0.29 μm per pixel along at least one of the dimensions of the respective 3D microscopy image.

Figure 3A:
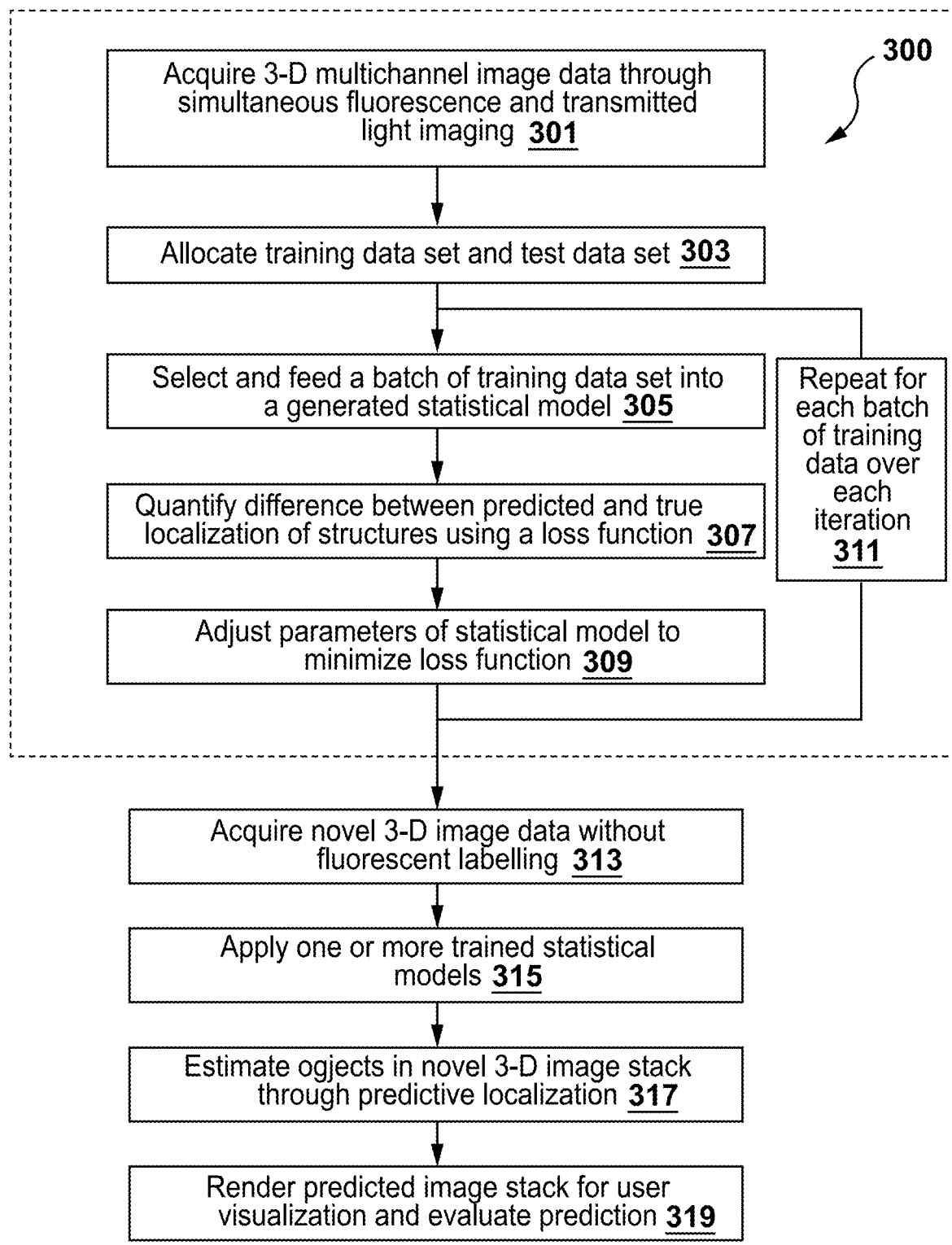
FIG. 3A illustrates an example of a method for predictive localization.

FIG. 3A illustrates a method 300 to implement predictive localization of structures that more generally uses a statistical model. In some embodiments, the method 300 can be executed by the processor 120 in the system 100 shown in FIG. 1B. The method 300 includes a set of steps 301-309 for training a statistical model, indicated by the dotted lines, and a subsequent set of steps 311-319 for implementing the trained statistical model. In an embodiment, the training and testing can be done sequentially on a given set of data. In other embodiments, the training can be conducted separately and the trained statistical model can be applied on several new data sets that are comparable to the training data set.

The method 300 includes, at step 301, a processor such as processor 120 acquiring image data from an example living tissue to be studied. In some scenarios, the image data acquired can be a three dimensional stack of images, each image of the stack corresponding to a 2D slice of the three dimensional piece of tissue, the images acquired from sufficiently resolvable slices. The acquired data can also be a time resolved stack of images, with each image of the stack corresponding to the same two dimensional slices of a tissue but at sequential points in time. In one example, the images may be resized via cubic interpolation such that each voxel corresponds to a 0.29 μm×0.29 μm×029 μm cube (or any other size), and pixel intensity of the images may be z-scored.

In an embodiment, the acquired data can be a three dimensional stack of multi-channel imaging data, each channel of data corresponding with a channel source like Channel 1 102 and Channel 2 104, Channel N 10N, etc. shown in the system 100 of FIG. 1. The multi-channel data acquired in step 301 can include at least one channel providing labeled data, such as images of a sample with a known label associated with specific known objects or structures in the sample. For example, the data acquisition in step 301 can include at least one channel of fluorescently labelled data bound to specific cellular structures that are to be localized. The processor in step 301 can also obtain unlabeled data, such as three dimensional image stack data of at least one imaging modality that is devoid of labelling. In some cases, the labeled data and the unlabeled data can be images of the same exact region of a tissue sample or other sample. For example, the three dimensional image stack acquired by the processor in step 301 can include a channel of data obtained through transmitted light imaging or, more specifically, bright-field imaging. In one embodiment, the bright-field imaging that is acquired might not have fluorescent staining or other labeling of specific structures of the imaged sample, though the fluorescent staining may be present in another embodiment. In an embodiment, the labeled data can include a three dimensional stack of data, which can include several labelled stacks highlighting various different structures of the cells, in an overlapping or non-overlapping fashion. As an example, the labeled data can include several fluorescent labels, wherein each of the fluorescent labels is substantially distinct from other labels of the fluorescent labels based on the emission spectrum, and each of the labels can be associated with one or more distinct cellular structure in the same image. In an embodiment, the labelled and unlabeled channels of image data can be acquired in a near simultaneous manner such that objects to be identified in each of the image stacks are located spatiotemporally in the same position.

Figure 4A:
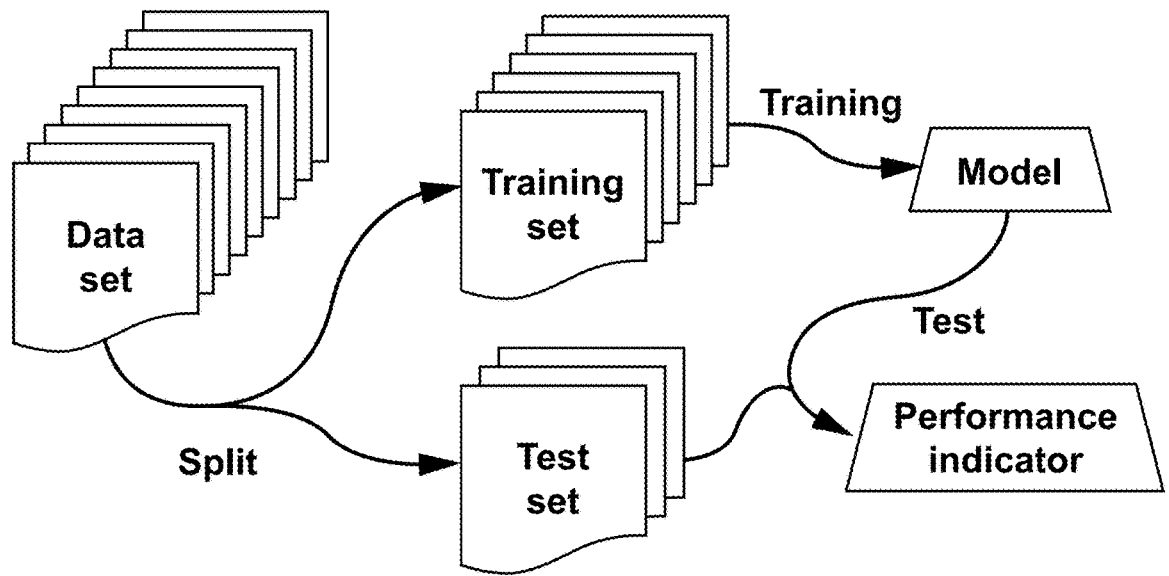
FIG. 4A is an example process of generation of predictive statistical models for object localization, according to an embodiment.

At step 303 of the method 300, the processor can allocate a training data set for training a statistical model, such as a neural network. The training data can include image data of the cells/tissues captured with and without labelling. In an embodiment, the allocated training data set can be used to optimize a set of parameters of a statistical model designed to capture a desired target labeling, through an iterative training procedure. Some or all of the remaining data that was acquired in step 301 can be used as a testing data set used to evaluate the trained model's performance in predicting the desired labeling. The allocation of training data set vs testing data set can be carried out in any suitable manner, such as by assigning a percentage of randomly selected three dimensional stacks of images, or time resolved image sets as training data set, while retaining the remaining as testing data set. Alternatively, the allocation can include assignment of a percentage of individual slices or two dimensional images as training data set, irrespective of the stack they belong to, while retaining the remaining as testing data set. An example allocation of training and testing data set is shown in the illustration of an example procedure for model generating and testing in FIG. 4A. While the allocation in the example illustrated in FIG. 4A indicates a larger portion of the data as training data set and a smaller portion as the testing data set, in other embodiments, the image data can be split at step 305 in any other manner. For example, the data can be split in half and an equal portion of the data can be assigned to each, the training data set and the testing data set.

In an embodiment, the processor in step 303 may be configured to select a portion of the acquired image data, and use only that portion to perform the training of a statistical model. That is, under certain conditions when the image stacks or even the individual images are too large to be used entirely, randomly selected subsections of the original images can be assigned to the training data set. Similarly, randomly selected subsections can be assigned to the testing data set. The testing data set can be separate from the training data set to enable robust validation, while general image properties like brightness, contrast, magnification, illumination etc. can be held constant so that rules learned from the training data set can be applied for testing and performance. General image properties like brightness, contrast, magnification, illumination etc. can be acquired along with the image data from each channel by the I/O Unit 140 and stored with the image data in the memory 160. Each training or test image data set thus can have an associated image properties data set that is to be considered when using the image data set to generate statistical models or to perform predictive localization of structures for study. Once trained, the statistical model can be applied on unlabeled, new data (sometimes also referred to as a third set of 3D images) with similar general image properties as the training data set to identify structures based on the selected image-based features. Said another way, the tissue and imaging conditions during collection of new testing data set can be otherwise comparable (except for the lack of labeling) to the collection of training data set.

Reverting to FIG. 3A, following data allocation, at step 305, the processor can train the statistical model (also referred to as a generative model) using an iterative training procedure. The training causes the model to learn the association, or more generally a relationship, between pairs of labeled and unlabeled images from the training data set. For instance, the model may represent a nonlinear function that attempts to relate pixels of an image to the fluorescent labels of those pixels. The training can include steps 305-309, in which one or more parameters of the statistical model is adjusted to decrease a loss function. In the method 300, steps 305-309 represent one iteration, which can be repeated as indicated by the repeating or step 311. More specifically, at step 305, the processor can select a batch of paired images (e.g., in the form of an image stack) from the training data set. For example, batches of paired unlabeled and labeled images of the training data set can be selected and fed into the statistical model in several iterations. As an example, in some embodiments, batches of 24 volume pairs or 30 volume pairs of 32×64×64 pixel (ZYX dimensions) image stacks can be randomly sampled from the training data and used in each iteration of the training procedure.

In an embodiment, the statistical model can include a set of parameters or parameter values, such weight values in a CNN. In fact, the CNN can be especially suited to modeling a relationship between an unlabeled image and a labeled image. The processor can train the statistical model by adjusting the parameter values. In an embodiment, the processor can generate the statistical model with a set of starting parameter values for the first iteration, and with the unlabeled images of the selected batch of training data, which can be fed into the statistical model. In this manner, training of the statistical model can begin with the starting parameter values, which can be progressively updated in each successive iteration of the iterative training procedure. In an embodiment, the statistical model can contain a set of transform functions that are configured to transform, based on the parameter values of the model, an unlabeled image into an image having predicted labeling. The transform functions can be used to generate the predicted labeling in the output images of each iteration. The generation of images (sometimes also referred to as a fourth set of 3D images) illustrating the predicted labeling can also be referred to as an indication of the location of the cellular structure in the testing data set.

In each iteration of steps 305-309, the performance of the statistical model at predicting localization of a particular structure from the unlabeled image stack can be evaluated, and the parameters or parameter values of the statistical model can be adjusted appropriately to cancel or reduce the differences between the predicted localization (also sometimes referred to as the received indication of the location of the cellular structure in the testing data set) and the true localization from the corresponding labeled image stack of the training data set (also sometimes referred to as the estimated location of the cellular structure in the testing data set). More specifically, at step 307, the processor may compare predicted labeled images of the selected batch of training data set with the true labeled images of the selected batch of the training data set. For instance, the evaluation of the performance at each iteration can be conducted through a quantification of difference between predicted labeling and true labeling with a loss function. As an example, in some embodiments of predictive localization, the loss function may be a measure of mean squared error computed over the predicted and true labeling images.

Based on the results from evaluation, the model parameters can be adjusted, in a parameter optimization step, in the direction that is expected to minimize the loss function. For instance, following the quantification of performance in a particular iteration, the processor at step 309 can adjust various weights or other parameter values of the statistical generative model to bring the predicted labeled image closer to the true labeled image, based on the results of the loss function quantified at step 307. In other words, the parameter values of the statistical model can be adjusted with the appropriate degree and direction to minimize the loss function quantified at 307.

The steps 305-309 of training data selection, prediction of localization of a label and parameter optimization can be carried out for each distinct batch of training data set, as indicated by the repeating step 311 in the process 300 shown in FIG. 3A.

For instance, the steps of inputting a batch of training data, predicting localization, evaluating the loss function, and adjusting the parameters of the statistical model to minimize the loss function, through parameter optimization, can be repeatedly carried out in sequential iterations until the model parameters or model parameter values converge onto an optimal point of performance. Parameter optimization can be carried out using any suitable method, for example using gradient descent methods or methods of simulated annealing etc. In some embodiments, an Adam optimizer can be used to achieve parameter optimization through gradient descent. In some embodiments, using particular methods for parameter optimization, a learning rate can be set. The choice of optimizing method and the setting of learning rate can impact the degree to which parameters can be adjusted at each iteration, the degree of convergence, and the number of iterations required for convergence to a global minimum without being impacted by local minima. In some embodiments, the number of iterations can be set irrespective of the degree of convergence reached at the end of the iterative training procedure. The desired point of convergence and/or the desired number of iterations can be set based on the desired labeling requirements and the desired computing time. For example, in some implementations, the system trained with about 50,000 training iterations, although more or fewer training iterations can be used.

The steps 301-309 and the iterative loop 311 in FIG. 3A outline an embodiment of the process to train a statistical model to predict a specific labeling. The steps of allocation of training data set, and the iterative training procedure to converge at a suitable statistical model that predicts localization of a specific set of structures labeled in a specific set of labeled training data can be carried out for each distinct set of labeled training data labeling a distinct set of one or more cellular or sub-cellular or super-cellular structures.

The statistical model can be generated and trained or otherwise optimized using any suitable machine learning tool, implemented in any suitable computational environment using any suitable computing language. For example, the implementation can be done in environments like Python (e.g., PyTorch) or Matlab, and run on Nvidia® Pascal Titan X. The statistical model can be built, for example, using Distance Measures in linear or non-linear space. Model generation can also include supervised and/or unsupervised methods. For example, unsupervised approaches can include clustering methods, Independent Component analysis, Matrix Factorization methods, and/or the like. As another example, supervised methods can include using neural networks with or without hidden computing layers of neurons designed to find informative patterns of feature occurrence through non-linear statistical modeling. Some implementations of neural networks to carry out model generation and optimization can use one or more hidden layers of computing nodes that can feed forward and/or feedback information. In one embodiment of the system 100, the processor 120 of device 110 may generate and train a statistical model that includes one or more neural networks of various architectures including varying number of hidden layers, varying number of computing units per hidden layer, varying number of input and output layers, interaction between the different layers, degree of recurrence in the overall network architecture within and across layers, types of computing units used to generate each layer, computing capability (e.g., linearity or non-linearity) of each computing unit, handling of feedback etc.

For example, some embodiments of the system 100 and/or the process 300 can use deep convolutional neural networks for generating and optimizing the statistical model using training data sets. In an embodiment, the convolutional neural networks can include contracting paths to capture context of the image and symmetric expanding paths to enable localization of structures. For instance, the convolutional neural network can have a modified "u-net" architecture, with the u-net architecture being generally similar to that disclosed in Ronneberger O., Fischer P., Brox T. (2015) U-Net: Convolutional Networks for Biomedical Image Segmentation. In: Navab N., Hornegger J., Wells W., Frangi A. (eds) Medical Image Computing and Computer-Assisted Intervention—MICCAI 2015, the entire disclosure of which is incorporated herein by reference.

Figure 4B:
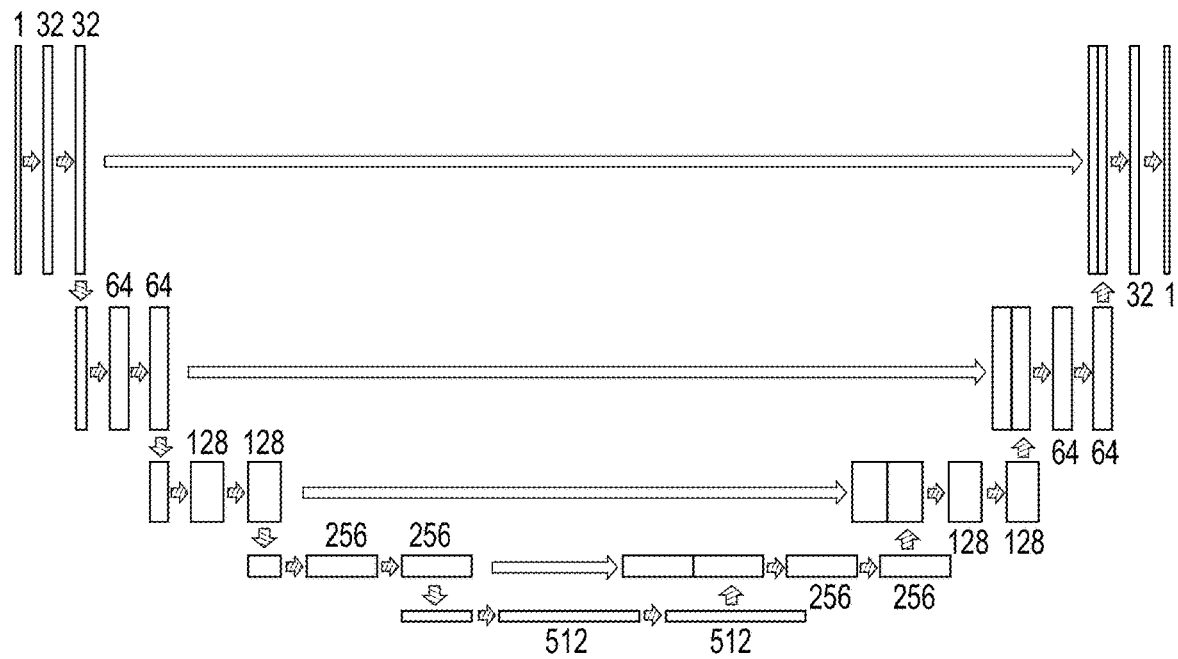
FIG. 4B is an illustration of an example convolutional neural network (CNN) with a modified U-net, that is useful for optimizing a statistical model for predicting object localization, according to an embodiment.

The convolutional U-nets can be modified in any suitable manner to better suit predictive localization of cellular or sub-cellular, or super cellular structures, based on the requirements. An example modified U-net neural network used in some embodiments of the system to carry out predictive localization is shown in FIG. 4B. For the implementation of multilayered neural networks or convolutional U-nets to perform object localization the device 110 and the processor 120 can include Central Processing Units (CPUs) or Graphic Processing Units (GPUs) for ease of high-speed image data processing and analysis.

In an embodiment, the convolutional U-net can be advantageous over other types of neural networks in situations where there are relatively few labeled images (e.g., less than 500) to use for training. The U-net can be represented as a function or series of functions, including linear filters and activation functions, that transform a first image, such as an unlabeled image, into a second image, such as a labeled image. The U-net can organize the filters into layers that perform one of three types of convolutions, followed by a batch normalization and rectified linear unit (ReLU) operation. The three types of convolutions include a 3 pixel convolution with a stride of 1 pixel on zero-padded input (such that input and output of that layer are the same spatial area), a 2 pixel convolution with a stride of 2 pixels (to half the spatial area of the output), or a 2 pixel transposed convolution with a stride of 2 (to double the spatial area of the output). In some cases, there is no normalization or ReLU on the last layer of the network.

Referring again to FIG. 3A, after converging on a suitable statistical model containing transform functions with optimized parameters, the processor in step 313 can receive new unlabeled data acquired following similar tissue preparation and unlabeled imaging conditions as was used for acquiring the training data set.

At step 315 of the method 300, the processor of the system can apply the trained statistical model with optimized parameters on the testing data set (e.g., the third set of 3D images), to obtain a images with predicted labeling of a specific set of target structures similar to the structures labeled in the training data set (e.g., fourth set of 3D images). For example, if a particular statistical model was trained with training data set containing labeling for DNA using a Hoechst marker, that trained statistical model can have transform functions with optimized parameters to accurately transform unlabeled images of a biological sample (e.g., tissue sample) into labeled images that approximate an image showing the Hoechst marker for that biological sample. The process of feeding the unlabeled images of a testing data set into the trained statistical model, by performing the image transforms dictated by the transform functions of the trained statistical model can also be considered as applying the trained statistical model to the unlabeled testing data set. For instance, if the trained statistical model included a U-net, the processor can transform the unlabeled testing data set using the filters and activation functions divided into multiple layers, wherein the filters have weights that were optimized during the training of the U-net.

As an example, the trained statistical model can be applied to predict the localization of DNA through the prediction of Hoechst labeling in the unlabeled testing data set. The unlabeled testing data set can be image data from a bright field image of a biological sample. Cell structures and other objects may be more difficult to see from the bright field image versus, e.g., an image that was dyed with a Hoechst marker. In step 319, the processor can render the predictive labeling with the unlabeled testing data set for user visualization. More specifically, the trained statistical model can predict where the Hoechst marker would appear in an image if it had been applied. The prediction may provide an approximation of whether the DNA is located in the image. In some embodiments, when predicting the localization of several structures using several different statistical models trained with several labeling channels, the system, at step 319, can also combine the several outputs image stacks into a merged composite image stack. Additionally, at step 319 the processor of the system can also evaluate the performance and quantify the prediction accuracy.

Portions of the test data can be used for evaluation of the performance of the trained statistical model. In case of large samples that used sub-sampling during the training procedure, the testing procedure may or may not use sub-sampling. In some embodiments, the performance of the statistical model can be quantified using a loss function similar to the one used during training. For example, a mean of the loss function value from each pair of labeled and unlabeled image stacks in the testing data set can be used to provide a metric for the trained model's performance. In some embodiments, the performance of the statistical model can be quantified or otherwise represented using a matrix representation of the results from prediction, as described below.

In an embodiment, steps 313-319 can involve acquiring a transmitted light image with an inter-slice interval that is the same or substantially the same as the inter-slice interval of the transmitted light image used in the training steps 301-311.

In an embodiment, the processor can use the trained model to generate time-series data with a bright-field or other transmitted light imaging technique. The time-series data may be outputted as, e.g., an animation that shows how a labeled cell structure changes over time. For instance, the animation may show a dynamic event such as mitosis of a human-induced pluripotent stem cell (hiPSc). In the bright-field images themselves, certain structures or features such as the breakdown and reformation of the nuclear envelope can be difficult to discern. However, because the animation was generated using the trained model, it can include colors or other forms of contrast that label specific structures such as the nuclear envelope. This technique is thus suited to visualizing dynamic events within a sample, especially long events lasting more than a few minutes, because it can be done without perturbing the sample. For instance, bright-field imaging can be performed on a cell for at least several hours without perturbing the cell. The resulting bright-field images may then be transformed using the trained model to generate an animation or other time-series data that shows predicted labeling of various cellular structures during that imaging time span. This cannot be done using fluorescence imaging, for example, because the chemicals used in fluorescence imaging may perturb the sample after just a short amount of time. For instance, if fluorescent labels were being used to label DNA and/or a cell membrane in a hiPSc cell, the chemicals used in the fluorescence imaging technique would cause the cellular structures to exhibit abnormal cellular morphology after only several minutes.

Figure 3B:
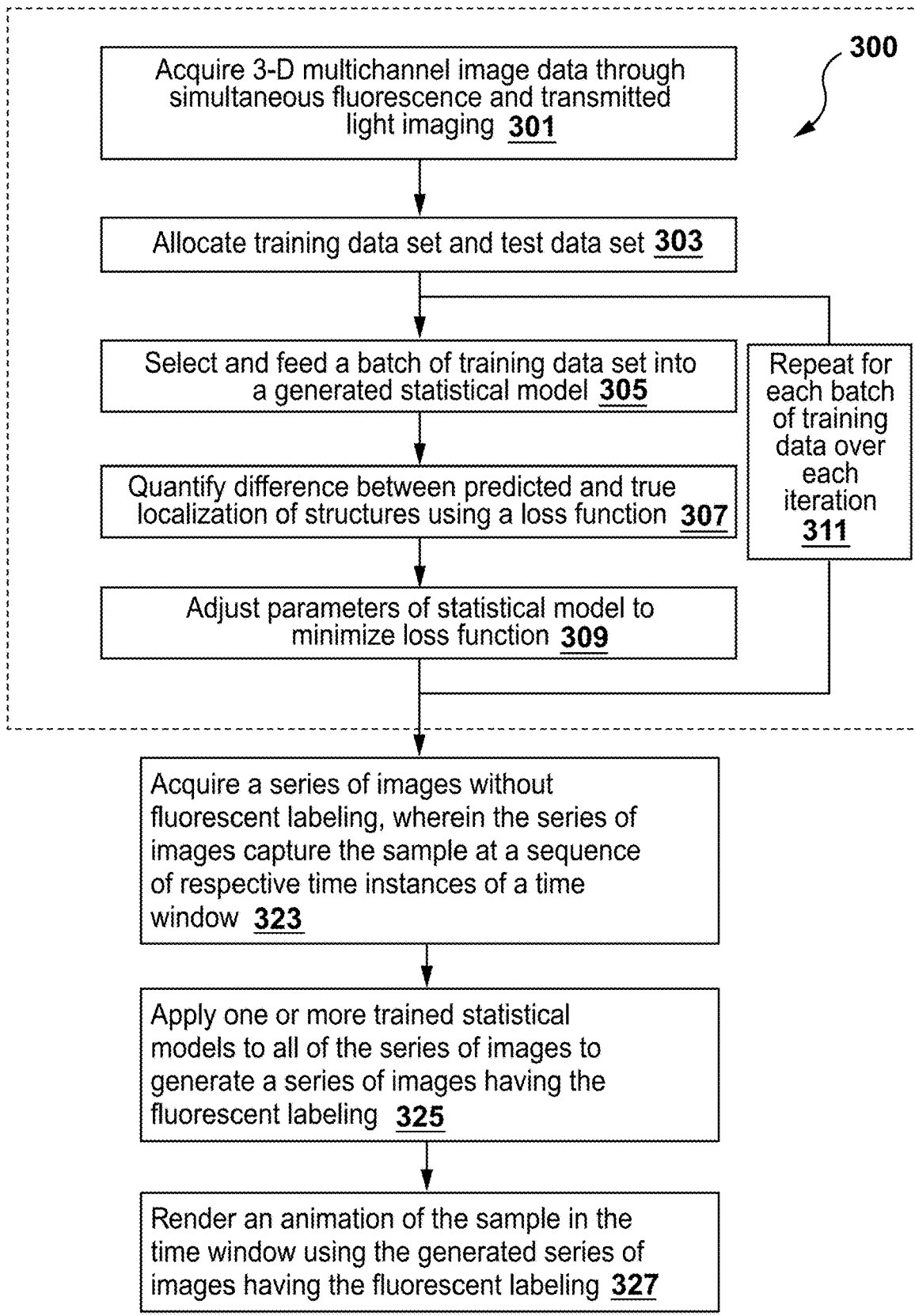
FIG. 3B illustrates an example of a method for using predictive localization to generate an animation or other time series data.

FIG. 3B provides a block diagram that illustrates a method 300A for generating time-series data, such as an animation, using unlabeled images. The method 300A includes steps 301-309, which are the same as those in FIG. 3A. The method 300A further includes a step 323, in which the processor, such as processor 120, acquires a series of images without fluorescent labeling or other labeling. The series of images can capture a sample at a sequence of respective time instances of a time window. For instance, during a 60-minute time window, the processor 120 can acquire a series of 120 images of a sample, wherein one image is captured every 30 seconds.

In step 325, the processor can apply one or more trained statistical models to all of the series of images to generate a series of images having the fluorescent labeling or other labeling. For example, the processor can apply a CNN to transform each image of the series of images to a labeled image that approximates a fluorescence image. The processor can perform the transformation on an image as soon as the image is acquired, or can perform the transformation after an amount of delay.

In step 327, the processor can render an animation of the sample in the time window using the generated series of images having the fluorescent labeling. For instance, if the sample is a cell that was undergoing mitosis in the 60-minute window, the animation may show an approximated labeling (or, more generally, predicted labeling) of various structures in the cell. The animation can thus make it easier to discern how the labeled structure changed during the 60-minute window.

Figure 5:
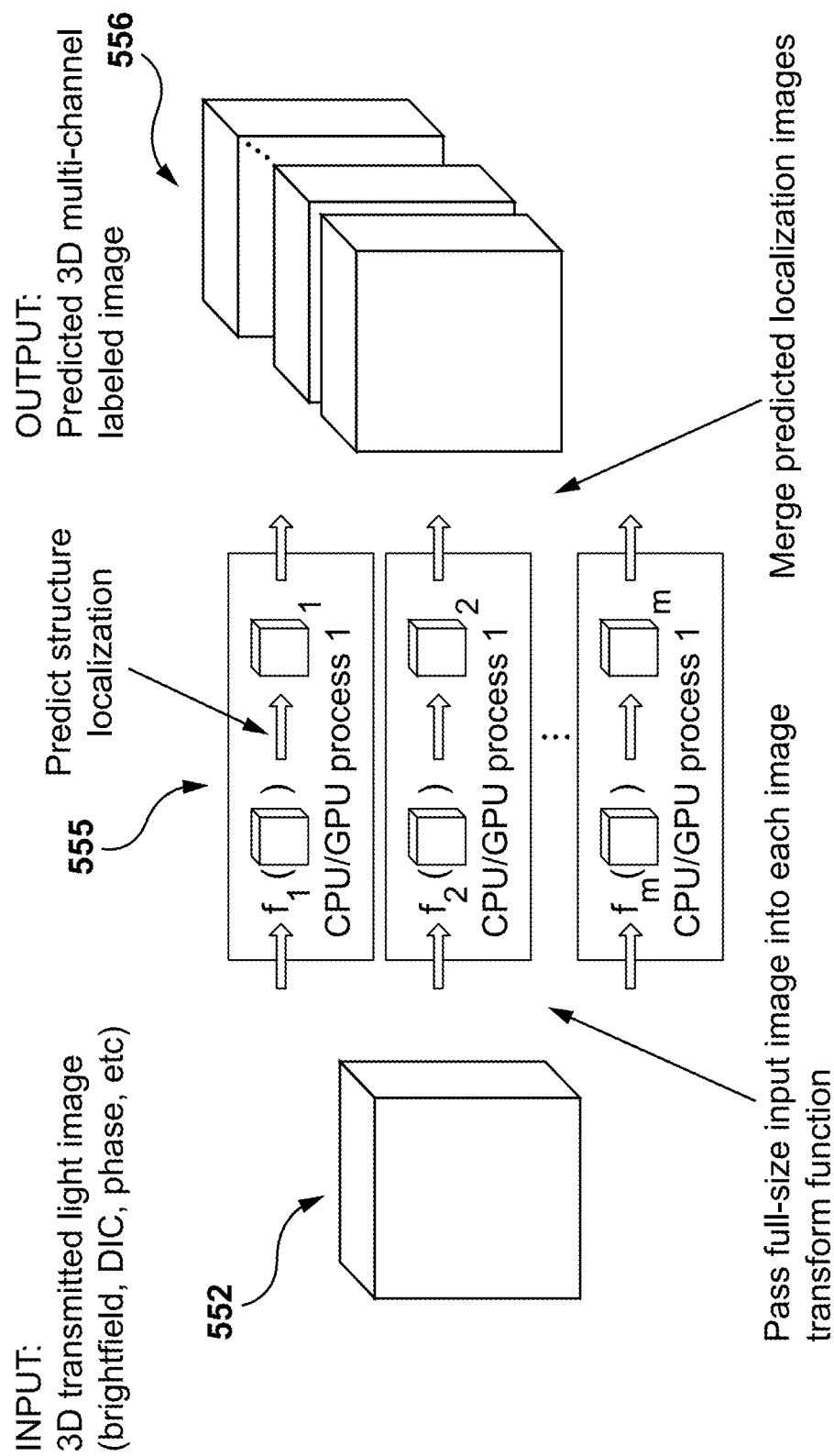
FIG. 5 is an illustration of an example process or system for predictive localization of cellular structures, carried out over a three dimensional multi-channel stack of transmitted light data, according to an embodiment.

FIG. 5 illustrates an overview of the system for generating predicted images (also referred to as predictive images) of the cellular structures. As indicated in the figure, a processor, such as the processor 120 of FIG. 1B, may receive an input image stack in the form of a three dimensional image stack 552 containing images of slices using an unlabeled imaging modality, for example, bright-field, DIC, phase contrast imaging, and/or the like. The input image stack 552 in FG. 5 is depicted as a cube and represents a three dimensional image stack. An example test data set can be of any suitable size, from as few as 15 images to as large as the entire set of training data/images. The desired labelling may be segregated into multiple channels, wherein each channel may correspond with a different structure, material, or component. For example, if separate labelling for DNA material, RNA material and cell membrane is desired, an embodiment of the system 100 can implement predictive localization at step 555 and predict labelling for three different structures. Predicting the labeling of structures in an unlabeled testing data set by applying a trained statistical model to generate a predicted labeled data set can also be referred to as generating a fourth set of 3D images, the fourth set of 3D images including an indication of the estimated location of the cellular structure. Predictive localization by applying a trained statistical model at step 555 is indicated by image transform functions $f_1, f_2 \ldots f_m$ carried out by CPU/GPUs which may be part of a device 110 and a processor 120 of a system 100. The results of each transform function is a separate labelled data set which can be reassembled into a three dimensional image stack as indicated. Image stack 556 is an example generated image stack containing predicted labeling of one or more structures. For instance, image stack 556 may include a first image, a second image, and a third image that are all images of the same portion of a biological sample. The first image may include or be accompanied by prediction data that predicts DNA labeling in the first image. The second image may include or be accompanied by prediction data that predicts RNA labeling in the second image. The third image may include or be accompanied by prediction data that predicts cell membrane labeling in the third image.

Figure 6:
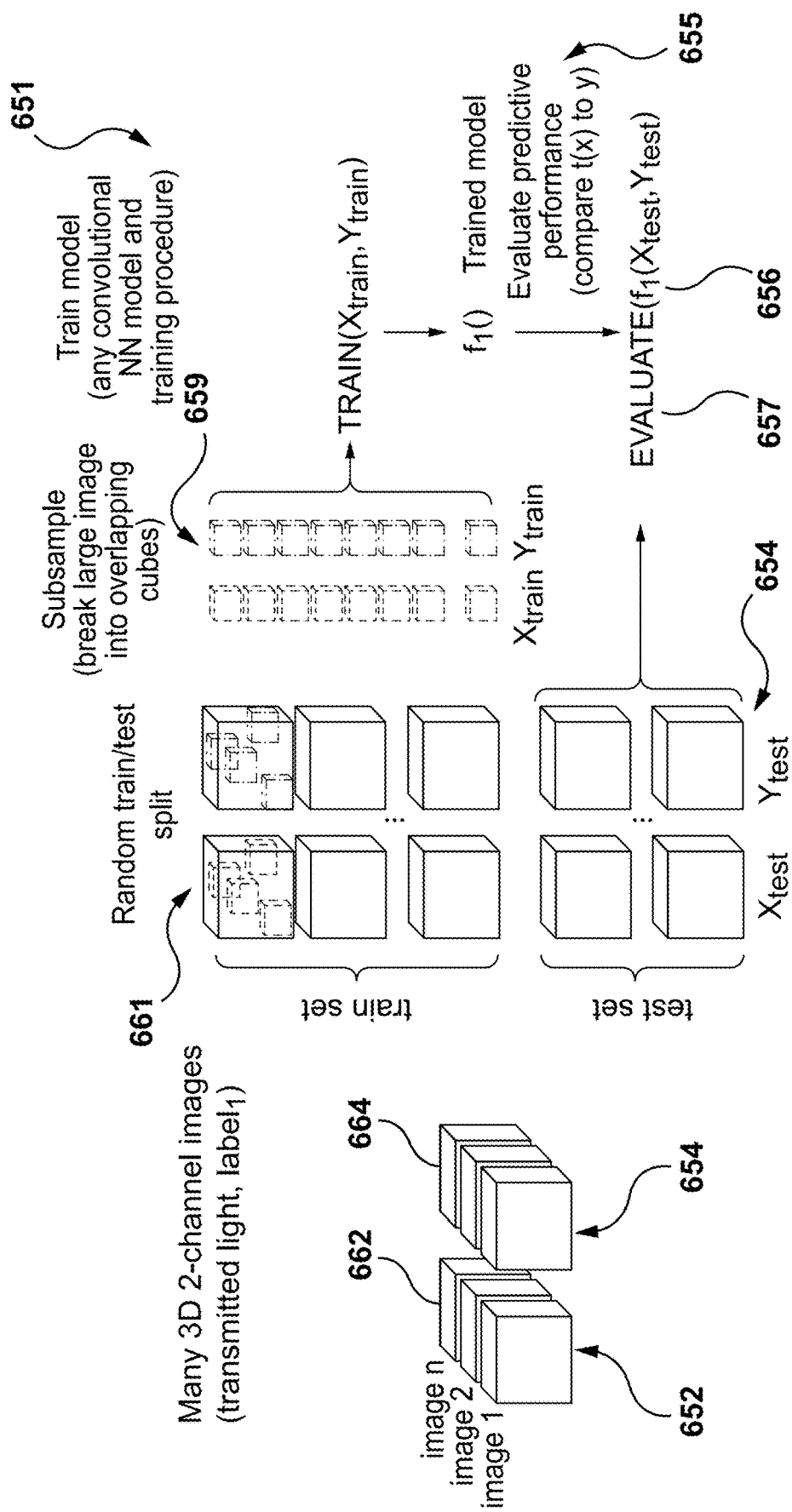
FIG. 6 is an illustrative overview of an example training procedure for applying image analysis to several 3D stacks of two channel imaging data, according to an embodiment.

FIG. 6 illustrates an example training procedure for image analysis over several pairs of three dimensional stacks. In an embodiment, each pair includes a first channel of image data capturing a region of a sample, and includes a second channel of image data capturing the same region. The input image data is illustrated in FIG. 6 as cubes, with each cube representing a three dimensional image stack of one channel. The input image data includes a set of image stacks 664 acquired through a labeled imaging method. The set 664 includes a first set of 3D images of multiple sets of 3D images, of which 654 is one. The input data also includes a set of image stacks 662, or second set of 3D images of multiple sets of 3D images, acquired through transmitted light imaging 662, of which 652 is one image stack.

In an embodiment, the set of image stacks 664 contain a first label ("label 1"), labeling a particular cellular structure of interest, and are paired with the set of image stacks 662. As indicated, this input image data is segregated or split at step 661 and some portions are assigned to the training data set while other portions are assigned to the testing data set. This assignment can be done through a process of randomized selection of individual stacks.

In an embodiment, sub-sampling can be performed in order to reduce the amount of computer memory that is needed to perform the training. Thus, the sub-sampling can improve the performance of a computer analyzing such images, by, e.g., providing faster response time and using less memory. For instance, as described earlier, under some circumstances when the entire image data from a single stack can be too large, the training data set stacks can be further sub-sampled at step 659 into smaller three dimensional sub-stacks or "chunks," which may also be referred to as voxels. The process of sub-sampling one or more smaller voxels or three dimensional chunks of the labeled image stack of the training data set can be also referred to as extracting a first (second, etc.) set of training images showing a first (second, etc.) region from the first set of 3D images. Similarly, sub-sampling one or more smaller voxels or three dimensional chunks of the unlabeled image stack of the training data set can be also referred to as extracting a first (second, etc.) set of training images showing the first (second, etc.) region from the second set of 3D images.

These sub-sampled chunks can then be used as training data set. This process of sub-sampling of chunks is indicated in FIG. 6 by the smaller cubes (chunks) selected randomly from within the training data set image stacks. The sub-sampled cubes or chunks can be partially overlapping or non-overlapping. The sub-sampled chunks of 3D training image data with a label(s) associated with one or more structures can be referred to as a first (second, etc.) set of training images showing a first (second, etc.) region from the first set of 3D images. Similarly, the chunks sub-sampled from the unlabeled 3D training image data can be referred to as a first (second, etc.) set of training images showing the first (second, etc.) region from the second set of 3D images. The training procedure can be the same or similar to a training procedure adopted for training with complete three dimensional stacks data. The training data set can then include a set of unlabeled data chunks $X_{train}$ that can be each paired with a labeled data chunk $Y_{train}$. Training involves arriving at the optimal relationship associating each $X_{train}$ data to its corresponding labeled $Y_{train}$ data. The example illustrated in. FIG. 6 shows an example training procedure 655 obtaining a statistical model represented by the transform function $f_1$.

Similarly, validation or evaluation of performance at step 657 can be done using either entire stacks or by using sub-sampled chunks as adopted with training and/or testing data sets. The sub-sampled chunks of 3D testing image data with a label associated with one or more structures can be referred to as a first (second and so on) set of testing images showing a first (second and so on) region from the first set of 3D images. Similarly, the chunks sub-sampled from the unlabeled 3D image data can be referred to as a first (second and so on) set of testing images showing the first (second and so on) region from the second set of 3D images For example training procedure 655 in FIG. 6 and the model obtained in the form of the transform function $f_1$ can be validated in the evaluation procedure 657 by comparing the generated image data $f(X_{test})$ 656 to $Y_{test}$ data 654.

Figure 7A:
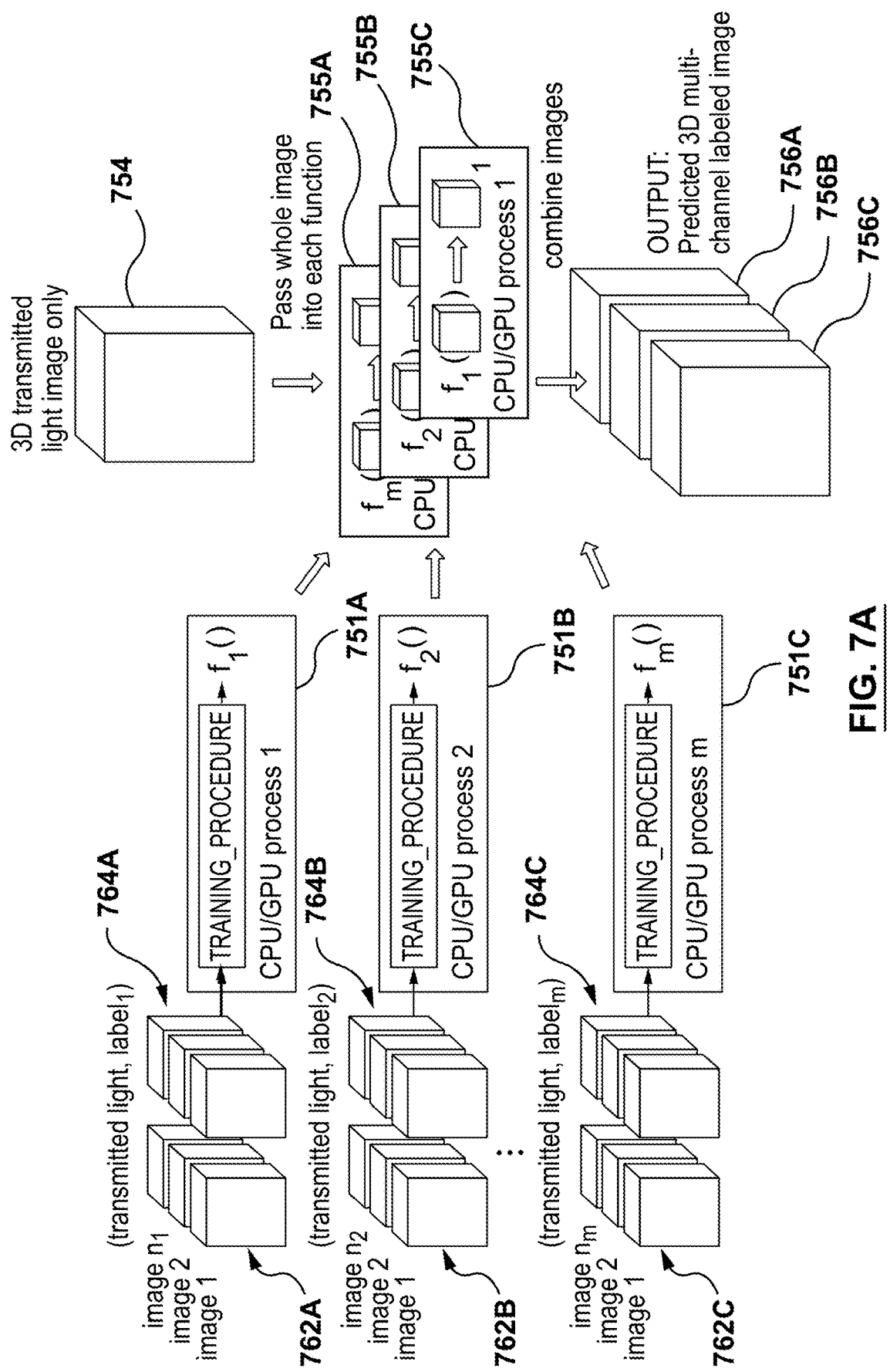
FIG. 7A is an illustrative example of a proposed use case for applying image analysis aspects disclosed herein over multiple labelled imaging data sets, according to an embodiment.
Figure 7B:
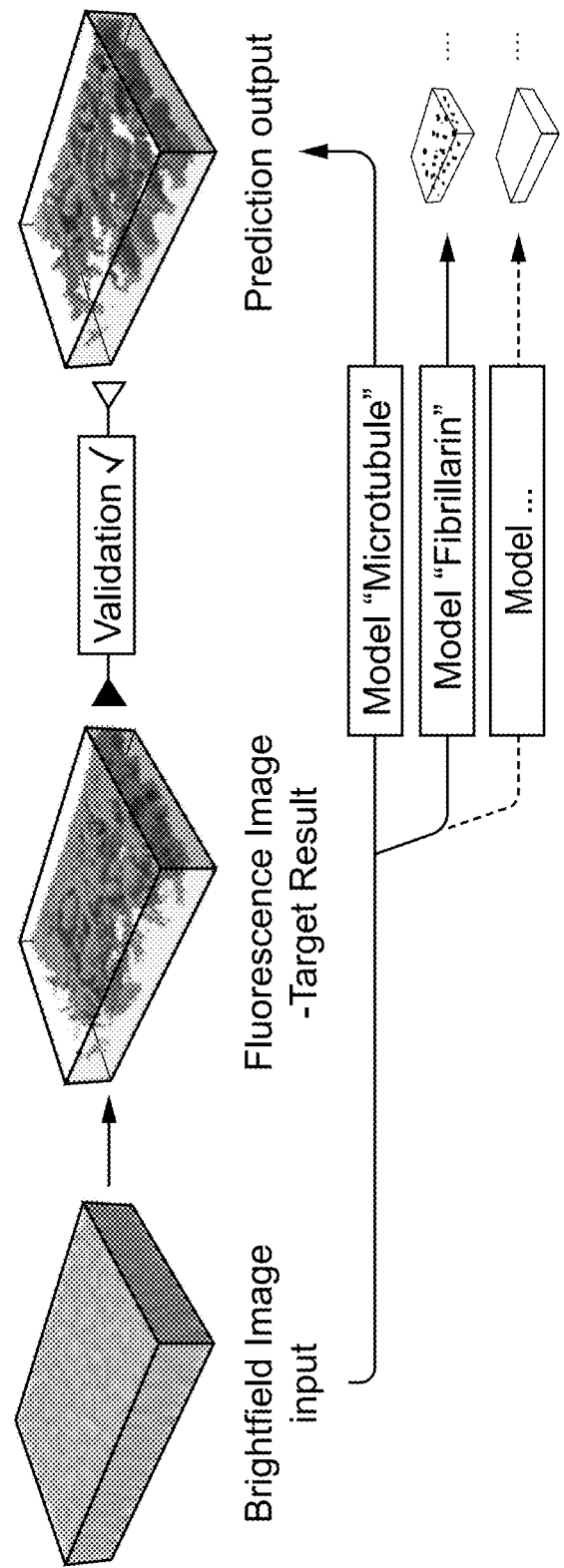
FIG. 7B is an illustrative example of validation of a predicted output, according to an embodiment.

FIG. 7A illustrates an example method to perform predictive localization using data containing several sets of three dimensional stacks (set 764A, set 764B, set 764C), each set containing image stacks with different labeling (A, B, and C). The image stacks from each differently labeled or unlabeled set can be paired with an image stack acquired through transmitted light imaging (set 762A, set 762B, set 762C) that can be used for training purposes. Additionally, a new unlabeled data (754) is to be reconstructed by predicting labelled images from the given unlabeled, transmitted light data 754, based on models built with the training data set. Input data for training is represented by cubes containing three dimensional image stacks of n regions (e.g., n=1, 2, etc.), imaged with m different labels (e.g., m=A, B, C, etc.). Each labeled 3D image stacks (e.g., 764A) can then be an example of a first set of 3D images of the plurality of sets of 3D images. Each labelled image stack can be paired with a corresponding unlabeled, transmitted light data stack (e.g., 762A), also referred to as a second set of 3D images of the plurality of sets of 3D images. The paired data can be fed into a training procedure similar to that described herein, where statistical models can be built to best estimate the relationship between the paired labelled and unlabeled training data sets (A, B and C pairs of unlabeled data 762 and labeled data 764). In this example, all the input data can be used as training data set, or a sub set can be randomly assigned to be testing data set for validation, wherein the validation is illustrated in FIG. 7B. In the example of FIG. 7B, a plurality of models may been trained for different respective labels. Each label (e.g., label 1 indicated by A, 2 by B, . . . m) can target one or more different substructures and therefore the training procedures 751A, 751B, and 751C for example, can arrive at a best estimated transform function for each label (e.g., $f_1$ for label1 (A), $f_2$ for label2 (B) . . . and $f_m$ for label m (C)).

In order to predict localization of structures by predicting labels in the three dimensional transmitted light only data set 754, also referred to as a third set of 3D images of the plurality of sets of 3D images, the transform functions resulting from the training procedures 751A, 751B, and 751C, are applied on the transmitted light data 754, at steps 755A, 755B, and 755C. This application is carried out by passing the unlabeled transmitted light data through each transform function sequentially and then combining (e.g., overlaying) the resulting prediction images. The output image stacks 756A, 756B, and 756C, are thus three dimensional image stacks with as many channels of predicted labelling as there are labels in the training data set or as many transform functions that can be learned through statistical models using the training data set. The output image stacks 756A, 756B, and 756C, can each be an example of a fourth set of 3D images.

In an embodiment, the steps discussed above can be performed with cell structures such as some membranous structures and larger aggregates (e.g., nucleoli, endoplasmic reticulum, mitochondria, DNA), but are more difficult with cell structures with low-contrast, such as desmosomes and actomyosin bundles.

Figure 8:
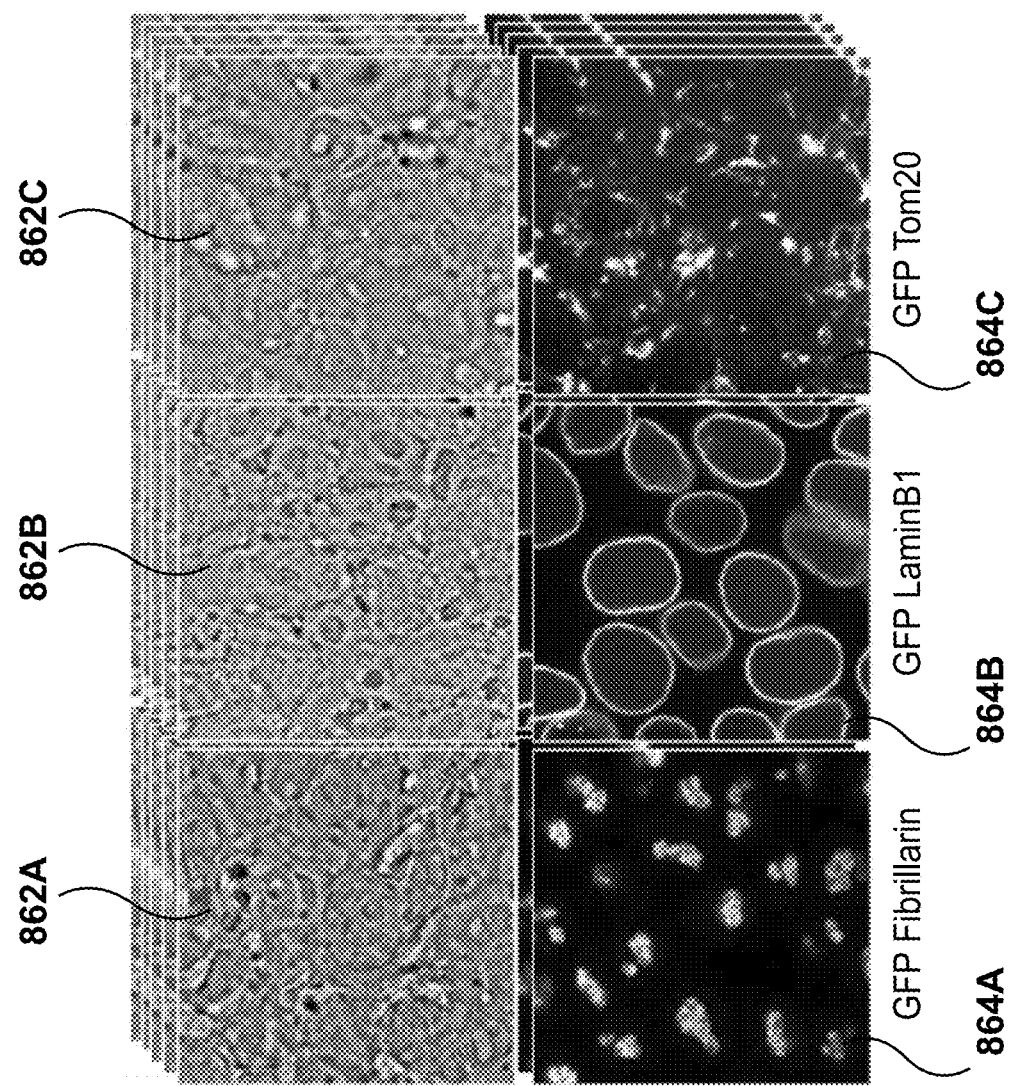
FIG. 8 is an example training data set used to predict localization of cellular structures.

FIG. 8 shows an example input data set similar to the input data set illustrated in FIG. 7A. The training data set in the example in FIG. 8 includes pairs of three dimensional image stacks (A, B and C) each pair consisting of one image stack obtained through transmitted light imaging (e.g., stacks 862A, 862B, and 862C) and the other corresponding labelled image stack obtained through fluorescence imaging (e.g., 864A, 864B, and 864C), with a specific fluorescent tag. For example, the first pair of image stacks contains a transmitted light image stack 862A and a fluorescence image stack, 864A, labelled with Fibrillarin. In this example, Fibrillarin, a nucleolar marker, is tagged using a green fluorescent protein (GFP) highlighting the localization of nucleolar structures in the cells. The image stack 864A with the Fibrillarin labeling is an example of a first set of 3D images as disclosed herein, and the image stack 862A with transmitted light images can be an example of a second set of 3D images. Similarly, the second and third pairs of training data set include a transmitted light image stack each, 862B and 862C, and a fluorescence image stack, 864B, labelled with LaminB1, a nuclear envelope marker, in the second and a fluorescence image stack, 864C, labelled with Tom20, a mitochondrial marker, in the third. This data set of paired labelled and unlabeled image stacks can be used by a system to learn and generate statistical models to predict nucleolar labelling using Fibrillarin, nuclear envelope labelling using LaminB1, and mitochondrial labelling using Tom20, when tested with an unlabeled data set obtained through transmitted light imaging.

Figure 9:
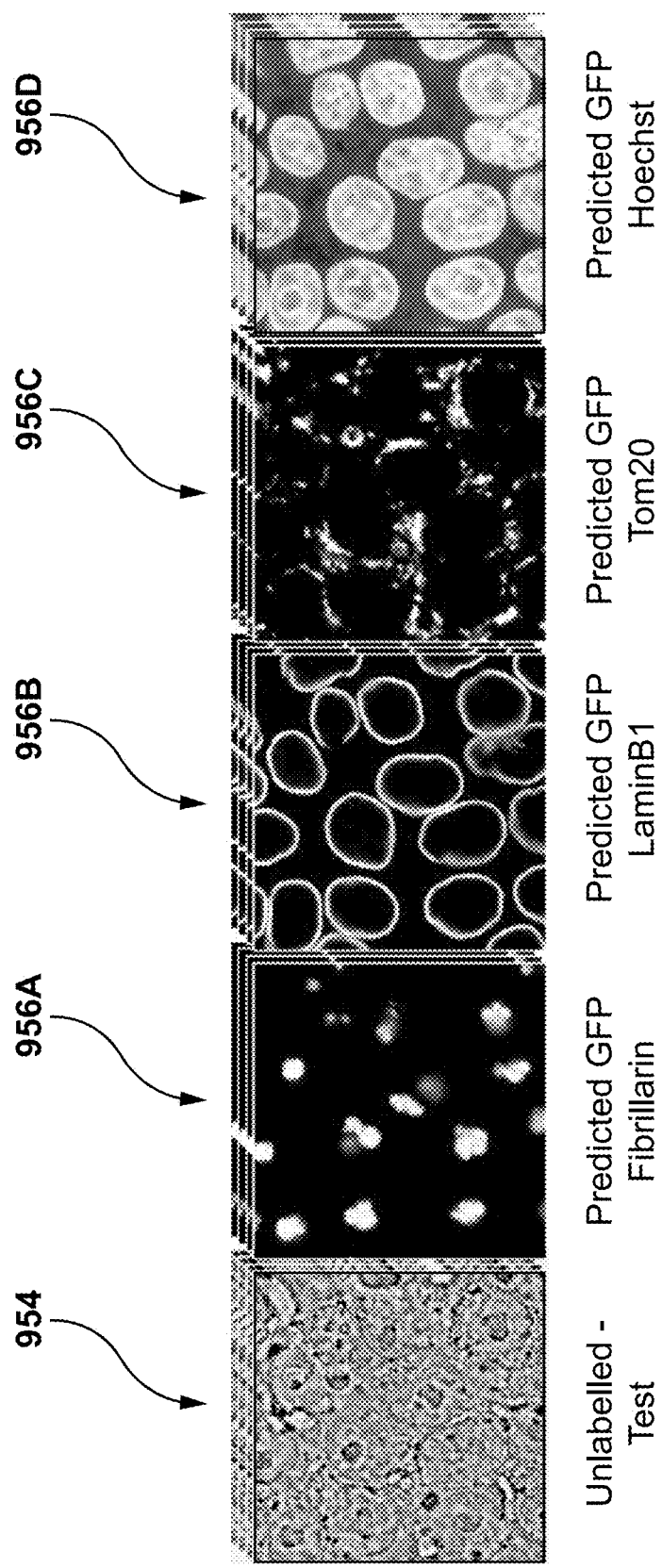
FIG. 9 is an example set of predicted image data resulting from predictive localization of cellular structures, using one embodiment.

FIG. 9 shows an example result from predictive localization of several cellular structures through prediction of fluorescence labelling of each. To obtain the results shown in FIG. 9 a system was trained using pairs of labelled and unlabeled three dimensional image stacks such as shown in FIG. 8. Specifically, the system was trained using training data sets that had fluorescence data with nucleolar labelling using Fibrillarin (A), nuclear envelope labelling using LaminB1 (B), mitochondrial labelling using Toom20 (C), and DNA labelling using Hoechst (D) fluorescent markers. Following training the system was tested with a new unlabeled data set for predictive localization of the four labels used in training. FIG. 9 shows example slices or other portions of the unlabeled testing data set, 954, and example slices (956A, 956B, 956C and 956D) of the predicted fluorescence labeling for the four markers used in training. In some cases, the processor may generate image 956A by predicting a greyscale intensity for each pixel in the unlabeled image 954, wherein the greyscale intensity is associated with presence or amount of a Fibrillarin marker that binds to the nucleolar structures. The processor may employ a similar process to generate images 956B, 956C, and 956D associated with LaminB1, Tom20, and Hoechst, respectively.

Figure 10A:
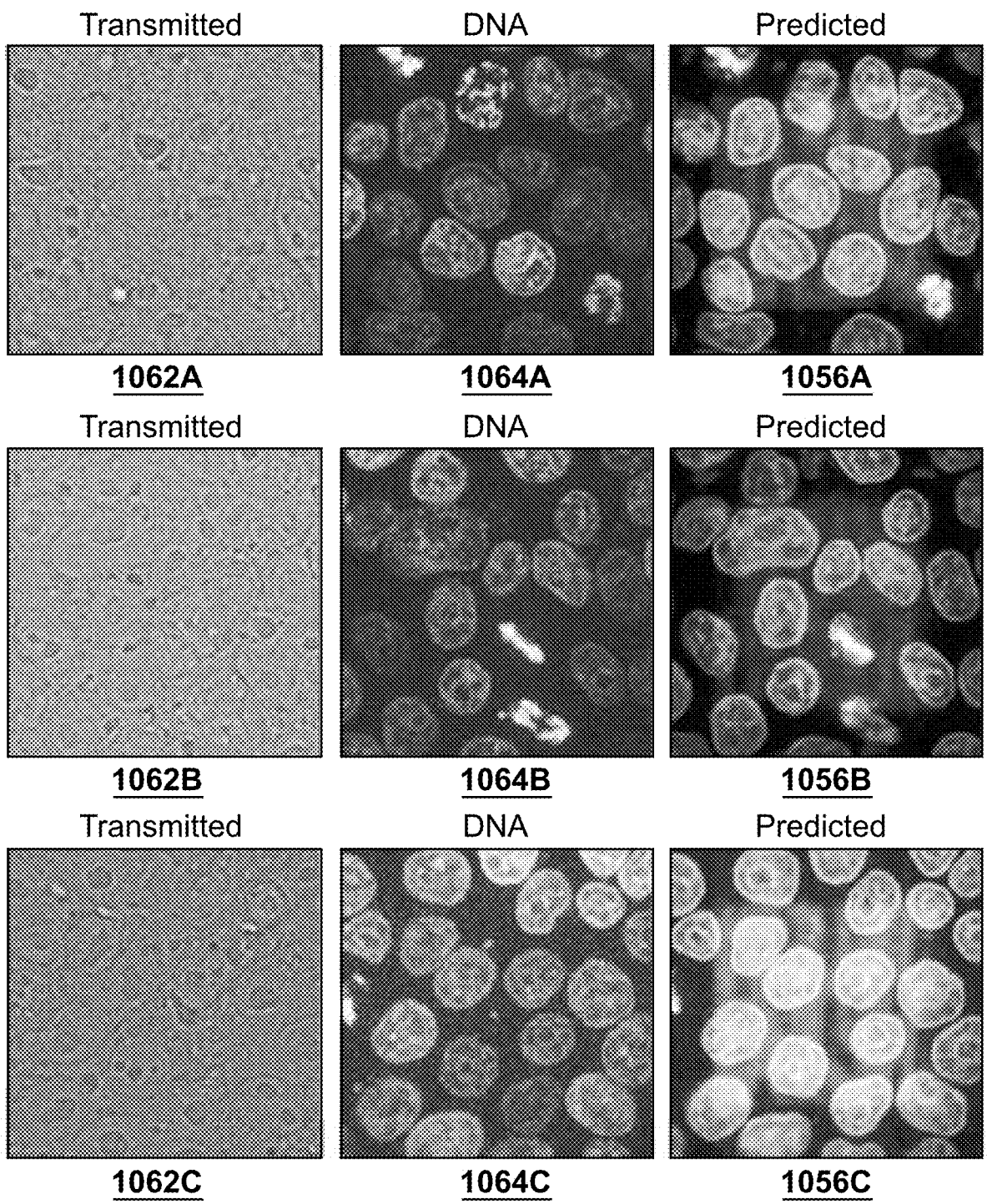
FIG. 10A is an example set of image data showing unlabeled, true labeled, and predicted label images, according to an embodiment.
Figure 10B:
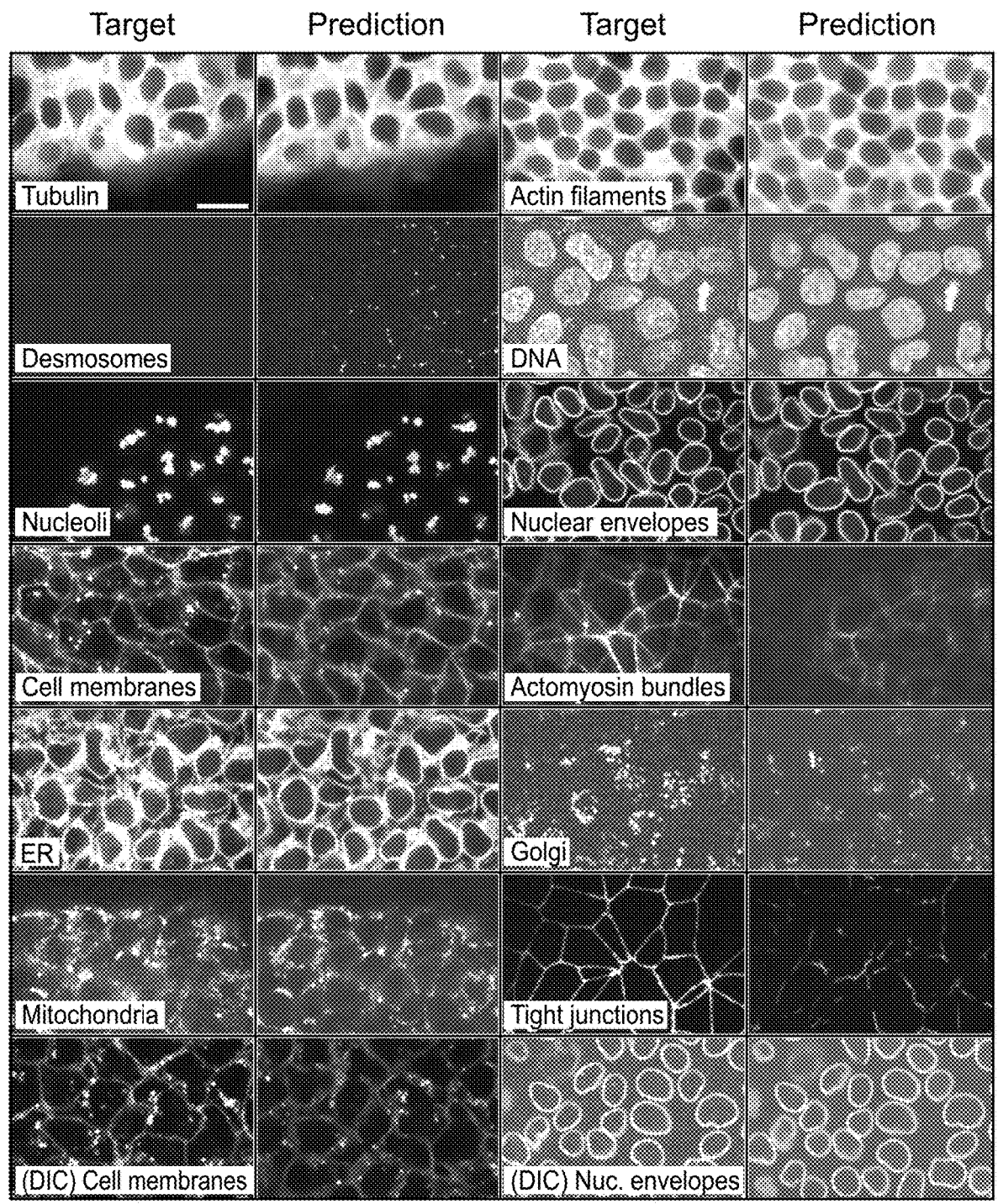
FIG. 10B is an example set of image data showing unlabeled, true labeled, and predicted label images, according to an embodiment.
Figure 11A:
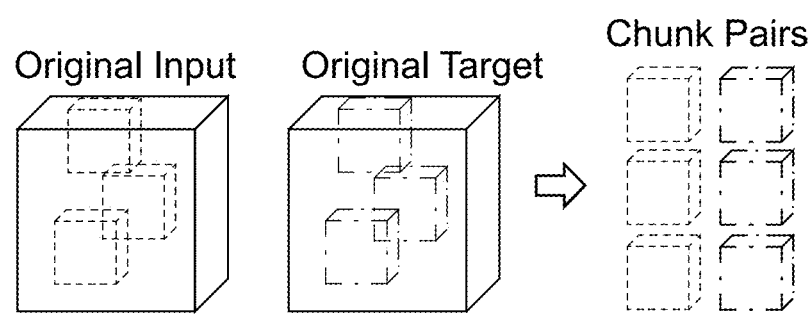
FIG. 11A shows an example implementation of predictive localization of cellular structures from three dimensional volume pairs of labeled and unlabeled image stacks through the use of sub-sampling, according to one embodiment.
Figure 11B:
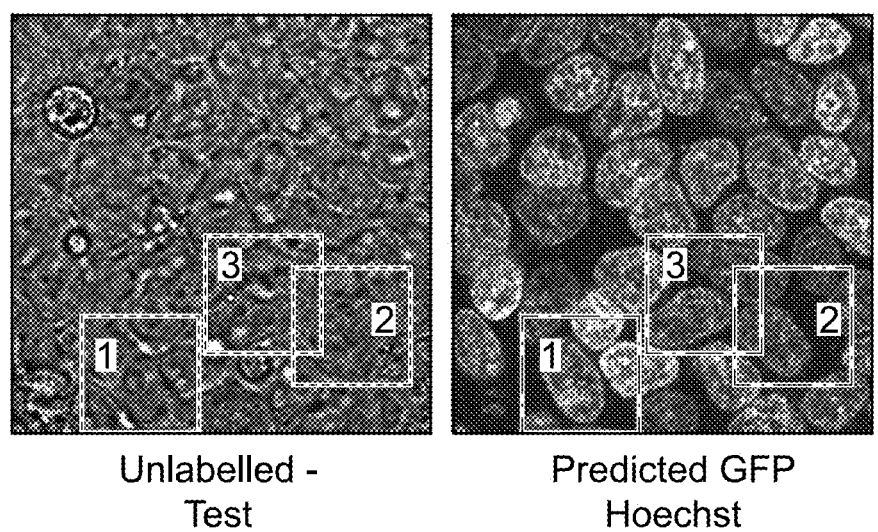
FIG. 11B illustrates an example unlabeled portion (e.g., region) of the sample and the corresponding predicted localization of structures, highlighting three sub-sampled regions used for training and prediction, according to one embodiment.
Figure 11C:
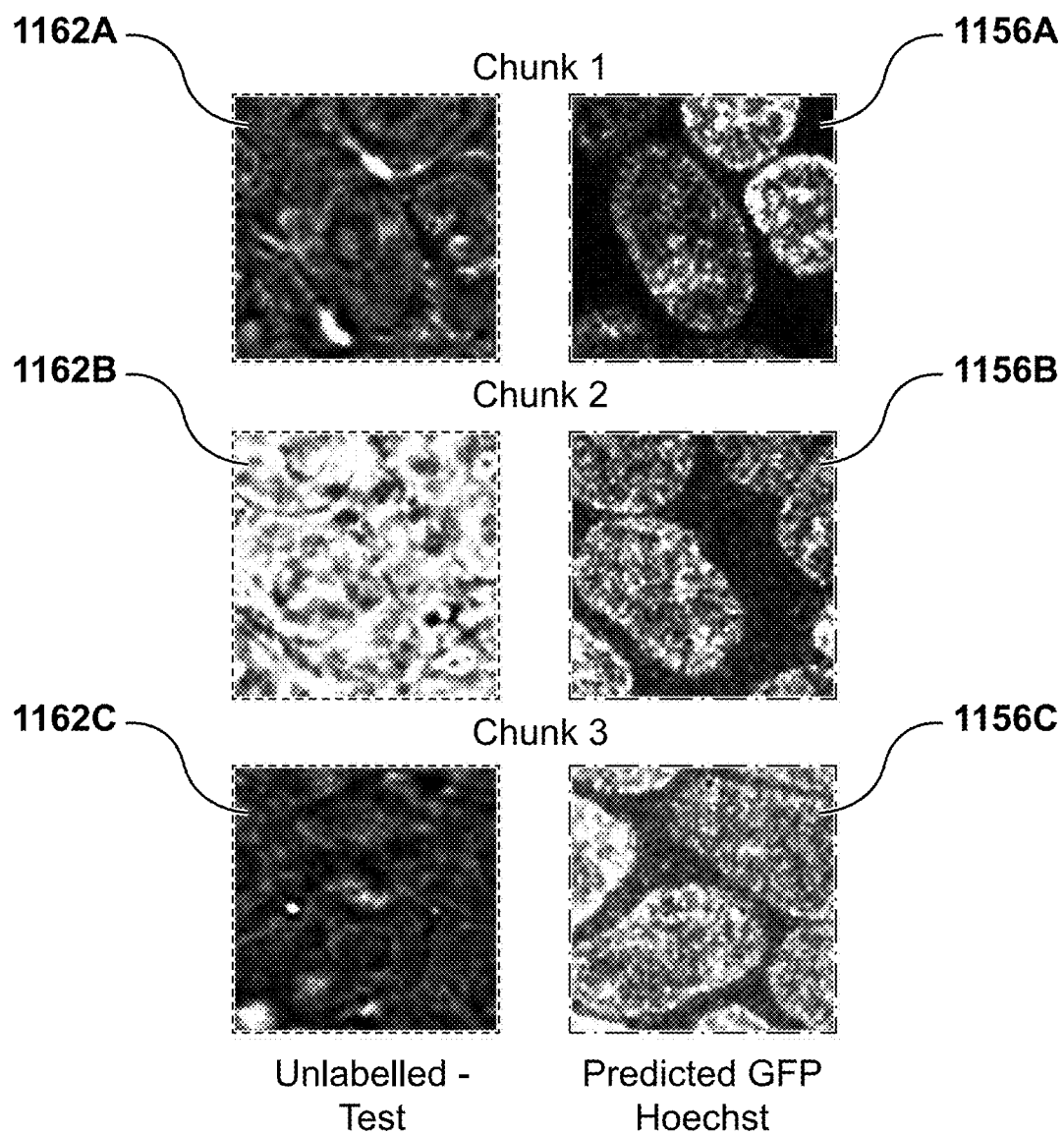
FIG. 11C illustrates the three highlighted sub-sampled regions from FIG. 11B, juxtaposing each unlabeled portions alongside the predicted labeling.

FIG. 10A shows an example set of three test images, 1062A, 1062B, and 1062C, obtained using transmitted light imaging and tested for predictive localization of DNA labeling. The true fluorescence labeled images, 1064A, 1064B, and 1064C, show localization of DNA bound by the Hoechst dye. The predicted labeling of DNA is shown in images 1056A, 1056B, and 1056C predicted using an embodiment of system 100. These high correlation between the true labeled images and the predicted labeling in the results indicate the high accuracy of predictive localization using the 3D-IMTsystem. FIG. 11A shows an example use of an embodiment of the system 100 to perform predictive localization in a large image dataset. As described above, when the training and/or testing image data sets are too large to be handles in their entirety, training and testing can be performed by sub-sampling the data sets into chunks of over lapping or non-overlapping sub-image stacks. The example shown in FIG. 11C illustrates three sub-sampled chunks 1162A, 1162V, and 1162C, (highlighted in FIG. 11B) of the unlabeled testing data set and the corresponding chunks 1156A, 1156B, and 1156C, of the corresponding predicted labeled data. FIG. 10B shows a similar comparison of true fluorescence labeled images and of predicted fluorescence images. More specifically, the figure shows additional labeled structure models and predictions for 3D light microscopy. For each model, a single z-slice of a ground-truth (observed) fluorescence image is shown beside an image predicted by a labeled structure model, given the corresponding 3D transmitted light image as input (latter not shown). All models use bright-field images as inputs except for models shown in the last row, which were trained on DIC images. Z-slices were chosen in a curated fashion to highlight the structure of interest associated with each model. Image-slice pairs were identically contrast stretched, such that black and white values corresponded to the 0.1 and 99.9th percentiles of the target image intensity, respectively. All images shown are independent from model training data. The scale bar is 20 micron.

Figure 10C:
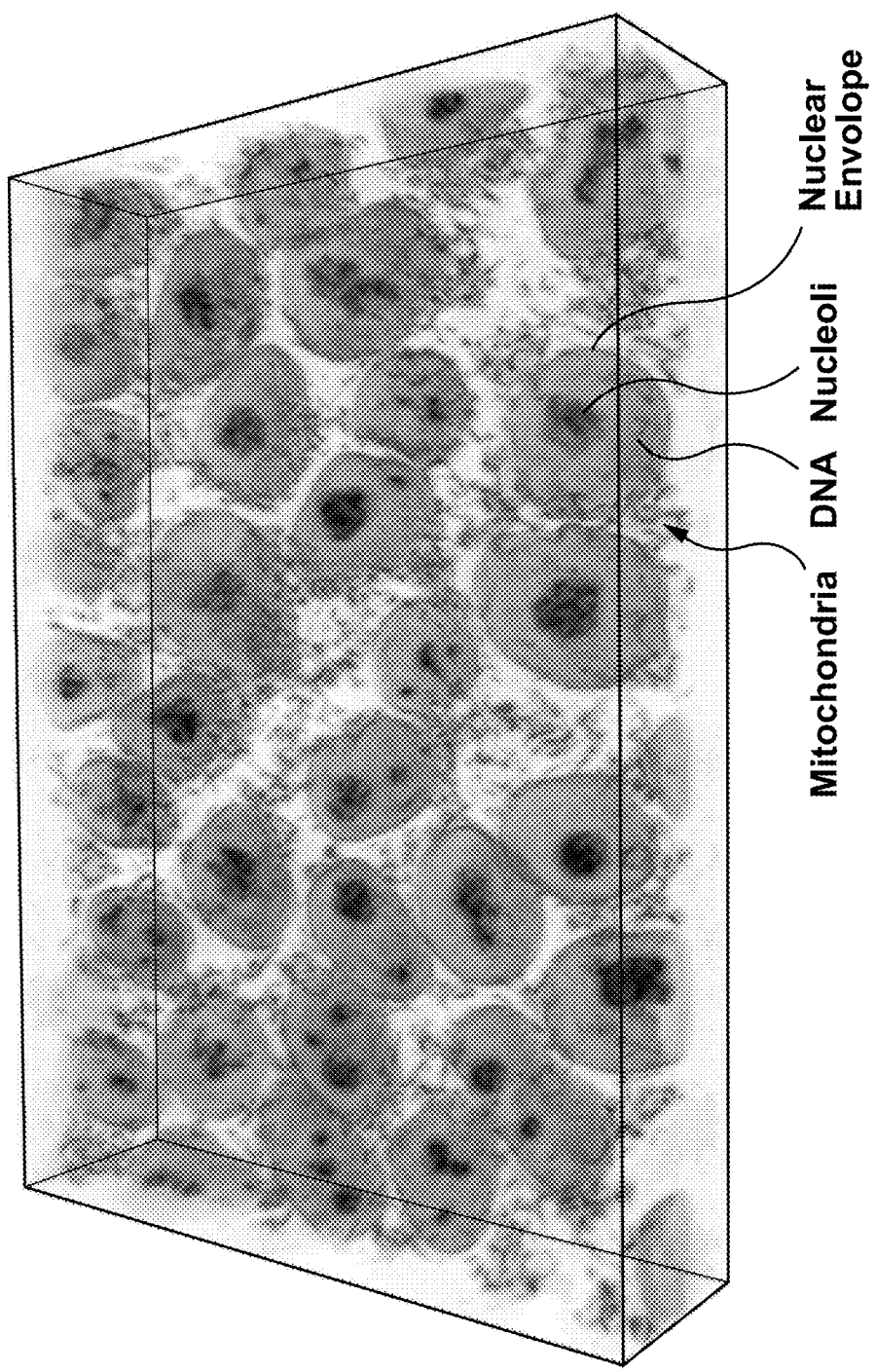
FIG. 10C illustrates exemplary results for 3D rendering of light microscopy images.

FIG. 10C illustrates prediction results for 3D rendering of images obtained with light microscopy. The figure illustrates the relationship between 3D time lapse transmitted light in-put and multiple prediction images. First, individual z-plane images from a 3D transmitted light are shown in succession. Next, individual predictions are shown overlaid in color in the following order: DNA (blue), nucleoli (magenta), nuclear membrane (yellow) and mitochondria (green). Next, a composite rendering of all channels is shown, followed by a volumetric 3D rendering of all predictions, together. Finally, the same volumetric 3D rendering of individual time points or time instances from the time series shown in FIG. 17E is shown and repeated 4 times. The boxed outline depicts the extent of the field of view of this volume which encompasses 97 μm×65 μm×19 μm.

Figure 12:
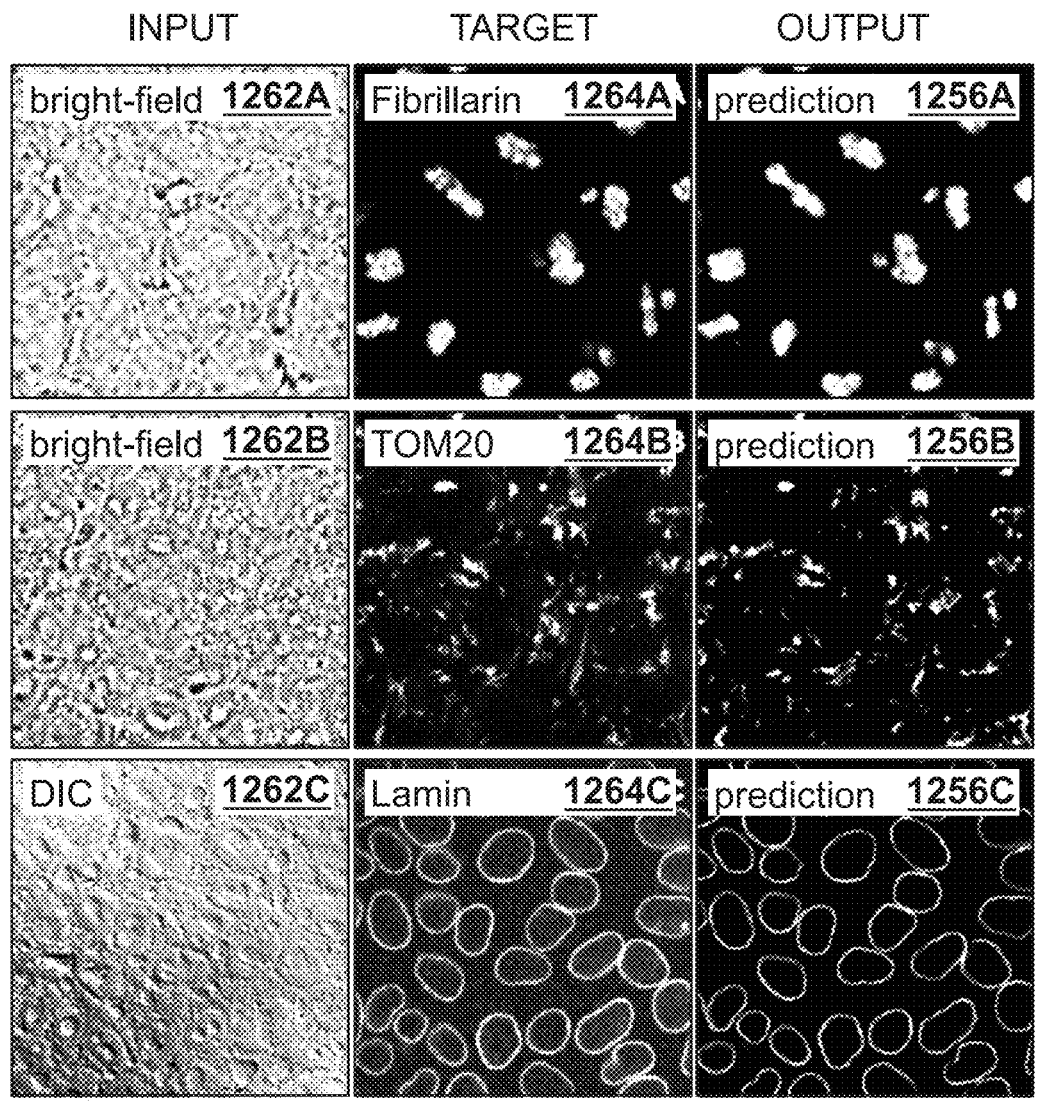
FIG. 12 illustrates three example portions of unlabeled sample, the corresponding portions with true (target) labeling, and the predicted (output) labeling from predictive localization according to an embodiment.

FIG. 12 illustrates example results from the predictive localization of several structures with distinct labeling. The labeled images 1264A, 1264B, and 1264C are example target portions of a set of cells labeled with Fibrillarin (targeting nucleolar structures), Tom20 (mitochondrial structures), and Lamin (targeting nuclear envelope), respectively. Unlabeled images 1262A, 1262B, and 1262C, are the corresponding input portions captured with transmitted light imaging from which the structures are to be localized through predictions made by a trained statistical model. Images 1256A, 1256B, and 1256C are the corresponding output portions with predicted labeling to compare with the target portions.

Figure 13A:
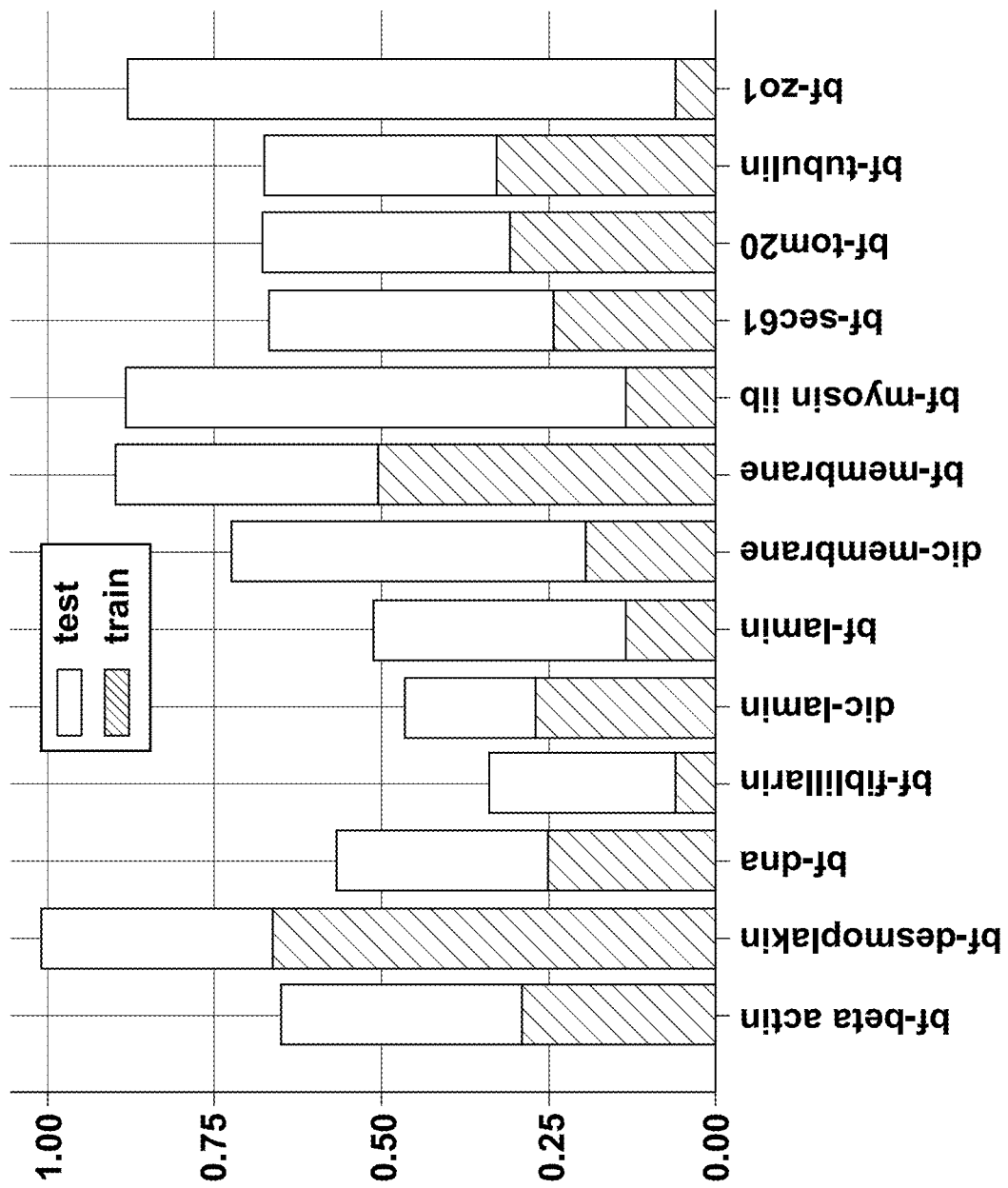
FIGS. 13A and 13B illustrate plots of the quantified loss function during the training and prediction of localization of a variety of sub-cellular structures, according to some embodiments.
Figure 13B:
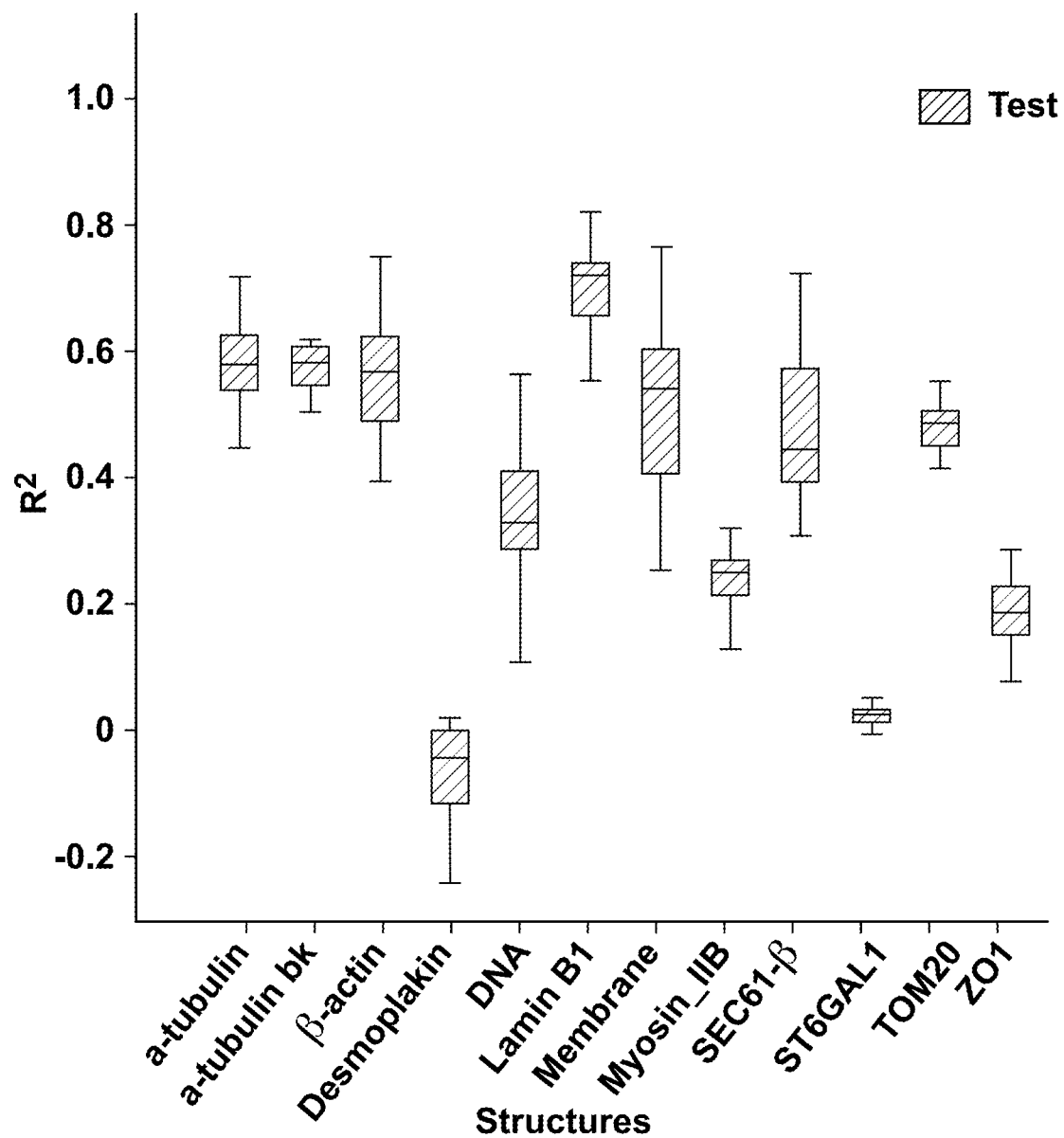

FIG. 13A is a bar plot illustrating the performance of an embodiment of an example system (e.g., similar to the system 100) at predictive localization of several sub-cellular structures with distinct labels like beta actin, desmoplankin, DNA, etc. The bar plot in FIG. 13A shows a normalized quantification of the loss function computed on data split into testing data set (dark colored portions of bars) and training data set (light colored portions of bars). FIG. 13B further illustrates quantified performance of some example models. More specifically, the figure depicts correlation coefficients between predicted images and target images (e.g., labeled images) for certain structures. In some embodiments, model performance may have an upper bound that is based on an estimate of signal-to-noise ratio (SNR) of target images. As stated above, in some cases the performance of the trained models may be improved if the trained models are applied to input images that were acquired with the same parameters or other conditions used to acquire the training images. For instance, the trained models may have improved performance if they are applied to input images (e.g., bright field images) that were acquired with an inter-slice interval that is equal to or longer than the inter-slice interval used to acquire the training images. Thus, in an embodiment, new images that use the trained model for predictive labelling can be acquired with parameter values or other conditions that are the same as those used for acquiring the training images.

In an embodiment, performance of the models and their predictions may take into account global image complexity. More specifically, some intracellular structures are more complex than others, and the evaluation of performance may take into account such a variation. In one example, an approximation of the Kolmogorov complexity may be used. More specifically, the Kolmogorov complexity may be approximated by the minimum file size (or, more generally, memory size) of an image given spatially-aware lossless compression. For instance, this approximation may yield a single number, such as a conditional entropy, that represents how difficult an image of a particular structure is to recapitulate. In one example, this number can be calculated as a first image file size minus a second image file size, wherein the first image file size is a file size of an image having the cellular structure (e.g., having the nucleus, cell membrane, and the cellular structure of interest), and the second image file size is a file size of an image not having the cellular structure (e.g., having the nucleus, cell membrane, and not having the cellular structure of interest).

Figure 14A:
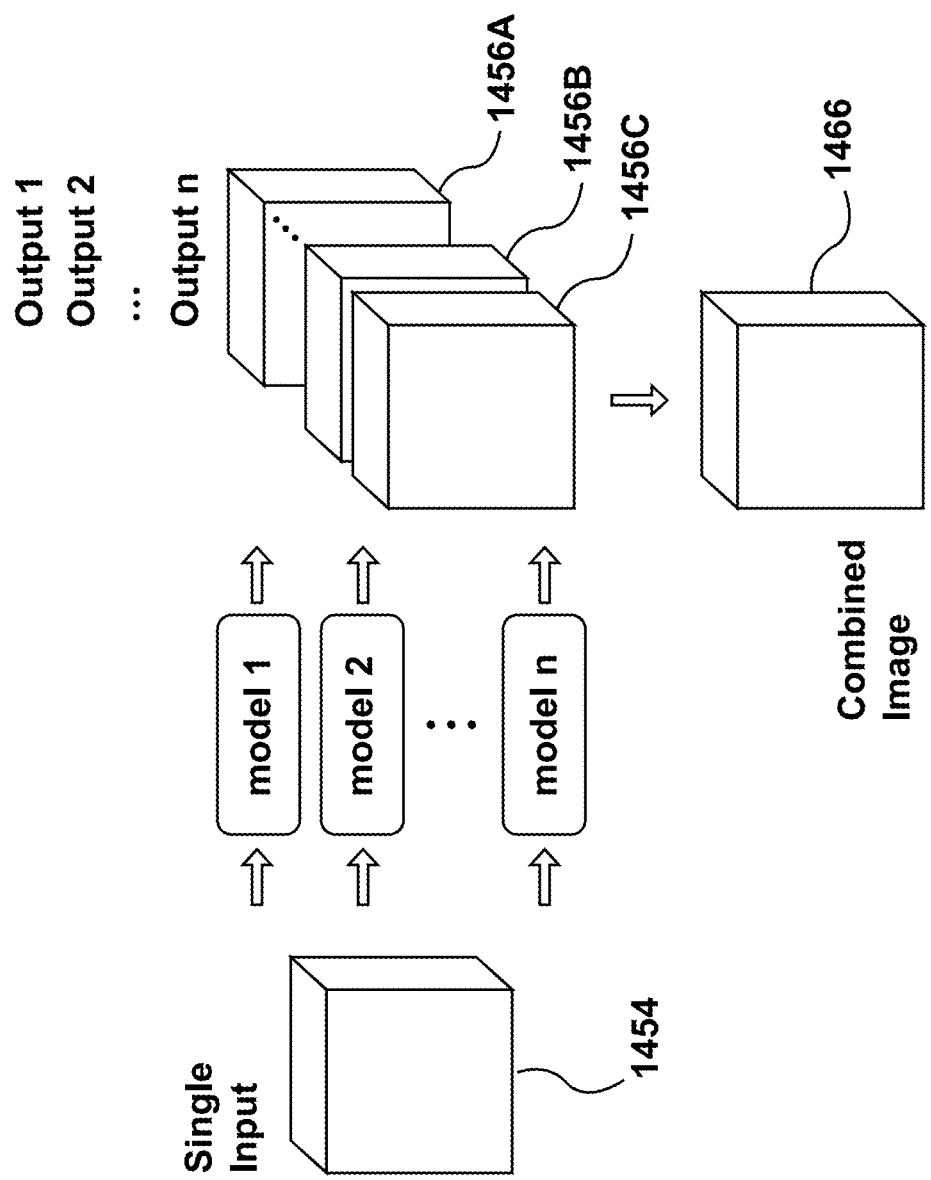
FIG. 14A is an example of an illustrative schematic of predictive localization of several sub-cellular structures and the combined representation of the predicted output, according to an embodiment.
Figure 14B:
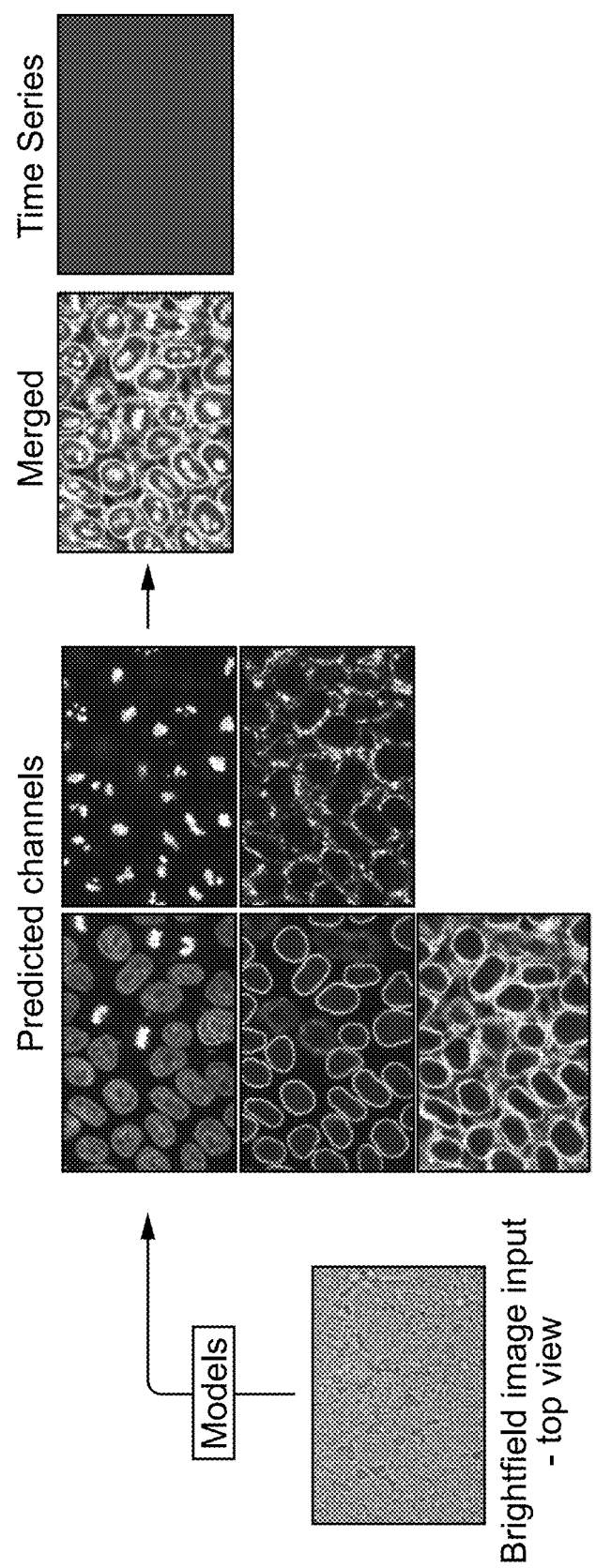
FIG. 14B is an example of a combined representation of predicted output, according to an embodiment.

FIG. 14A illustrates a scheme to predict the localization of several structures (1, 2, ... n), such as cell membrane, nucleolar, and DNA, using an embodiment of the system 100. The scheme can train several statistical models (model1, model2, ... model n). For instance, the scheme can train at least three statistical models corresponding to labeling for cell membrane, labeling for nucleolar, and labeling for DNA, respectively. A processor may use an unlabeled 3D image, such as input image 1454, to predict localization of the structures, such as by predicting which portions on the image will be labeled as a cell membrane, which portions on the image will be labeled as a nucleolar, and which portion will be labeled DNA. The predictions can be in the form of predicted outputs 1456A, 1456B, and 1456C (output 1, output 2, ... output n, respectively). The output stacks 1456A, 1456B, and 1456C, each labeling one or more structures, can also be visualized through a combined image or image stack 1466. The combined image or image stack 1966 can be generated by merging the outputs, 1456A, 1456B, and 1456C, each labeled with a distinct spectral line. For instance, FIG. 14A illustrates a situation in which five different models can generate five different respective predicted images from a single unlabeled bright-field image. The five different predicted images can correspond to five different structures, and may be referred to as five different channels. FIG. 14A depicts a merged image that merges the five different images into one image. The merged image can show all five of the structures. In some cases, if a time series of merged images may be generated from a time series of unlabeled bright-field images. FIG. 14B similarly illustrates an embodiment in which, e.g., five different models can be applied to a bright field image to generate five respective labeled images, wherein each labeled image can include predictive labeling for a different respective cellular structure. In the embodiment of FIG. 14B, the predictive labeling in the five images can have five different respective colors, and the five images can be merged into a single image that shows labeled cellular structures from each of the five images. In an embodiment, the models can also be used to generate a time series, in a manner similar to that described in FIG. 3B.

Figure 15:
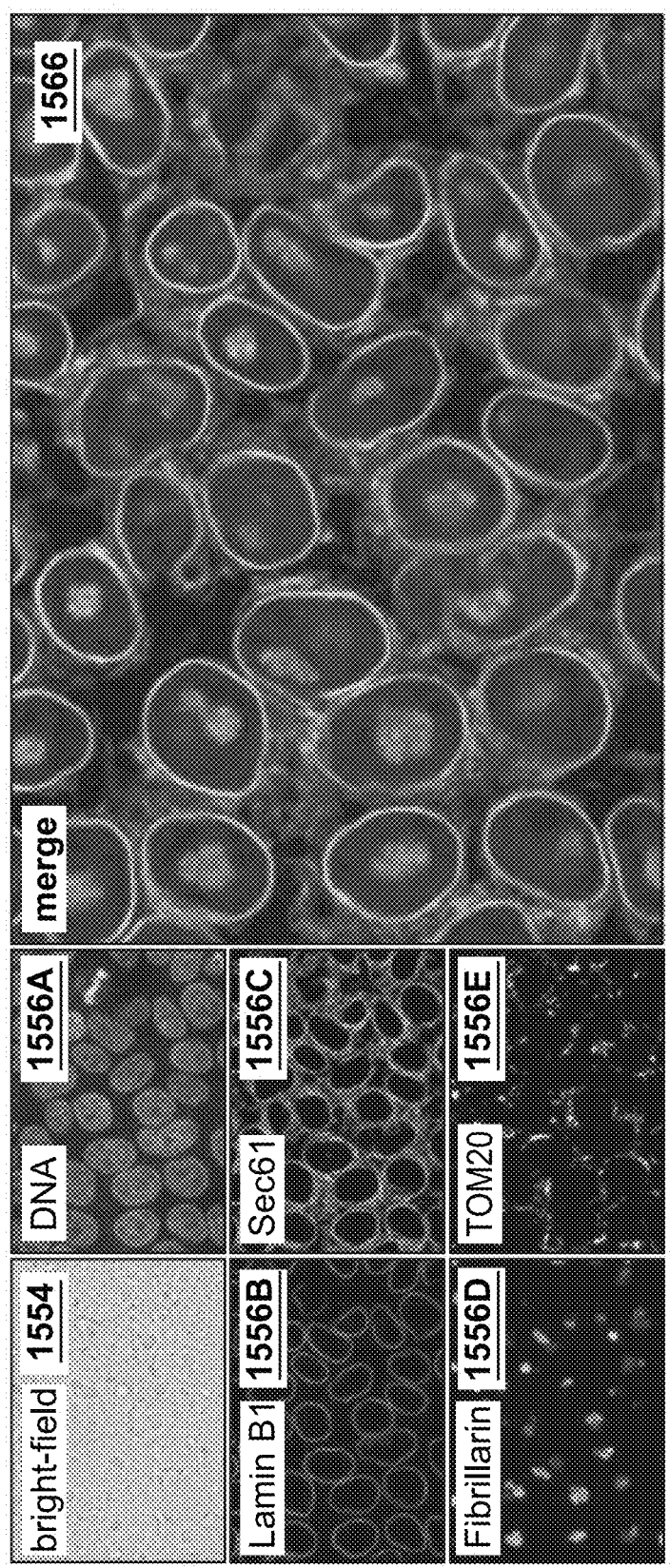
FIG. 15 illustrates an example unlabeled portion of a sample used to predict the localization of five different sub-cellular structures using an embodiment of the system disclosed herein, and the combined representation of the results in a merged composite image.

FIG. 15 illustrates an example set of output images 1556A-1556E, each predicting the localization of structures though predicted labeling of markers, from the input image 1554 (collected though bright-field imaging). The combined image 1566 is generated from merging the output images 1556A-1556E.

In an embodiment, the training of the statistical model discussed herein can be used to perform image registration, and more particularly image registration in conjugate array tomography. Conjugate array tomography, which is discussed in more detail in "Mapping Synapses by Conjugate Light-Electron Array Tomography," by Collman et al. (the content of which is incorporated by reference in its entirety), can involve applying at least two imaging modalities to myelin basic proteins (MBP) in ultrathin brain slices, such as electron micrograph (EM) imaging and immunofluorescence (IF) imaging (or, more generally, fluorescence imaging). Thus, at least a pair of images may be generated for each slice, wherein the pair includes an EM image of the slice and a fluorescence image of that slice. These pair of images can, however, capture different portions of the slice (or, more generally, of the sample), and may have different scales or even orientations. For instance, FIGS. 16A and 16B illustrate an EM image 1607 that captures a first portion 1603 of a slice 1601, and a fluorescence image 1609 that captures a second portion 1605 of the slice 1601. The two images 1607 and 1609 can be referred as image tiles in FIGS. 16A and 16B, wherein each tile can have a fixed number of pixels (e.g., 500 pixels by 500 pixels). Because the two images can capture different portions and have different scales (e.g., different levels of magnification, such that they have different resolution), they may thus have to be registered with each other to determine how they can have the same alignment, orientation, and/or scale. The image registration can allow overlaying of the images, as illustrated in FIG. 16C. For instance, once the two images 1607 and 1609 are registered with each other in FIG. 16C, the registration can indicate that an upper left corner of the image 1607 (e.g., a coordinate of 0, 0 in the coordinate space of image 1607) corresponds with a portion of the image 1609 starting at coordinate (xi, yi) in the coordinate space of the image 1609. The registration can further indicate that image 1607 should be scaled to $1/10$ or some other fraction of the image 1609, and/or rotated relative to the image 1609.

In an embodiment, the techniques related to the image registration may allow an electron microscope to take a first EM image at a low level of magnification, so as to capture a large field of view. The image registration may allow the first EM image to be registered with a fluorescence image. The fluorescence image may include a colored region (or other high-contrast region) that identifies a region of interest. The information from the image registration may allow the electron microscope to locate and focus on the region of interest, and to take a second EM image at a higher level of magnification to zoom in on the region of interest. In some cases, the image registration between the first EM image and the fluorescence image may have an error level associated with the low level of magnification. In such cases, the image registration may be performed again between the second EM image and the fluorescence image. Because the second EM image was generated at a higher level of magnification, the image registration between the second EM image and the fluorescence image may yield a lower level of error, and thus produce more accurate image registration information.

The registration of an EM image with a fluorescence image for conjugate array tomography can pose a particular challenge because they are different types of images (and thus have no intensity relationship) and because they may have vastly different scales. For instance, a tile of an EM image may represent an area of 225 µm² of a brain slice, while a tile of an fluorescence image may represent an area of 40,000 µm², which is two orders of magnitude larger. Further, a data set may include thousands of such tiles. These properties have generally prevented image registration from being automated.

Figure 16E:
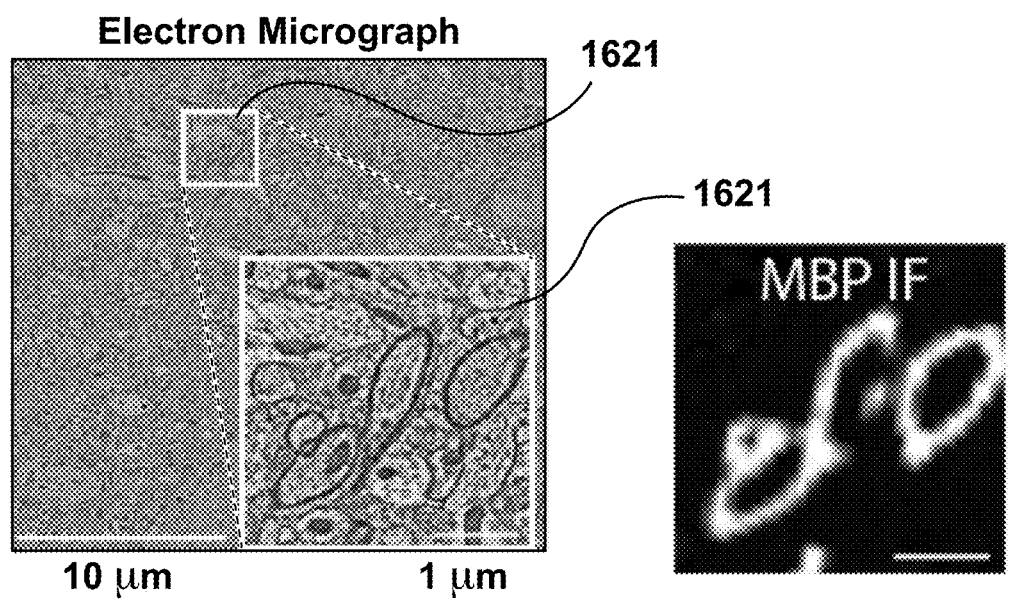

One aspect of the embodiments herein thus relate to providing a way to automate image registration of two images that were generated with two different respective imaging modalities, such as electron micrograph and immunofluorescence imaging. FIG. 16D illustrates example steps of a method for automating the image registration. In an embodiment, the method includes step 1611, in which a processor receives (e.g., via a communication interface) a first pair of images, wherein the first pair of images include a first image that is a fluorescence image of one or more cellular structures, and include a second image that is an electron micrograph (EM) image of the one or more cellular structures. For instance, FIG. 16E illustrates the first image being a fluorescence image that labels MBP in a brain slice, and the second image being an EM image of the brain slice. The first image and the second image may be registered with each other, such that they are aligned with each other and represent the same scale, or have associated registration information also received by the processor indicating how the first image and the second image can be aligned with each other. For instance, the registration information may indicate that the fluorescence image in FIG. 16E corresponds with the portion 1621 of the EM image. In an embodiment, the registration information may include a transformation matrix. In an embodiment, the first image and the second image may have been done manually, such as using TrakEM2. In one example, fluorescent imaging techniques may be applied to 50 ultrathin slices, using 3 rounds of staining and imaging to obtain 10 channel immunofluorescence data at 100 nm per pixel. In this example, 5 small regions can be imaged with a field emission scanning electron microscope to obtain high resolution electron micrographs at 3 nm per pixel. Image processing steps can stitch the immunofluorescence regions and one of the EM regions to create a 2D montage. Each EM montage can be manually registered to the corresponding montage of a myelin basic protein channel. For each montage pair, a central region (e.g., 2544 pixel×2352 pixel) may be cutout and used for training a statistical model.

Figure 16F:
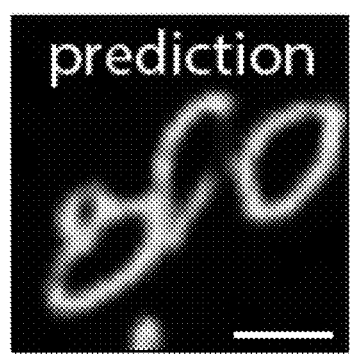

In step 1613, the processor can generate a statistical model to associate the one or more cellular structures in the first image with the one or more cellular structures in the second image. In an embodiment, this step can be the same or similar to steps 301-311. For instance, step 1613 can involve training a 2D convolutional U-net to be able to predict fluorescence labeling from the portion 1621 of the EM image. The training can involve, e.g., adjusting the kernel matrices of the linear filters until the prediction, such as the prediction in FIG. 16F, matches the fluorescence image in FIG. 16E.

The trained statistical model can be used to automate image registration between other pairs of an EM image and a fluorescence image. Those pairs of images may be of the same brain or other tissue on which the training was performed, or on another brain of piece of tissue. For instance, in step 1615, the processor may receive a second pair of images, wherein the second pair of images include a third image that is a fluorescence image, and a fourth image that is an EM image, wherein the third image and the fourth image are both of the one or more cellular structures used for training the statistical model, or of another one or more cellular structures, and wherein the third image and the fourth image are not registered with each other. For example, the right side of FIG. 16H depicts a third image that is a fluorescence image of a brain slice, and FIG. 16G depicts a fourth image that is an EM image of the brain slice.

In step 1616, the processor applies the trained statistical model to the fourth image generate an estimated fluorescence image of the fourth image. For instance, the left side of FIG. 16H illustrates an estimated fluorescence image (or, more generally, a predicted fluorescence image) that is generated by applying the trained statistical model to the EM image of FIG. 16G. In an embodiment, this step can involve downsampling the fourth image, such as a tile of the EM image, to 10 nm per pixel without any transformations to generate a 1500×1500 image. The downsampled image can then be padded, and the trained model can be applied to the padded image to generate a prediction image.

In step 1617, the processor determines registration information between the estimated fluorescence image and the third image. For instance, the processor can determine registration information between the image on the left side of FIG. 16H and the image on the right side of FIG. 16H, to determine how they correspond with each other. In this example, the registration information can indicate that the image on the left side of FIG. 16H corresponds with a portion 1631 of the image on the right side of FIG. 16H. In an embodiment, the step 1617 can use an intensity-based matching technique. For instance, step 1617 can involve the processor using a cross correlation based template matching to generate a rigid transformation estimate. The processor can then calculate a residual optical flow between a transformed image (in which the rigid estimate is applied to the predicted image) and the fluorescence image. The residual optical flow can then be used to fit a similarity transformation matrix that registers the transformed image and the fluorescence image. The same similarity transformation matrix can be used in step 1619 below to register the third image and the fourth image.

While the intensity-based matching technique in step 1617 can be done in an automated manner, it previously could not be used for a general situation involving an EM image and a fluorescence image, because they are two different types of images, and thus do not have a direct intensity relationship. The technique discussed herein can obtain such a direct intensity relationship, however, by using the trained statistical model to convert the EM image to an approximate fluorescence image. This conversion thus produces two images that are both fluorescence images, such that a direct intensity relationship between them can exist. As a result, an automated technique such as intensity-based matching can be performed to register the fluorescence image with the approximate fluorescence image. The result of this registration can be used to also register the EM image with the fluorescence image.

Figure 16I:
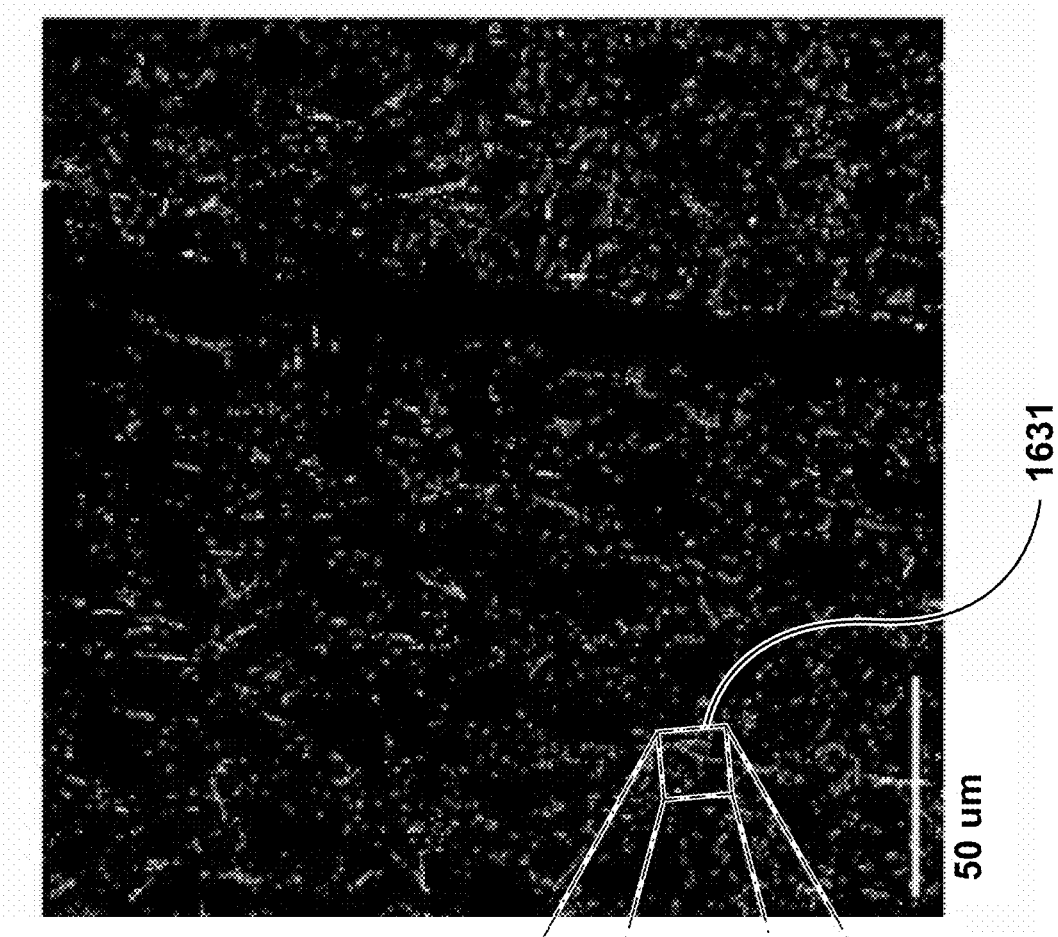
Figure 16I:
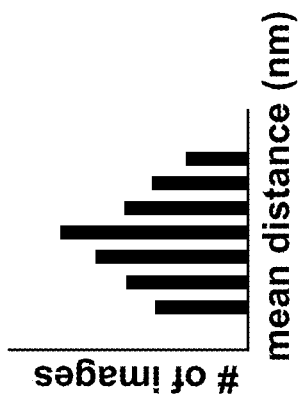
Figure 16I:
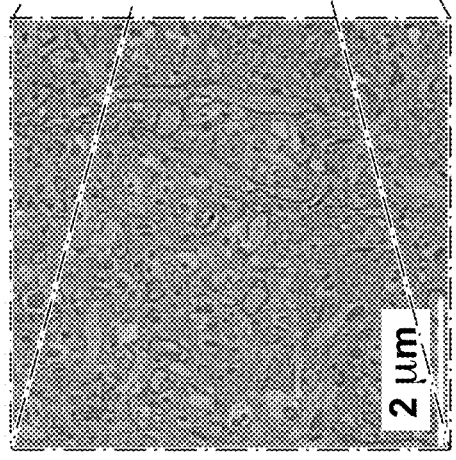

For instance, in step 1619, the processor registers the third image and the fourth image with each other based on the registration information. This step is illustrated in FIG. 16I, in which the processor can determine that the EM image of FIG. 16G also corresponds with the portion 1631 of the fluorescence image. In an embodiment, the EM image can then be overlaid on the portion 1631 of the fluorescence image, or vice versa.

In one experiment, the registration using the steps above was able to successfully register 86 of 90 image pairs with an error of 1.16+/−0.79 pixels. Thus, this technique allows an image processing pipeline developed with one imaging modality to be leveraged to process data collected in another imaging modality. For example, 3D cell segmentation can be developed based upon fluorescent membrane markers, and then applied directly to predictions.

Figure 16J:
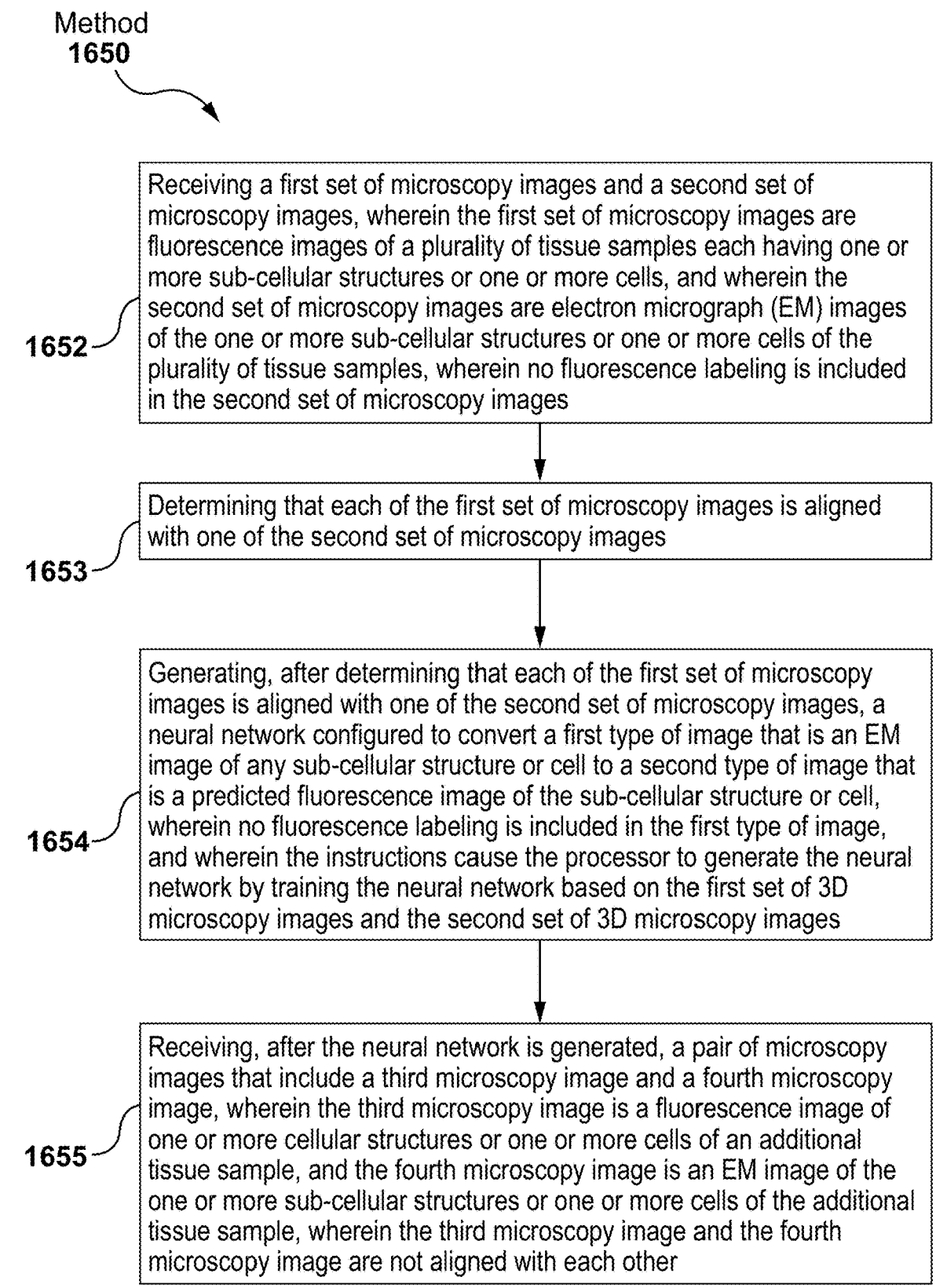
Figure 16K:
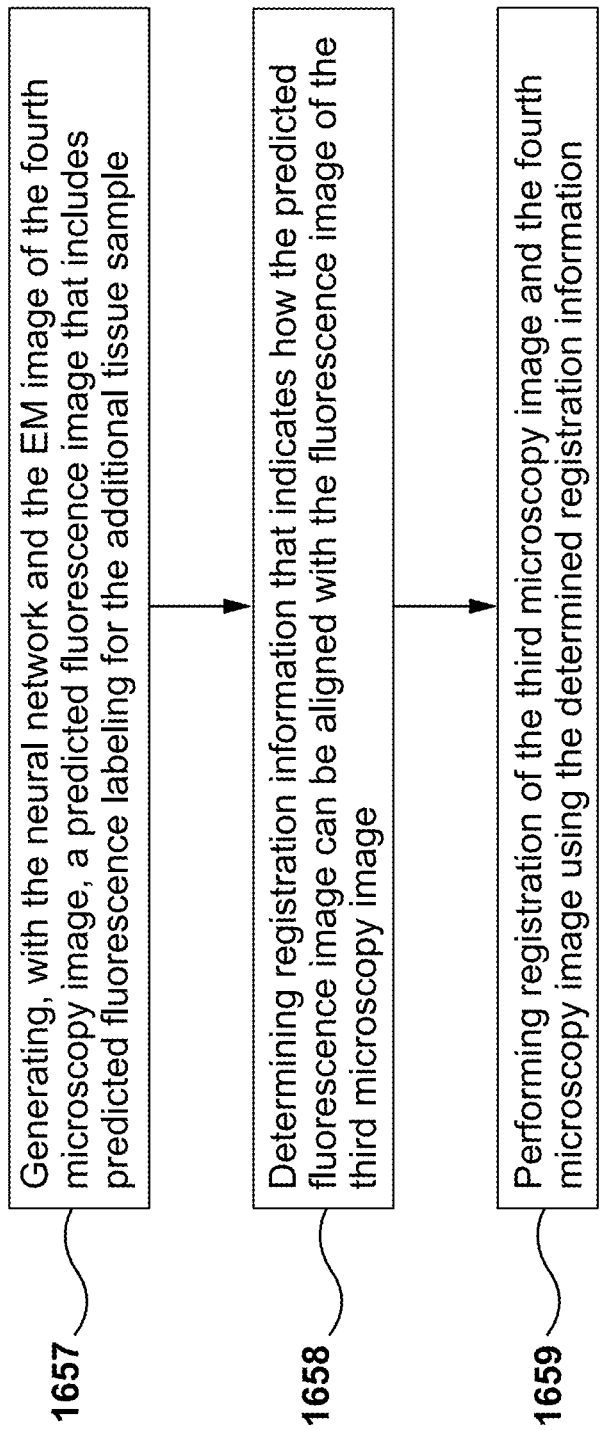

FIGS. 16J and 16K depict a flow diagram that presents another way of formulating the image registration discussed above. More specifically, the flow diagram illustrates a method 1650, which may be performed by a processor, such as a processor 120. In an embodiment, the method 1650 includes a step 1652, in which the processor receives, via the communication interface, a first set of microscopy images and a second set of microscopy images (e.g., a first and second set of 3D images), wherein the first set of microscopy images are fluorescence images (e.g., immunofluorescence images) of a plurality of tissue samples each having one or more sub-cellular structures or one or more cells, and wherein the second set of microscopy images are electron micrograph (EM) images of the one or more sub-cellular structures or one or more cells of the plurality of tissue samples, wherein no fluorescence labeling is included in the second set of microscopy images.

In step 1653, the processor may determine that each of the first set of microscopy images is aligned with one of the second set of microscopy images. In step 1653, the first set of microscopy images and the second set of microscopy images may have been in alignment when the processor received them, or the processor may receive image registration information between the two sets of microscopy images and perform image registration between them.

In step 1654, the processor generates, after determining that each of the first set of microscopy images is aligned with one of the second set of microscopy images, a neural network configured to convert a first type of image that is an EM image of any sub-cellular structure or cell to a second type of image that is a predicted fluorescence image of the sub-cellular structure or cell, wherein no fluorescence labeling is included in the first type of image.

The processor may generate the neural network by training the neural network based on the first set of 3D microscopy images and the second set of 3D microscopy images In step 1655, the processor receives, after the neural network is generated, a pair of microscopy images that include a third microscopy image and a fourth microscopy image, wherein the third microscopy image is a fluorescence image of one or more sub-cellular structures or one or more cells of an additional tissue sample, and the fourth microscopy image is an EM image of the one or more sub-cellular structures or one or more cells of the additional tissue sample, wherein the third microscopy image and the fourth microscopy image are not aligned with each other. In an embodiment, each pixel of the third microscopy image represents a bigger region of the additional tissue sample than does each pixel of the fourth microscopy image, such that the fluorescence image of the third microscopy image is at a lower level of magnification relative to the EM image of the fourth microscopy image. For instance, each pixel of the third microscopy image represents a region of the additional tissue sample that is at least 100 times larger than a region of the additional tissue sample represented by each pixel of the fourth microscopy image.

In step 1657, the processor generates, with the neural network and the EM image of the fourth microscopy image, a predicted fluorescence image that includes predicted fluorescence labeling for the additional tissue sample.

In step 1658, the processor determines registration information that indicates how the predicted fluorescence image can be aligned with the fluorescence image of the third microscopy image. For instance, the registration may be determined by using an intensity-based registration process that performs intensity matching between the predicted fluorescence image and the third microscopy image.

In step 1659, the processor performs registration of the third microscopy image and the fourth microscopy image using the determined registration information. For instance, the processor may perform registration by performing at least one of shifting, rotating, or scaling of the third microscopy image relative to the fourth microscopy image based on the registration information.

In an embodiment, the EM image of the third microscopy image was captured by an electron microscope at a first level of magnification of a first region of the additional tissue sample. The processor may control the electron microscope to acquire a fifth microscopy image of a second region that is a portion of the first region, wherein a location of the second region within the first region is indicated by the registration information, and wherein the fifth microscopy image is an EM image that is at a second level of magnification higher than the first level.

In an embodiment, the registration information is a first set of registration information, and wherein performing registration of the third microscopy image with the fourth microscopy image results in a first amount of alignment error between the third microscopy image and the fourth microscopy image. The processor may further generate, with the neural network and the fifth microscopy image, an additional predicted fluorescence image. The processor may further determine a second set of registration information that indicates how the additional predicted fluorescence image can be aligned with the fluorescence image of the third microscopy image, and perform registration of the third microscopy image and the fifth microscopy image using the second set of registration information. As stated above, performing the registration of the third microscopy image with the fifth microscopy image may result in a smaller amount of alignment error, relative to the first amount of alignment error, between the third microscopy image and the fifth microscopy image, because the fifth microscopy image is at a higher level of magnification (e.g., ten times the level of magnification of the third microscopy image).

Figure 17A:
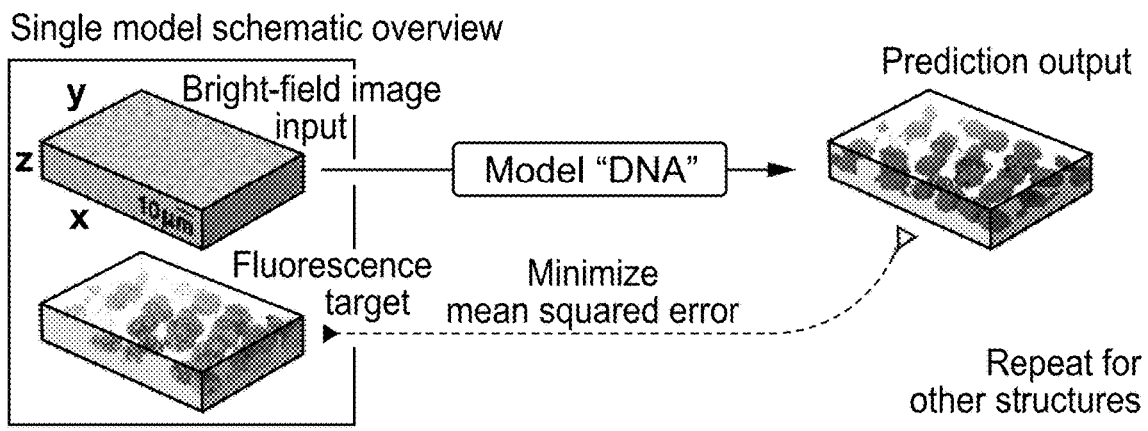
FIGS. 17A-17E illustrate an example of the imaging tool pipeline, according to an embodiment.
Figure 17B:
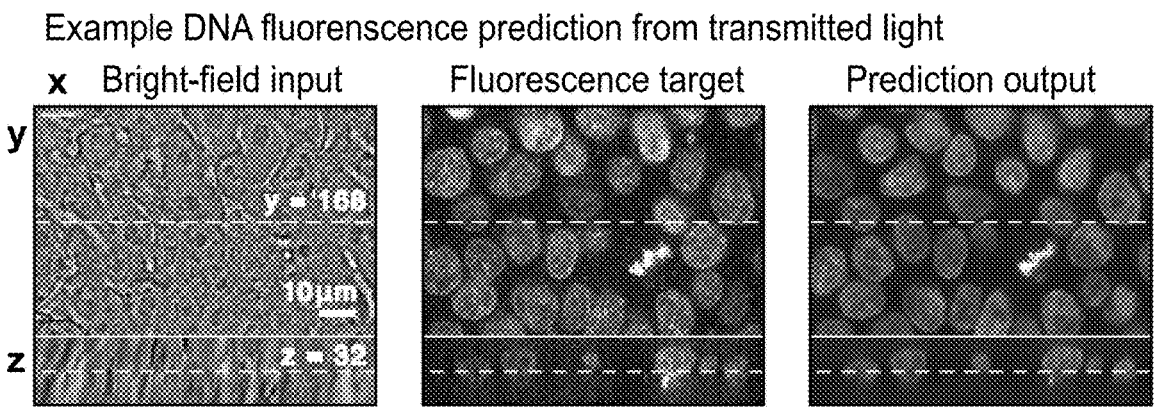
Figure 17C:
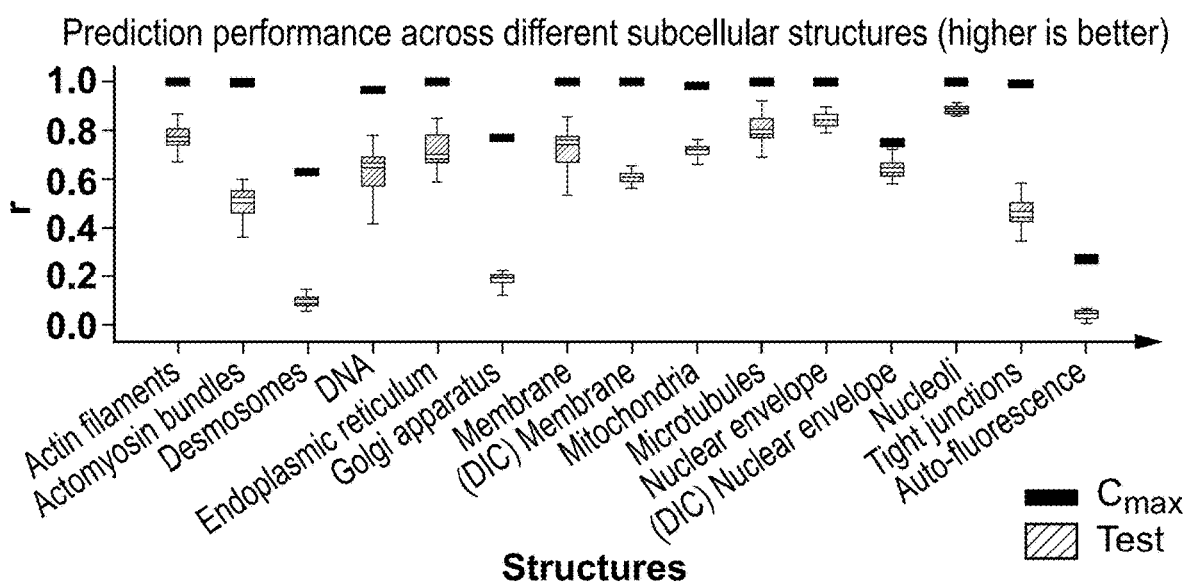
Figure 17D:
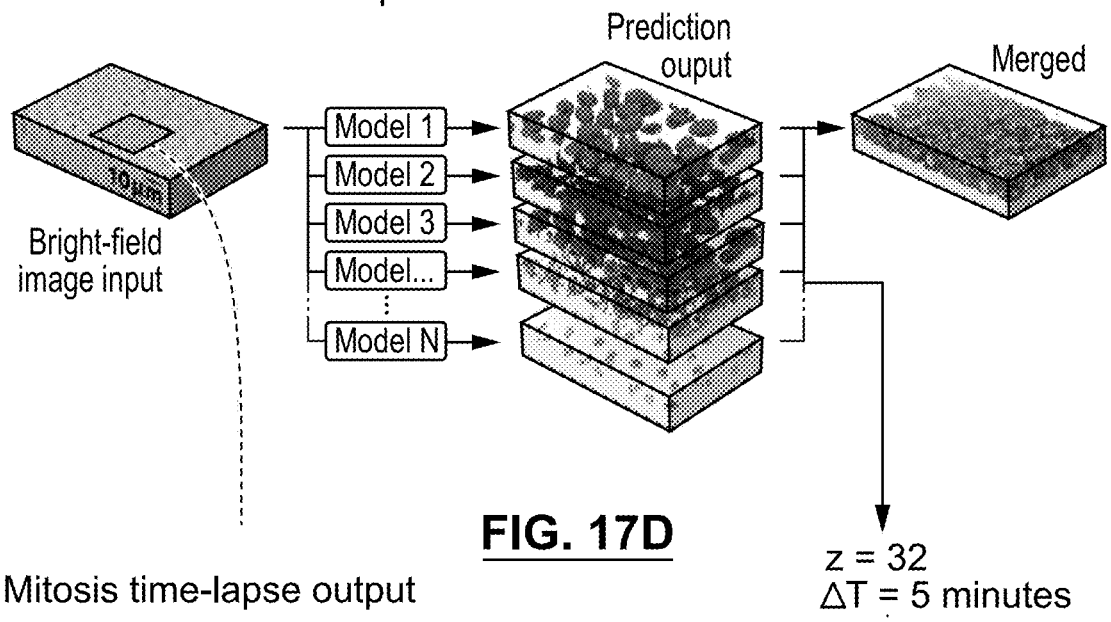
Figure 17E:
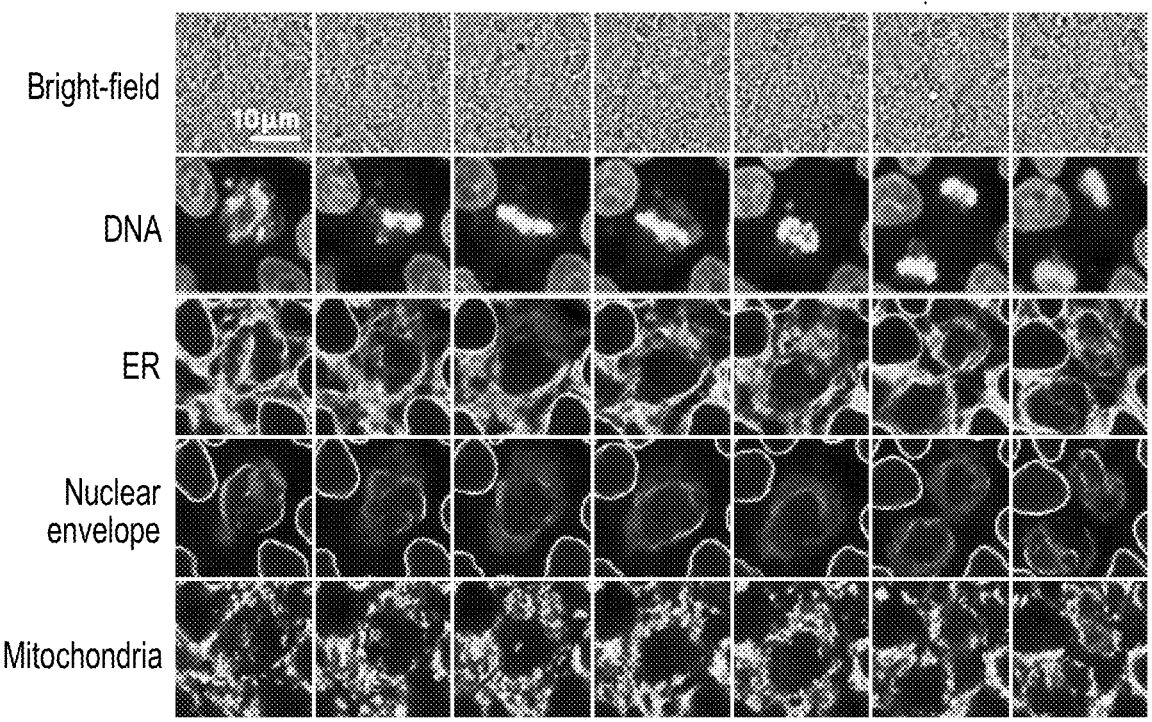

FIGS. 17A-17E provide another example of the predictive labeling, and more specifically an example of a label-free tool pipeline. In FIG. 17A, given the input of a transmitted light image, the model is trained by minimizing the mean-squared-error (MSE) between the corresponding fluorescence ground-truth and predicted images. In FIG. 17B, an example of a 3D input transmitted light image, a ground-truth confocal DNA fluorescence image, and a tool prediction are illustrated. FIG. 17C illustrates a distributions of the image-wise correlation coefficient (r) between target and predicted test images from models trained on 30 3D images for the indicated subcellular structure, plotted as a box across 25th, 50th and 75th percentile, with whiskers indicating the box range +/−1.5× inner quartile range. Maximum correlation between the image and a theoretical, noise-free image (Cmax, black line) is illustrated. FIG. 17D illustrates different models applied to the same input and combined to predict multiple imaging modes. FIG. 17E illustrates predicted localization of DNA (blue), endoplasmic reticulum (red), nuclear envelope (cyan) and mitochondria (orange) of a sample taken at 5-minute intervals. The center z-slice is shown. A mitotic event, along with stereotypical reorganization of subcellular structures, can be observed. The results are independent from training data except where explicitly labeled.

Figure 18A:
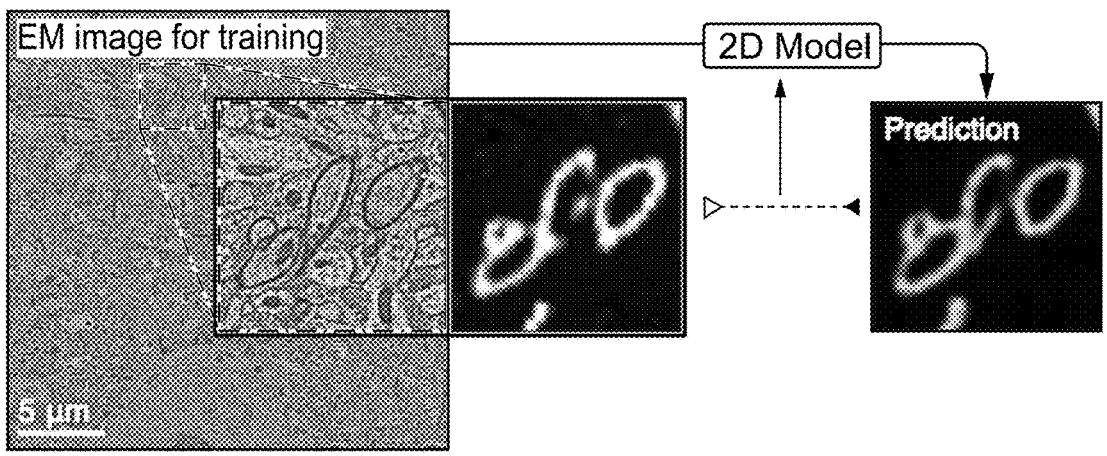
FIGS. 18A-18C illustrate an example of the automated registration across imaging modalities, according to an embodiment.
Figure 18B:
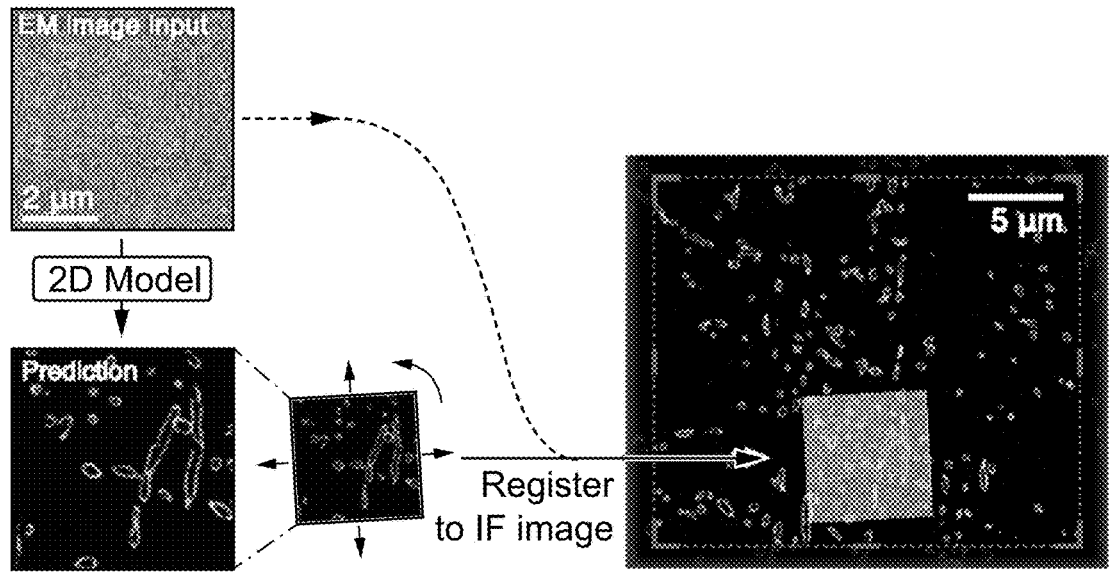
Figure 18C:
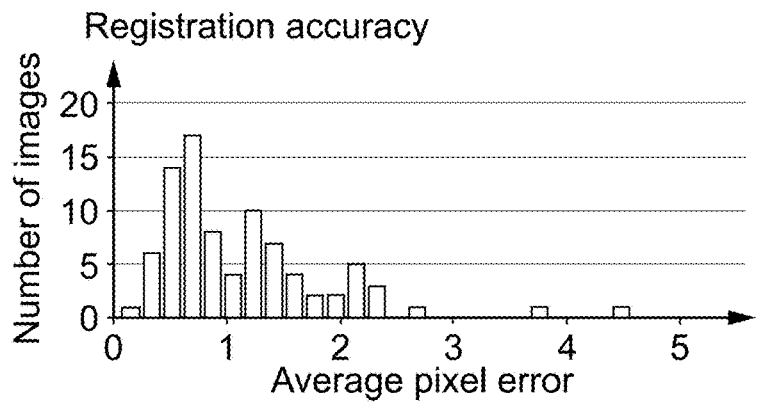

FIGS. 18A-18C illustrate another example of automated registration across imaging modalities. FIG. 18A illustrates electron micrographs that are manually registered to myelin basic protein immunofluorescence (MBF IF) images, to produce training data for a 2D model that can then predict MBP IF directly from electron micrographs. FIG. 18B depicts trained models were subsequently used in an automated registration workflow. Model predictions were registered via a similarity transformation to MBP IF images calculated using conventional automated computer vision techniques. FIG. 18C illustrates a histogram of average distance between automated registration and manual registration as measured across 90 test images, in units of pixels of MBP IF data.

In an embodiment, a statistical model can be trained to facilitate dye-free image-based cytometry. Some image-based cytometry techniques can use fluorescent dye to perform cell segmentation by tagging cellular structures such as cell membrane or cell nucleus, in order to allow cell counting and cell sorting to be performed from an image of the cellular structures. However, the fluorescent dye may present phototoxicity to the cell or cellular structure, such as in image-based cytometry systems that use 3D confocal laser scanning microscopy (CLSM), in which the small molecules of the fluorescent dye may exhibit phototoxicity when illuminated by the power of a CLSM laser. This phototoxicity may damage live cells, and thus may especially limit the ability to perform kinetic time course assays using image-based cytometry on live cells. The use of live cells may be especially useful for such assays, because dead cells may change in morphology even in the absence of a drug or other chemical being evaluated in the assays. Thus, one aspect of the embodiments herein relates to training a statistical model, such as a U-net or other deep neural network, to predict nuclear compartments, cell membrane or cell compartments, or other cellular structures from an image that was captured without applying fluorescent dye, and then using that model to facilitate cell counting, segmentation, or categorization (e.g., sorting) from subsequent images of live or dead cells. Such a trained statistical model can facilitate a dye-free kinetic cell assay.

In an embodiment, the statistical model can be trained using a first set of images in which fluorescent markers (or, more generally, fluorescent dye) were not used, and a second set of images in which fluorescent markers were used. The two images can capture the same set of cells or cellular structures. In some cases, the first set of images may be transmitted light images (e.g., brightfield images) or a cytometer image, such as an image captured using confocal laser scanning microscopy (CLSM), but without the use of fluorescent dye. For instance, the CLSM image can be generated using the GE IN Cell Analyzer®. The second set of images may be CLSM or other cytometer images, and may be captured with fluorescent dye. The statistical model can be trained to predict the second set of images with the first set of images as an input (e.g., using the CellProfiler pipeline).

Figure 19A:
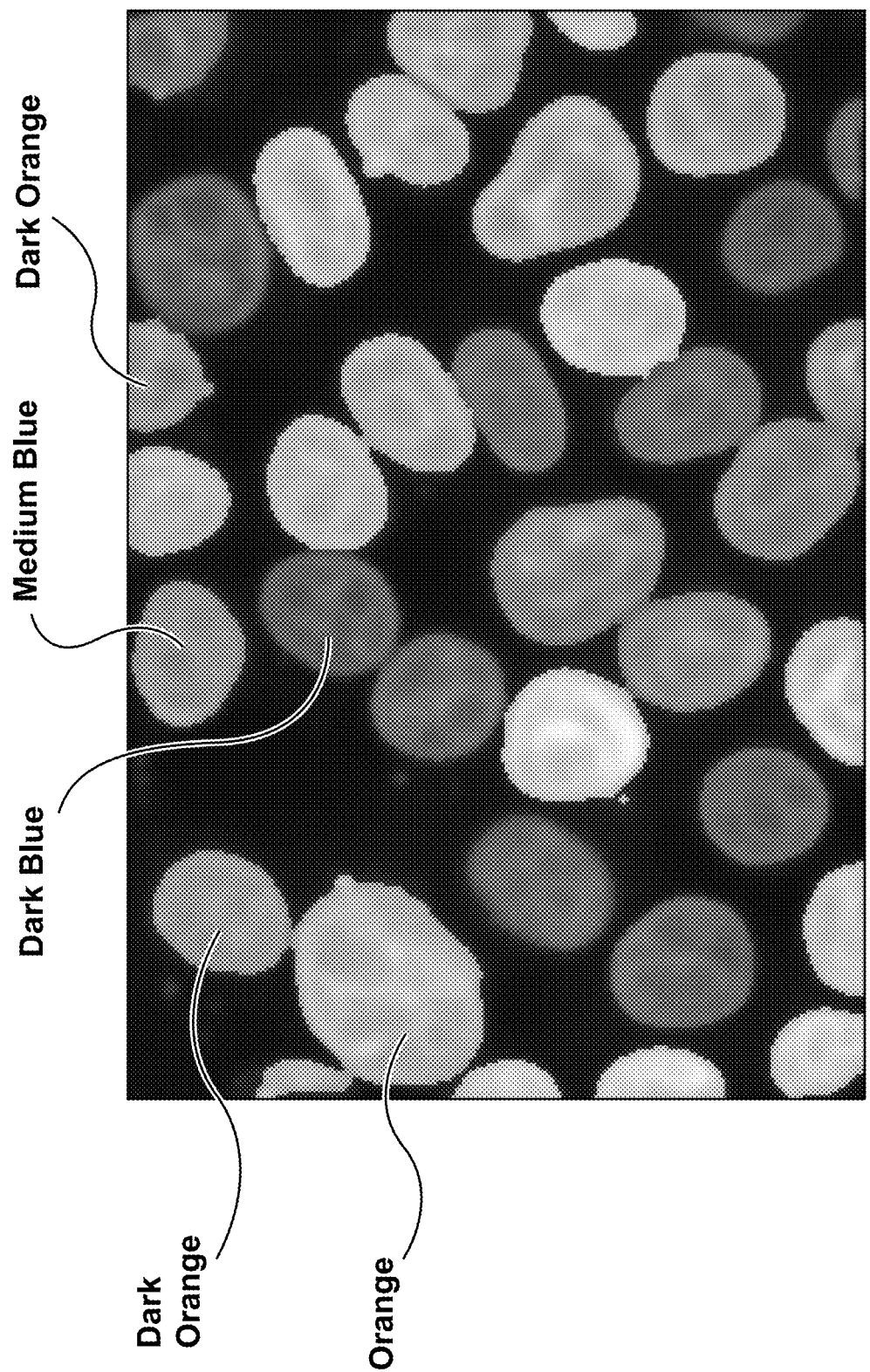
FIG. 19A illustrates an example 3D segmentation of nuclei from a brightfield predicted nuclei channel stack, according to an embodiment.
Figure 19B:
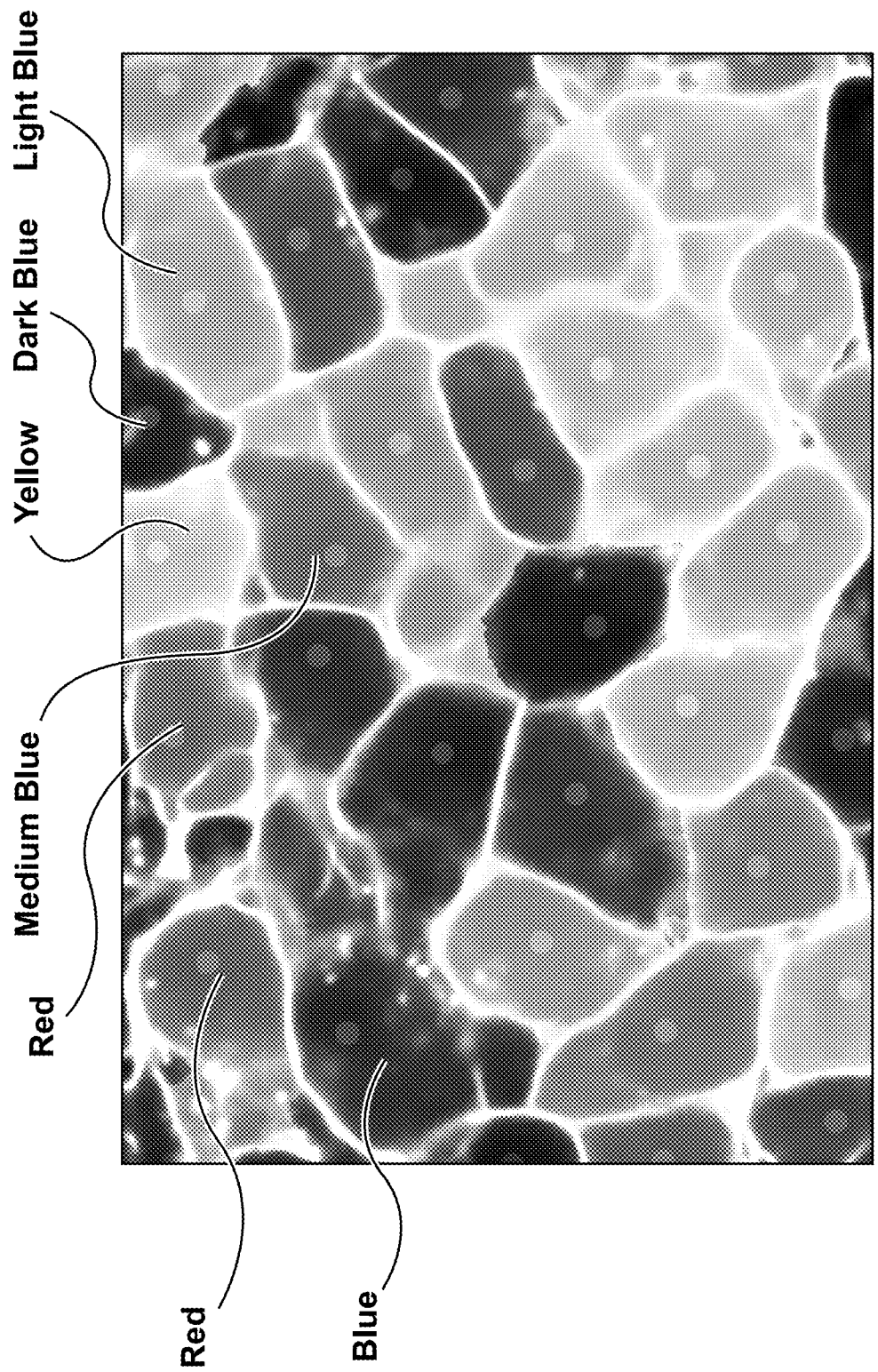
FIG. 19B illustrates an example 3D segmentation of cells from a brightfield predicted cell membrane channel image stack, according to an embodiment.

In an embodiment, the trained model can be used to perform 3D segmentation of living or dead cells. For instance, the trained model can be applied to an image of a biopsy of living cells, wherein no fluorescent dye was applied to the sample. The trained model can generate an image that approximates or otherwise predicts a cytometer image, such as a CLSM image, of the sample of living cells if a fluorescent marker had been applied to the sample. For instance, FIG. 19A illustrates a predicted CLSM image that illustrates where fluorescent labeling for cell nuclei would appear if fluorescent dye had been used. The predicted image in FIG. 19A can be used for 3D segmentation of nuclei from, e.g., a brightfield predicted nuclei channel image stack. Each nucleus may be indexed with a different color or with a different pattern (either relative to all other nuclei in FIG. 19A, or relative to all immediately neighboring nuclei), and may be overlaid or otherwise composited with the predicted CLSM image. As another example, FIG. 19B illustrates a predicted CLSM image that predicts where fluorescent labeling for cell membrane would appear if fluorescent dye had been used. The predicted image in FIG. 19B may be used for 3D segmentation of cells. Each cell can be indexed with a different color or pattern, and can be overlaid or otherwise composited with the predicted CLSM image.

In an embodiment, the same statistical model or another statistical model can be trained to further associate a predicted CLSM image or other cytometer image with a classification of whether the imaged cells or cellular structures are diseased cells, or a classification of a disease stage of the cells. For instance, this statistical model may be trained with images from cells that were known to be cancerous, or known to be in a particular stage of cancer. The model can thus be used to determine, e.g., estimate or otherwise predict whether a particular cell is cancerous, or determine a disease stage of the cells, such as by estimating the invasiveness of cancer by estimating that the imaged cells are dangerously proliferative based on mitotic status and structural characteristics.

Figure 20:
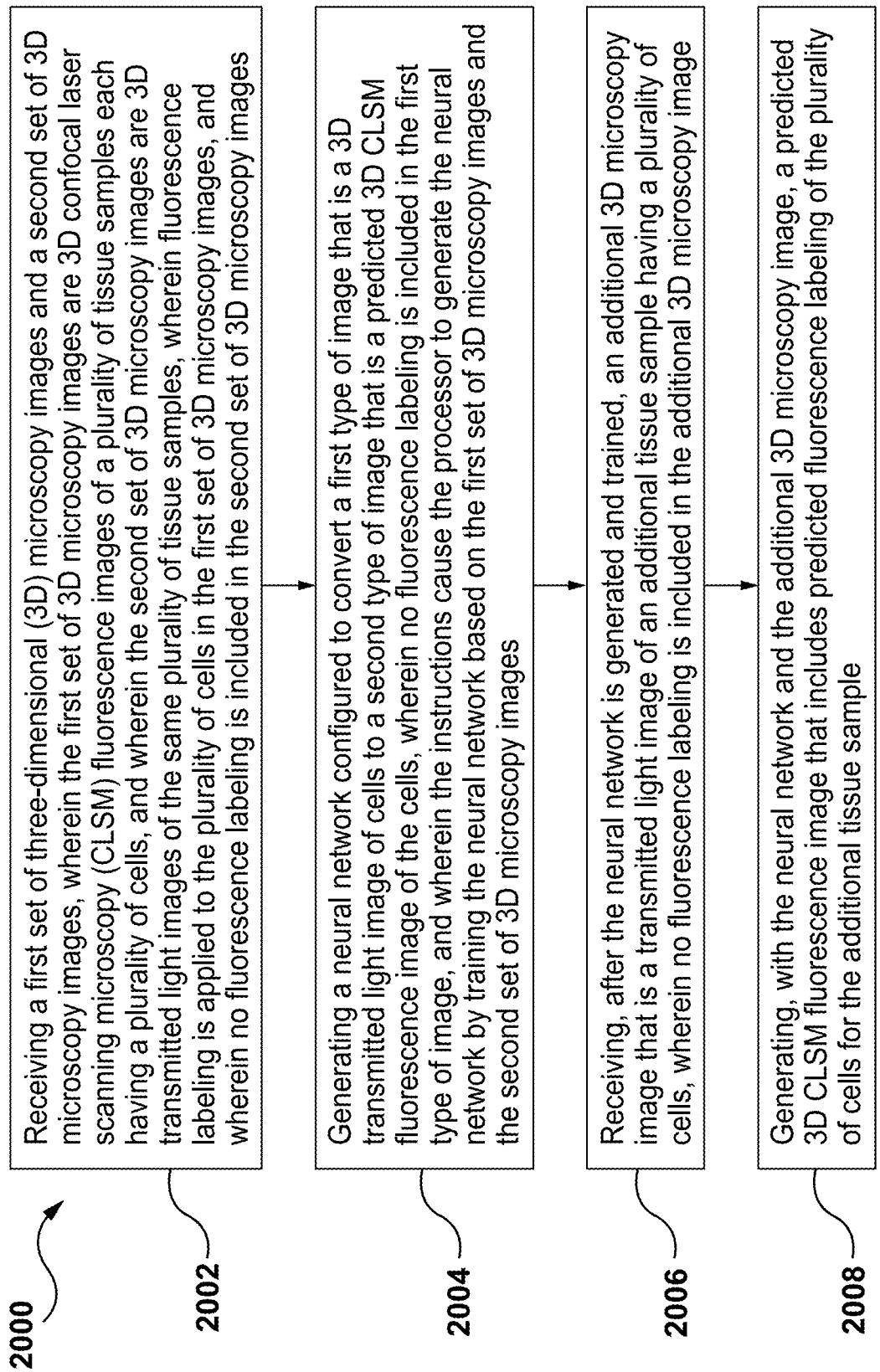
FIG. 20 illustrates a flow diagram of an example method for generating a predicted confocal laser scanning microscopy (CLSM) fluorescence image.

FIG. 20 illustrates a flow diagram in which the statistical model used to facilitate the cytometry is a neural network. More specifically, the flow diagram includes the steps of a method 2000, which may be performed by a processor, such as processor 120. In an embodiment, the method 2000 includes a step 2002, in which the processor receives, via a communication interface, a first set of three-dimensional (3D) microscopy images and a second set of 3D microscopy images, wherein the first set of 3D microscopy images are 3D confocal laser scanning microscopy (CLSM) fluorescence images of a plurality of tissue samples each having a plurality of cells, and wherein the second set of 3D microscopy images are 3D transmitted light images of the same plurality of tissue samples, wherein fluorescence labeling is applied to the plurality of cells in the first set of 3D microscopy images, and wherein no fluorescence labeling is included in the second set of 3D microscopy images. In an embodiment, the first set of 3D microscopy images may include multiple fluorescence channels, and each of the fluorescence channels may have been captured in a limited time interval of, e.g., 25 ms or less.

In step 2004, the processor generates a neural network configured to convert a first type of image that is a 3D transmitted light image of cells to a second type of image that is a predicted 3D CLSM fluorescence image of the cells, wherein no fluorescence labeling is included in the first type of image, and wherein the instructions cause the processor to generate the neural network by training the neural network based on the first set of 3D microscopy images and the second set of 3D microscopy images In step 2006, the processor receives, after the neural network is generated and trained, an additional 3D microscopy image that is a transmitted light image of an additional tissue sample having a plurality of cells, wherein no fluorescence labeling is included in the additional 3D microscopy image In step 2008, the processor generates, with the neural network and the additional 3D microscopy image, a predicted 3D CLSM fluorescence image that includes predicted fluorescence labeling of the plurality of cells for the additional tissue sample. In an embodiment, the processor may use the predicted 3D CLSM fluorescence image, a cell characteristic of the plurality of cells of the additional tissue sample, wherein the cell characteristic is at least one of an average or median cell size, a cell count, cell morphology of at least one of the plurality of cells, a cell cycle phase of at least one of the plurality of cells, or the presence or absence a protein biomarker on a surface of at least one of the plurality of cells. In an embodiment, the processor may train another neural network (a second neural network) that is configured to convert the second type of image that is the predicted 3D CLSM fluorescence image to a predicted classification of whether the predicted fluorescence 3D CLSM image includes a diseased cell, wherein the instructions cause the processor to generate the second neural network by training the second neural network with predicted 3D CLSM fluorescence images generated by the first neural network and with the received indication of which cell in the plurality of tissue samples is a diseased cell. The processor may then use the second neural network to generate a predicted classification of whether the additional tissue samples include a diseased cell.

The above-described techniques can thus facilitate histopathology and cytometry. More specifically, histopathology is the traditional method by which surgical samples/biopsies are examined by a pathologist after processing and sectioning for microscopic examination. The fixative steps necessary for this approach introduce an element of time (delay) and potential fixation artifacts which can mask key changes in morphology between normal and diseased cells. Cytopathology analyzes samples of free cells or tissue fragments to diagnose disease at the cellular level but may involve staining of cells to visualize structures microscopically. The devices, methods and processes discussed herein can allow key cellular structures and organelles to be identified without the need for dyes or stains and when trained and implemented appropriately, can quickly separate or otherwise segment cells into normal and diseased pools. Diseased samples can then be examined more closely by a trained pathologist to confirm machine-assisted diagnosis and provide more prognostic value, and can speed up the workflow and reduce the need for technically trained sample preparation. Altered DNA activity associated with the proliferative nature of cancer manifests as physical changes in nuclear qualities, which a model could be trained to identify.

The methods, systems and devices described herein can also be utilized for cell segmentation and/or cell sorting, utilizing image based cytometers (e.g., an "in plate" cytometer). Sorting can be based on characteristics such as cell size, cell count, cell morphology, spatiotemporal position or internal structures, cell cycle phase or the presence of absence of biomarkers (e.g., cell surface proteins). Images obtained from such cytometers can be utilized in training the various methods and systems described herein, for application to cell segmentation and sorting. Cells which can be modeled in such a manner include, for example, cell spheroids, organoids, human-induced pluripotent stem cells (hiPSCs), or patient derived tissue samples (e.g., patient derived xenograft model (PDX) systems).

Example Protocol

Test/Train split—For generation of each statistical model (e.g., similar to any variant of the statistical model as disclosed herein), data consisted of a set of image pairs: a 3D image in the starting imaging modality and a corresponding 3D image in the target imaging modality. Approximately 15 image pairs were allocated to the training set, and remaining image pairs were used in the test set. Training set images were used to optimize a model's parameters, whereas test set images were used to evaluate a trained model's performance.

Iterative training procedure—Models were iteratively trained using the following sequence:

1. Starting modality images from the training set were input into the model.

2. The difference between the model output from the target modality images was quantified with a loss function.

3. Model parameters are adjusted in directions that would minimize the loss function (parameter optimization).

4. Repeat until model convergence.

Training Methodology—The models were trained using 32×64×64 pixel (ZYX dimensions respectively) volume pairs that were randomly sampled from the training images ($X_{train}$, $Y_{train}$). For each training iteration, batches of 24 volume pairs and pixelwise mean squared error as the loss function where employed. The Adam optimizer was employed with a learning rate of 0.001 to perform gradient descent. Each model was trained with 50,000 training iterations, which took approximately 15 hours to complete.

Testing—We evaluated each trained model's performance against its test set. Unlike during the training phase, the model was tested with each test set image pair (Xtest, Ytest) with no subsampling, one image pair at a time. The mean of the loss function value from each image pair provided a metric for the trained model's performance.

Example Methodology for Obtaining Imaging Data for Training and Validation

In an embodiment, the 3D light microscopy data used to train and test a model includes z-stacks of genome-edited human induced pluripotent stem cell (hiPSc) lines, each of which expresses a protein endogenously tagged with eGFP which localizes to a particular subcellular structure, as detailed in "Systematic gene tagging using crispr/cas9 in human stem cells to illuminate cell organization" by Roberts, B. et al., the entire content of which is incorporated herein by reference. In each image, four data channels may have been acquired: transmitted light (either bright-field or DIC), dye-labeled cell membrane (CellMask), dye-labeled DNA (Hoechst), and the particular GFP-tagged subcellular structure associated with the cell line being imaged, as detailed below. Some examples may use cell lines with the following eGFP-labeled proteins (localized to the associated subcellular structure in parentheses): α-tubulin (microtubules), β-actin (actin filaments), desmoplakin (desmosomes), lamin B1 (nuclear envelope), fibrillarin (nucleoli), Myosin IIB (actomyosin bundles), Sec61 β(endoplasmic reticulum), STGAL1 (Golgi apparatus). In one example, the time-series data can be acquired using the same imaging protocol as for acquisition of training data but with no applied Hoechst or CellMask dyes and with all laser powers set to zero. The images can be resized via cubic interpolation such that each voxel corresponded to, e.g., 0:29 $\mu m^3$.

In an embodiment, pixel intensities of all input and target images can be independently z-scored. This can use paired fluorescence and corresponding transmitted light channels, resulting in 14 image collections. For each collection, 30 image pairs can be allocated to a training set and all the remaining image pairs to a test set.

Example Methodology for Conjugate Array Tomography

In one exemplary implementation for conjugate array tomography data, images of 50 ultra-thin slices are taken with a widefield fluorescence microscope using 3 rounds of staining and imaging to obtain 10 channel immunofluorescence (IF) data (including myelin basic protein, MBP) at 100 nm per pixel. In this example, 5 small regions are then imaged with a field emission scanning electron microscope to obtain high resolution electron micrographs at 3 nm per pixel. Image processing steps independently stitched the IF slices and one of the EM regions to create 2D montages in each modality. Each EM montage is then manually registered to the corresponding MBP channel montage TrakEM2, as described in "Trakem2 software for neural circuit reconstruction," by Cardona, A. et al., the entire content of which is incorporated herein by reference. In one example, to create a training set, 40 pairs of these registered EM and MBP montages are resampled to 10 nm per pixel. For each montage pair, a central region of size 2544 px×2352 px was cutout and used for the resultant final training set. Pixel intensities of the images were z-scored.

Example Methodology for Training Model

In an embodiment, a CNN based on various U-Net/3D U-Net architectures can be used, as described in "U-net: Convolutional networks for biomedical image segmentation," by Ronneberger, O., Fischer, P. & Brox, T., and in "3d u-net: learnin dense volumetric segmentation from sparse annotation," by Cicek, O., Abdulkadir, A., Lienkamp, S. S., Brox, T. & Ronnenberger, O., the entire contents of which are incorporated herein by reference.

In an embodiment, the model includes layers that perform one of three convolution types, followed by a batch normalization and ReLU operation. The convolutions are either 3 pixel convolutions with a stride of 1-pixel on zero-padded input (such that input and output of that layer are the same spatial area), 2-pixel convolutions with a stride of 2 pixels (to halve the spatial area of the output), or 2-pixel transposed convolutions with a stride of 2 (to double the spatial area of the output). In an embodiment, there is no batch normalization or ReLU layers on the last layer of the network.

In an embodiment, the 2D and 3D models use 2D or 3D convolutions, respectively. Due to memory constraints associated with GPU computing, the model can be trained on batches of either 3D patches (32 px×64 px×64 px, z-y-x) for light microscopy data or on 2D patches (256 px×256 px, y-x) for conjugate array tomography data, which were randomly subsampled uniformly both across all training images as well as spatially within an image. In an embodiment, the training procedure can take place in a forward-backward fashion, updating model parameters via stochastic gradient descent ('backpropagation') to minimize the mean-squared-error between output and target images. In an embodiment, all models described above are trained using the Adam optimizer, with a learning rate of 0.001 and with betas 0.5 and 0.999 for 50,000 mini-batch iterations. The Adams optimizer is described in "Adam: A Method for Stochastic Optimization," by Kingma, D. P. et al., the entire content of which is incorporated herein by reference. In an embodiment, a batch size of 24 for 3D models and of 32 for 2D models is used. In an embodiment, running on a Pascal Titan X, each model can complete training in approximately 16 hours for 3D models and in 7 hours for 2D models. For prediction tasks, minimal cropping on the input image may be done such that its size in any dimension is a multiple of 16, to accommodate the multi-scale aspect of CNN architecture. Prediction may take approximately 1 second for 3D images and 0.5 seconds for 2D images. In an embodiment, model training pipeline can be implemented in Python using the PyTorch package.

Example Methodology for 3D Light Microscopy Model Results Analysis and Validation In an embodiment, for 3D light microscopy applications, independent test images are not used for training, and model accuracy can be quantified by the Pearson correlation coefficient between the model's output and the independent, ground truth test image. For each model, a corresponding estimate of noise can be developed based upon image stacks taken of unlabeled hIPS cells not stained with either the CellMask or Hoechst, but for which microscope settings were identical to those used during labeled acquisitions. For each image prediction, a theoretical upper bound of model performance is calculated, based upon the assumption that the variance of the unlabeled image stacks is a lower bound on the variance of uncorrelated, random fluctuations $N_{x,y,z}$ in the ground truth images, $T_{x,y,z}$, which should not be predictable, such that: $T_{x,y,z}=N_{x,y,z}+S_{x,y,z}$, where S is the predictable signal in the image. In some instances, the highest expectation for model performance is thus S and the correlation between T and S is $C_{max}$=square root of (SNR/(1+SNR)), where SNR=$<S^2>/<N^2>$.

Registration Across Imaging Modalities

In an embodiment, the image registration employs a 2D version of the above-described tool trained on the montage pairs described above with respect to "Example Methodology for Obtaining Imaging Data for Training and Validation". For the test set, each of the individual EM images (without montaging) from all five regions (a total of 1500 images) can be used as an input to directly register to the corresponding MBP image in which it lies. For this, each image can be first downsampled to 10 nm per pixel without any transformations to generate a 1500 px×1500 px image. This was then reflection padded to 1504 px×1504 px as in "U-net: Convolutional networks for biomedical image segmentation" by Ronneberger, O. et al., and may be run through the trained model, and then cropped back to the original input size to generate an MBP prediction image. This MBP prediction image can be first roughly registered to MBP IF images using cross-correlation-based template matching for a rigid transformation estimate. Next, the residual optical flow between the predicted image transformed by the rigid estimate and the MBP IF image can be calculated, which can then be used to fit a similarity transformation that registers the two images (implemented using OpenCV 11). The optical flow is described in "Two-frame motion estimation based on polynomial expansion," by Farneback, G., the entire content of which is incorporated herein by reference. OpenCV is described in the "Open source computer vision library." In on example, 90 prediction images are randomly selected from the larger set, where more than 1% of the predicted image pixels were greater than 50% of the maximum intensity, to ensure that the images contained sufficient MBP content to drive registration. Ground truth transformation parameters can be calculated by two independent authors on this subset of EM images by manual registration (3-4 minutes per pair) to the MBP IF images using TrakEM2. Differences in registrations (between authors and between the algorithm estimate and one of the authors) can be calculated by the average difference in displacement across an image, as measured in pixels of the target IF image.

While various embodiments have been described above, it should be understood that they have been presented by way of example only, and not limitation. Where methods described above indicate certain events occurring in certain order, the ordering of certain events may be modified. Additionally, certain of the events may be performed concurrently in a parallel process when possible, as well as performed sequentially as described above.

Where schematics and/or embodiments described above indicate certain components arranged in certain orientations or positions, the arrangement of components may be modified. While the embodiments have been particularly shown and described, it will be understood that various changes in form and details may be made. Any portion of the apparatus and/or methods described herein may be combined in any combination, except mutually exclusive combinations. The embodiments described herein can include various combinations and/or sub-combinations of the functions, components, and/or statistical models of the different embodiments described.

Additional Discussion of Various Embodiments

Embodiment 1 is a device, comprising a communication interface configured to receive a plurality of sets of 3-dimensional (3D) images, a first set of 3D images of the plurality of sets of 3D images including fluorescence images of one or more cellular structures, a second set of 3D images of the plurality of sets of 3D images including transmitted light images of the one or more cellular structures. The device further comprises a memory communicably coupled to the communication interface and configured to store the plurality of sets of 3D images, the memory further configured to store computer executable instructions. The device additionally comprises a processor communicably coupled to the memory and configured to execute the computer executable instructions to: generate a statistical model to associate the one or more cellular structures in the first set of 3D images with the one or more cellular structures in the second set of 3D images; apply the statistical model to a third set of 3D images of the plurality of sets of 3D images to estimate the location of the one or more cellular structures in the third set of 3D images; and generate a fourth set of 3D images, the fourth set of 3D images including an indication of the estimated location of the one or more cellular structures in the third set of 3D images.

Embodiment 2 is the device of embodiment 1, wherein the one or more cellular structures is selected from the group consisting of cell membrane, plasma membrane, nucleus, mitochondria, endoplasmic reticulum, vacuole, Golgi Apparatus, and lysosomes.

Embodiment 3 is the device of embodiment 1 or 2, wherein the processor further configured to: deem the first set of 3D images and the second set of 3D images as training data set, and to generate the statistical model based on the training data set; and deem the third set of 3D images as testing data set, and to apply the statistical model to the testing data set.

Embodiment 4 is the device of any one of embodiments 1-3, wherein the statistical model is a convolutional neural network.

Embodiment 5 is the device of embodiment 4, wherein the convolutional neural network is based on modified u-net architecture.

Embodiment 6 is the device of any one of embodiments 1-5, the communication interface configured to receive an indication of the location of the one or more cellular structures in the testing data set, the processor further configured to modify the statistical model based on the estimated location of the one or more cellular structures in the testing data set and based on the received indication of the location of the one or more cellular structures in the testing data set.

Embodiment 7 is the device of any one of embodiments 1-6, wherein the transmitted light images are selected from the group consisting of brightfield images, darkfield images, and differential interference contrast (DIC) images.

Embodiment 8 is a method having the steps performed by the processor in embodiment 1.

Embodiment 9 is a device comprising a communication interface configured to receive a plurality of sets of 3-dimensional (3D) images, a first set of 3D images of the plurality of sets of 3D images including fluorescence images, a second set of 3D images of the plurality of sets of 3D images including transmitted light images. The device further includes a memory communicably coupled to the communication interface and configured to store the plurality of sets of 3D images, the memory further configured to store computer executable instructions. The device further includes a processor communicable coupled to the memory and configured to execute the computer executable instructions to: extract a first set of training images showing a first region from the first set of 3D images; extract a second set of training images showing the first region from the second set of 3D images; extract a first set of test images showing a second region from the first set of 3D images; extract a second set of test images showing the second region from the second set of 3D images; generate a statistical model to associate a one or more cellular structures in the first set of training images with the one or more cellular structures in the second set of training images; apply the statistical model to the first set of test images to estimate the location of the one or more cellular structures in the first set of test images; compare the estimated location of the one or more cellular structures in the first set of test images with the location of the one or more cellular structures in the second set of test images; and modify the statistical model based on said comparing.

Embodiment 10 includes a method having the steps performed by the processor of embodiment 9.

Embodiment 11 is a method or system for detecting or visualizing intracellular structures in cells using three dimensional transmitted light microscopy, comprising quantifying the relationship between transmitted light images in a cell and the localization of dye and fluorescently labeled intracellular structures in the cell and detecting the intracellular images in the cell without fluorescently labeling the cell.

Embodiment 12 is a method or system for predicting the spatiotemporal position of intracellular structures in one or more cells from transmitted light microscopy, comprising quantifying the relationship between transmitted light images in the one or more cells and the localization of dye and fluorescently labeled nuclei in the one or more cells and detecting the intracellular images with transmitted light microscopy.

Embodiment 13 is a method or system for generating images of intracellular structures, comprising accepting transmitted light microscopy images of cells, generating expected fluorescence microscopy images from those cells, and visualization of intracellular structures without labels and fluorescent imaging.

Embodiment 14 is a deep neural network or deep net tool created by the method or system of any of embodiments 1-13.

Embodiment 15 is a computer-implemented method for automated prediction of localization of intracellular structures from three dimensional transmitted light microscopy, comprising: generating one or more fluorescently labeled cells or tissue samples; generating an image of the one or more fluorescently labeled cells or tissue samples; determining the localization of intracellular structures in the one or more fluorescently labeled cells; generating a three dimensional three dimensional transmitted light images of the one or more cells or tissue samples; using a deep neural network, deep net tool, or machine learning to quantify the relationship between the localization of dye and fluorescently labeled intracellular structures in the one or more fluorescently labeled cells and in the three dimensional transmitted light images of intracellular structures in the one or more cells or tissue samples. The deep neural network, deep net tool, or machine learning predicts the localization of intracellular structures in the one or more cells or tissue samples from three dimensional transmitted light microscopy.

Embodiment 16 is a device comprising a communication interface configured to receive a first pair of images, wherein the first pair of images include a first image that is a fluorescence image of one or more cellular structures, and include a second image that is an electron micrograph (EM) image of the one or more cellular structures, wherein the first image and the second image are registered with each other, such that they are aligned with each other and represent the same scale, or have associated registration information also received by the communication interface indicating how the first image and the second image can be aligned with each other. The device further includes a memory communicably coupled to the communication interface and configured to store the first image and the second image, the memory further configured to store computer executable instructions. The device further includes a processor communicably coupled to the memory and configured to execute the computer executable instructions to: generate a statistical model to associate the one or more cellular structures in the first image with the one or more cellular structures in the second image; receive a second pair of images, wherein the second pair of images include a third image that is a fluorescence image, and a fourth image that is an electron microscope (EM) image, wherein the third image and the fourth image are both of the one or more cellular structures, or of another one or more cellular structures, and wherein the third image and the fourth image are not registered with each other; apply the statistical model to the fourth image generate an estimated fluorescence image based on the fourth image; determine registration information between the estimated fluorescence image and the third image, register the third image and the fourth image with each other based on the registration information.

Embodiment 17 is the device comprising: a communication interface configured to receive a first image of a first set of cells or cellular structures, and a second cytometer image of the first set of cells or cellular structures, wherein the first image is a transmitted light image or a first cytometer image and is captured without fluorescent dye being applied to the first set of cells or cellular structures, and wherein the second cytometer image is captured with fluorescent dye being applied to the first set of cells or cellular structures. The device further comprises a memory communicably coupled to the communication interface and configured to store the first image and the second cytometer image, the memory further configured to store computer executable instructions. The device further comprises a processor communicably coupled to the memory and configured to execute the computer executable instructions to: generate a statistical model to associate cellular structures in the first image with cellular structures in the second cytometer image; receive a third image, wherein the third image is of a second set of cells or cellular structures and is captured without fluorescent dye being applied to the second set of cells or cellular structures; apply the statistical model to the third image to generate a fourth image, wherein the fourth image includes an indication of estimated locations of one or more cellular structures in the third image.

Embodiment 18 relates a computing device, comprising a communication interface configured to receive microscopy images, a processor, and a non-transitory computer-readable medium. The non-transitory computer-readable medium is communicatively coupled to the processor and storing computer-executable instructions that, when executed by the processor, causes the processor to: receive, via the communication interface, a first set of three-dimensional (3D) microscopy images and a second set of 3D microscopy images, wherein the first set of 3D microscopy images are 3D fluorescence images of a plurality of sub-cellular structures in a plurality of tissue samples, and wherein the second set of 3D microscopy images are 3D transmitted light images of the same plurality of sub-cellular structures, wherein no fluorescence labeling is included in the second set of 3D microscopy images. The instructions further cause the processor to generate a neural network configured to convert a first type of image that is a 3D transmitted light image of any sub-cellular structure to a second type of image that is a predicted 3D fluorescence image of the sub-cellular structure, wherein no fluorescence labeling is included in the first type of image, and wherein the instructions cause the processor to generate the neural network by training the neural network based on the first set of 3D microscopy images and the second set of 3D microscopy images. The instructions further cause the processor to determine a parameter value of an image acquisition parameter that was used to capture the second set of 3D microscopy images from the plurality of tissue samples. The instructions further cause the processor to receive, after the neural network is generated and trained, an additional 3D microscopy image that is a transmitted light image of one or more sub-cellular structures in an additional tissue sample, wherein no fluorescence labeling is included in the additional 3D microscopy image, and wherein the additional 3D microscopy image is captured from the one or more sub-cellular structures of the additional tissue sample with the parameter value that was used to capture the second set of 3D microscopy images. The instructions further cause the processor to generate, with the neural network and the additional 3D microscopy image, a predicted 3D fluorescence image that includes predicted fluorescence labeling for the additional tissue sample.

Embodiment 19 includes the computing device of embodiment 18, wherein the non-transitory computer-readable medium comprises a first memory portion having a first level of access latency and a second memory portion having a second level of access latency longer than the first level, and wherein a total storage capacity of the first memory portion is less than a total memory size of the first set of 3D microscopy images and the second set of 3D microscopy images. The instructions cause the processor to store the first set of 3D microscopy images and the second set of 3D microscopy images in the second memory portion, and to train the neural network over a plurality of iterations with different respective portions of the first set of 3D microscopy images and different respective portions of the second set of 3D microscopy images, by performing the following during each of the plurality of iterations: retrieving from the second memory portion only a respective portion of the first set of 3D microscopy images and only a respective portion of the second set of 3D microscopy images; storing the respective portion of the first set of 3D microscopy images and the respective portion of the second set of 3D microscopy images in the first memory portion; and training the neural network during the iteration with the respective portion of the first set of 3D microscopy images currently stored in the first memory portion, and with the respective portion of the second set of 3D microscopy images currently stored in the first memory portion.

Embodiment 20 includes the computing device of embodiment 19, wherein the non-transitory computer-readable medium comprises a random access memory (RAM) and a hard disk drive (HDD), wherein the first memory portion is part of the RAM, and the second memory portion is part of the HDD.

Embodiment 21 includes the computing device of embodiment 19 or 20, wherein the instructions further cause the processor to downsample, before training the neural network, each of the first set of 3D microscopy images and each of the second set of 3D microscopy images.

Embodiment 22 includes the computing device of embodiment 21, wherein each of the first set of 3D microscopy images and each of the second set of 3D microscopy images have, after being downsampled, a resolution that that represents a range of 0.108 μm to 0.29 μm per pixel along at least one of the dimensions of the respective 3D microscopy image.

Embodiment 23 includes the computing device of any one of embodiments 18-22, wherein a total number of images in the first set of 3D microscopy images is less than 500 images, and a total number of images in the second set of 3D microscopy images is less than 500 images, such that the neural network is trained with less than 500 pairs of images.

Embodiment 24 includes the computing device of any one of embodiments 18-23, wherein the neural network has a u-net architecture.

Embodiment 25 includes the computing device of any one of embodiments 18-24, wherein the image acquisition parameter is a parameter used to perform Kohler illumination on the plurality of tissue samples and on the additional tissue sample.

Embodiment 26 includes the computing device of any one of embodiments 18-25, wherein the image acquisition parameter is an exposure time parameter.

Embodiment 27 includes the computing device of any one of embodiments 18-26, wherein the image acquisition parameter is an inter-slice interval.

Embodiment 28 includes the computing device of any one of embodiments 18-27, wherein the additional 3D microscopy image is one of a third set of 3D microscopy images captured from the additional tissue sample at different points in time, wherein each of the third set of 3D microscopy images is a transmitted light image of the one or more sub-cellular structures of the additional tissue sample. In this embodiment, the predicted 3D fluorescence image is one of a set of predicted 3D fluorescence images that are generated with the neural network based on the third set of 3D microscopy images, and wherein the instructions further cause the processor to generate an animation of the one or more sub-cellular structures of the additional tissue sample using the set of predicted 3D fluorescence images.

Embodiment 29 includes the computing device of any one of embodiments 18-28, wherein the second set of 3D microscopy images and the additional 3D microscopy image are each a brightfield image, a darkfield image, or a differential interference contrast (DIC) image.

Embodiment 30 includes the computing device of any one of embodiments 18-29, wherein the first set of 3D microscopy images and the second set of 3D microscopy images capture a lipid envelope structure in at least some of the plurality of tissue samples.

Embodiment 31 includes the computing device of any one of embodiments 18-29, wherein the one or more sub-cellular structures of each of the plurality of tissue samples include at least one of a cell membrane, a plasma membrane, a nucleus, mitochondria, endoplasmic reticulum, vacuole, Golgi Apparatus, or a lysosome.

Embodiment 32 includes the computing device of any one of embodiments 18-31, wherein the one or more sub-cellular structures of the additional tissue sample are part of a live cell, such that the additional 3D microscopy image is captured from the one or more sub-cellular structures of the live cell.

Embodiment 33 includes the computing device of any one of embodiments 18-32, wherein the each of the first set of 3D microscopy images is in alignment with one of the second set of 3D microscopy images before the first set of 3D microscopy images and the second set of 3D microscopy images are used to train the neural network.

Embodiment 34 includes the computing device of any one of embodiments 18-33, wherein the first set of 3D microscopy images includes a subset of 3D fluorescence images for one of the plurality of tissue samples, wherein the subset of 3D fluorescence images correspond to different respective fluorescence channels that each has a different respective emission filter frequency band or a different respective fluorescence marker.

Embodiment 35 relates a computing device, comprising a communication interface configured to receive microscopy images, a processor, and a non-transitory computer-readable medium. The non-transitory computer-readable medium is communicatively coupled to the processor and storing computer-executable instructions that, when executed by the processor, causes the processor to: receive, via the communication interface, a first set of three-dimensional (3D) microscopy images and a second set of 3D microscopy images, wherein the first set of 3D microscopy images are 3D fluorescence images of a plurality of sub-cellular structures in a plurality of tissue samples, and wherein the second set of 3D microscopy images are 3D transmitted light images of the same plurality of sub-cellular structures, wherein no fluorescence labeling is included in the second set of 3D microscopy images. The instructions further cause the processor to generate a statistical model configured to convert a first type of image that is a 3D transmitted light image of any sub-cellular structure to a second type of image that is a predicted 3D fluorescence image of the sub-cellular structure, wherein no fluorescence labeling is included in the first type of image, and wherein the instructions cause the processor to generate the statistical model by training the neural network based on the first set of 3D microscopy images and the second set of 3D microscopy images. The instructions further cause the processor to receive, after the neural network is generated and trained, an additional 3D microscopy image that is a transmitted light image of one or more sub-cellular structures in an additional tissue sample, wherein no fluorescence labeling is included in the additional 3D microscopy image, and wherein the additional 3D microscopy image is captured from the one or more sub-cellular structures of the additional tissue sample. The instructions further cause the processor to generate, with the statistical model and the additional 3D microscopy image, a predicted 3D fluorescence image that includes predicted fluorescence labeling for the additional tissue sample.

Embodiment 36 relates to a computing device, comprising a communication interface configured to receive microscopy images, a processor; and a non-transitory computer-readable medium communicatively coupled to the communication interface and to the processor, and storing computer-executable instructions that, when executed by the processor, causes the processor to: receive, via the communication interface, a first set of microscopy images and a second set of microscopy images, wherein the first set of microscopy images are fluorescence images of a plurality of tissue samples each having one or more sub-cellular structures or one or more cells, and wherein the second set of microscopy images are electron micrograph (EM) images of the one or more sub-cellular structures or one or more cells of the plurality of tissue samples, wherein no fluorescence labeling is included in the second set of microscopy images. The instructions further cause the processor to determine that each of the first set of microscopy images is aligned with one of the second set of microscopy images. The instructions further cause the processor to generate, after determining that each of the first set of microscopy images is aligned with one of the second set of microscopy images, a neural network (or, more generally, a statistical model) configured to convert a first type of image that is an EM image of any sub-cellular structure or cell to a second type of image that is a predicted fluorescence image of the sub-cellular structure or cell, wherein no fluorescence labeling is included in the first type of image, and wherein the instructions cause the processor to generate the neural network by training the neural network based on the first set of 3D microscopy images and the second set of 3D microscopy images. The instructions further cause the processor to receive, after the neural network is generated, a pair of microscopy images that include a third microscopy image and a fourth microscopy image, wherein the third microscopy image is a fluorescence image of one or more cellular structures or one or more cells of an additional tissue sample, and the fourth microscopy image is an EM image of the one or more sub-cellular structures or one or more cells of the additional tissue sample, wherein the third microscopy image and the fourth microscopy image are not aligned with each other. The instructions further cause the processor to generate, with the neural network and the EM image of the fourth microscopy image, a predicted fluorescence image that includes predicted fluorescence labeling for the additional tissue sample. The instructions further cause the processor to determine registration information that indicates how the predicted fluorescence image can be aligned with the fluorescence image of the third microscopy image; and perform registration of the third microscopy image and the fourth microscopy image using the determined registration information.

Embodiment 37 includes the computing device of embodiment 36, wherein the instructions cause the processor to perform the registration by performing at least one of shifting, rotating, or scaling of the third microscopy image relative to the fourth microscopy image based on the registration information.

Embodiment 38 includes the computing device of embodiment 37, wherein the instructions cause the processor to overlay the third microscopy image on the fourth microscopy image after the third microscopy image has been shifted, rotated, or scaled based on the registration information.

Embodiment 39 includes the computing device of any one of embodiments 36-38, wherein the instructions cause the processor to determine the registration information by using an intensity-based registration process that performs intensity matching between the predicted fluorescence image and the third microscopy image.

Embodiment 40 includes the computing device of any one of embodiments 36-39, wherein each of the third microscopy image and the fourth microscopy image includes a plurality of pixels, and wherein, before registration is performed, each pixel of the third microscopy image represents a bigger region of the additional tissue sample than does each pixel of the fourth microscopy image, such that the fluorescence image of the third microscopy image is at a lower level of magnification relative to the EM image of the fourth microscopy image.

Embodiment 41 includes the computing device of embodiment 40, wherein, before registration is performed, each pixel of the third microscopy image represents a region of the additional tissue sample that is at least 100 times larger than a region of the additional tissue sample represented by each pixel of the fourth microscopy image.

Embodiment 42 includes the computing device of any one of embodiments 36-41, wherein the registration information that is determined is a second set of registration information, wherein the instructions further cause the processor to: receive a first set of registration information that indicates how each image of the first set of microscopy images can be aligned with one of the second set of microscopy images, and perform registration of the first set of microscopy images with the second set of microscopy images, based on the first set of registration information, wherein the processor determines that each of the first set of microscopy images is aligned with one of the second set of microscopy images and trains the neural network in response to performing the registration.

Embodiment 43 includes the computing device of any one of embodiments 36-41, wherein the EM image of the third microscopy image was captured by an electron microscope at a first level of magnification of a first region of the additional tissue sample, wherein the instructions further cause the processor to control the electron microscope to acquire a fifth microscopy image of a second region that is a portion of the first region, wherein a location of the second region within the first region is indicated by the registration information, and wherein the fifth microscopy image is an EM image that is at a second level of magnification higher than the first level.

Embodiment 44 includes the computing device of embodiment 43, wherein the registration information is a first set of registration information, and wherein performing registration of the third microscopy image with the fourth microscopy image results in a first amount of alignment error between the third microscopy image and the fourth microscopy image. In this embodiment, the instructions further cause the processor to: generate, with the neural network and the fifth microscopy image, an additional predicted fluorescence image; determine a second set of registration information that indicates how the additional predicted fluorescence image can be aligned with the fluorescence image of the third microscopy image; and perform registration of the third microscopy image and the fifth microscopy image using the second set of registration information, wherein performing the registration of the third microscopy image with the fifth microscopy image results in a smaller amount of alignment error, relative to the first amount of alignment error, between the third microscopy image and the fifth microscopy image.

Embodiment 45 includes the computing device of embodiment 43 or 44, wherein the second level of magnification is at least ten times the first level of magnification.

Embodiment 46 includes the computing device of any one of embodiments 43-45, wherein the pair of microscopy images is a conjugate array tomography image pair.

Embodiment 47 relates to a computing device, comprising a communication interface configured to receive microscopy images, a processor, and a non-transitory computer-readable medium communicatively coupled to the processor and storing computer-executable instructions that, when executed by the processor, causes the processor to: receive, via the communication interface, a first set of three-dimensional (3D) microscopy images and a second set of 3D microscopy images, wherein the first set of 3D microscopy images are 3D confocal laser scanning microscopy (CLSM) fluorescence images of a plurality of tissue samples each having a plurality of cells, and wherein the second set of 3D microscopy images are 3D transmitted light images of the same plurality of tissue samples, wherein fluorescence labeling is applied to the plurality of cells in the first set of 3D microscopy images, and wherein no fluorescence labeling is included in the second set of 3D microscopy images. The instructions further cause the processor to generate a neural network (or, more generally, a statistical model) configured to convert a first type of image that is a 3D transmitted light image of cells to a second type of image that is a predicted 3D CLSM fluorescence image of the cells, wherein no fluorescence labeling is included in the first type of image, and wherein the instructions cause the processor to generate the neural network by training the neural network based on the first set of 3D microscopy images and the second set of 3D microscopy images. The instructions further cause the processor to receive, after the neural network is generated and trained, an additional 3D microscopy image that is a transmitted light image of an additional tissue sample having a plurality of cells, wherein no fluorescence labeling is included in the additional 3D microscopy image; and to generate, with the neural network and the additional 3D microscopy image, a predicted 3D CLSM fluorescence image that includes predicted fluorescence labeling of the plurality of cells for the additional tissue sample.

Embodiment 48 includes the computing device of embodiment 47, wherein the instructions further cause the processor to determine, using the predicted 3D CLSM fluorescence image, a cell characteristic of the plurality of cells of the additional tissue sample, wherein the cell characteristic is at least one of an average or median cell size, a cell count, cell morphology of at least one of the plurality of cells, a cell cycle phase of at least one of the plurality of cells, or the presence or absence a protein biomarker on a surface of at least one of the plurality of cells.

Embodiment 49 includes the computing device of embodiment 47 or 48, wherein the neural network is a first neural network, wherein the instructions further cause the processor to: receive an indication of which cell in the plurality of tissue samples have a classification of being a diseased cell, and generate a second neural network configured to convert the second type of image that is the predicted 3D CLSM fluorescence image to a predicted classification of whether the predicted fluorescence 3D CLSM image includes a diseased cell, wherein the instructions cause the processor to generate the second neural network by training the second neural network with predicted 3D CLSM fluorescence images generated by the first neural network and with the received indication of which cell in the plurality of tissue samples is a diseased cell. The instructions further cause the processor to generate, with the second neural network and the predicted 3D CLSM fluorescence image of the additional tissue sample, a predicted classification of whether the additional tissue samples include a diseased cell.

Embodiment 50 includes the computing device of any one of embodiments 47-49, wherein the first set of 3D microscopy images includes a subset of 3D fluorescence images for one of the plurality of tissue samples, wherein the subset of 3D fluorescence images correspond to different respective fluorescence channels that each has a different respective emission filter frequency band or a different respective fluorescence marker, wherein the subset of 3D fluorescence images were acquired from the one of the plurality of tissue samples in less than 25 ms per fluorescence channel.

Embodiment 51 includes the computing device of any one of embodiments 47-50, wherein the plurality of cells of the additional tissue sample include or one or more live human-induced pluripotent stem cells (hiPSCs).

Embodiment 52 is a method that includes the steps performed by the processor in any of embodiments 18-51.

Embodiment 53 is a non-transitory computer-readable medium having instructions that, when performed by the processor, causes the processor to perform the steps in any of embodiments 18-51.

Where schematics and/or embodiments described above indicate certain components arranged in certain orientations or positions, the arrangement of components may be modified. While the embodiments have been particularly shown and described, it will be understood that various changes in form and details may be made. Any portion of the apparatus and/or methods described herein may be combined in any combination, except mutually exclusive combinations. The embodiments described herein can include various combinations and/or sub-combinations of the functions, components, and/or statistical models of the different embodiments described.

The invention claimed is:

1. A computing device, comprising:
a communication interface configured to receive microscopy images;
a processor; and
a non-transitory computer-readable medium communicatively coupled to the communication interface and to the processor, and storing computer-executable instructions that, when executed by the processor, causes the processor to:
receive, via the communication interface, a first set of microscopy images and a second set of microscopy images, wherein the first set of microscopy images are fluorescence images of a plurality of tissue samples each having one or more sub-cellular structures or one or more cells, and wherein the second set of microscopy images are electron micrograph (EM) images of the one or more sub-cellular structures or one or more cells of the plurality of tissue samples, wherein no fluorescence labeling is included in the second set of microscopy images;
determine that each of the first set of microscopy images is aligned with one of the second set of microscopy images;
generate, after determining that each of the first set of microscopy images is aligned with one of the second set of microscopy images, a neural network configured to convert a first type of image that is an EM image of any sub-cellular structure or cell to a second type of image that is a predicted fluorescence image of the sub-cellular structure or cell, wherein no fluorescence labeling is included in the first type of image, and wherein the instructions cause the processor to generate the neural network by training the neural network based on the first set of 3D microscopy images and the second set of 3D microscopy images;

receive, after the neural network is generated, a pair of microscopy images that include a third microscopy image and a fourth microscopy image, wherein the third microscopy image is a fluorescence image of one or more cellular structures or one or more cells of an additional tissue sample, and the fourth microscopy image is an EM image of the one or more sub-cellular structures or one or more cells of the additional tissue sample, wherein the third microscopy image and the fourth microscopy image are not aligned with each other;

generate, with the neural network and the EM image of the fourth microscopy image, a predicted fluorescence image that includes predicted fluorescence labeling for the additional tissue sample;

determine registration information that indicates how the predicted fluorescence image can be aligned with the fluorescence image of the third microscopy image; and perform registration of the third microscopy image and the fourth microscopy image using the determined registration information.

2. The computing device of claim 1, wherein the instructions cause the processor to perform the registration by performing at least one of shifting, rotating, or scaling of the third microscopy image relative to the fourth microscopy image based on the registration information.

3. The computing device of claim 2, wherein the instructions cause the processor to overlay the third microscopy image on the fourth microscopy image after the third microscopy image has been shifted, rotated, or scaled based on the registration information.

4. The computing device of claim 1, wherein the instructions cause the processor to determine the registration information by using an intensity-based registration process that performs intensity matching between the predicted fluorescence image and the third microscopy image.

5. The computing device of claim 1, wherein each of the third microscopy image and the fourth microscopy image includes a plurality of pixels, and wherein, before registration is performed, each pixel of the third microscopy image represents a bigger region of the additional tissue sample than does each pixel of the fourth microscopy image, such that the fluorescence image of the third microscopy image is at a lower level of magnification relative to the EM image of the fourth microscopy image.

6. The computing device of claim 5, wherein, before registration is performed, each pixel of the third microscopy image represents a region of the additional tissue sample that is at least 100 times larger than a region of the additional tissue sample represented by each pixel of the fourth microscopy image.

7. The computing device of claim 5, wherein the EM image of the fourth microscopy image was captured by an electron microscope at a first level of magnification of a first region of the additional tissue sample, wherein the instructions further cause the processor to control the electron microscope to acquire a fifth microscopy image of a second region that is a portion of the first region, wherein a location of the second region within the first region is indicated by the registration information, and wherein the fifth microscopy image is an EM image that is at a second level of magnification higher than the first level.

8. The computing device of claim 7, wherein the registration information is a first set of registration information, and wherein performing registration of the third microscopy image with the fourth microscopy image results in a first amount of alignment error between the third microscopy image and the fourth microscopy image, wherein the instructions further cause the processor to:

generate, with the neural network and the fifth microscopy image, an additional predicted fluorescence image;

determine a second set of registration information that indicates how the additional predicted fluorescence image can be aligned with the fluorescence image of the third microscopy image; and perform registration of the third microscopy image and the fifth microscopy image using the second set of registration information, wherein performing the registration of the third microscopy image with the fifth microscopy image results in a smaller amount of alignment error, relative to the first amount of alignment error, between the third microscopy image and the fifth microscopy image.

9. The computing device of claim 8, wherein the second level of magnification is at least ten times the first level of magnification.

10. A non-transitory computer-readable medium having computer-executable instructions that, when executed by a processor, causes the processor to:

receive, via the a communication interface, a first set of microscopy images and a second set of microscopy images, wherein the first set of microscopy images are fluorescence images of a plurality of tissue samples each having one or more sub-cellular structures or one or more cells, and wherein the second set of microscopy images are electron micrograph (EM) images of the one or more sub-cellular structures or one or more cells of the plurality of tissue samples, wherein no fluorescence labeling is included in the second set of microscopy images;

determine that each of the first set of microscopy images is aligned with one of the second set of microscopy images;

generate, after determining that each of the first set of microscopy images is aligned with one of the second set of microscopy images, a neural network configured to convert a first type of image that is an EM image of any sub-cellular structure or cell to a second type of image that is a predicted fluorescence image of the sub-cellular structure or cell, wherein no fluorescence labeling is included in the first type of image, and wherein the instructions cause the processor to generate the neural network by training the neural network based on the first set of 3D microscopy images and the second set of 3D microscopy images;

receive, after the neural network is generated, a pair of microscopy images that include a third microscopy image and a fourth microscopy image, wherein the third microscopy image is a fluorescence image of one or more cellular structures or one or more cells of an additional tissue sample, and the fourth microscopy image is an EM image of the one or more sub-cellular structures or one or more cells of the additional tissue sample, wherein the third microscopy image and the fourth microscopy image are not aligned with each other;

generate, with the neural network and the EM image of the fourth microscopy image, a predicted fluorescence image that includes predicted fluorescence labeling for the additional tissue sample;

determine registration information that indicates how the predicted fluorescence image can be aligned with the fluorescence image of the third microscopy image; and perform registration of the third microscopy image and the fourth microscopy image using the determined registration information.

11. The non-transitory computer-readable medium of claim 10, wherein the instructions, when executed by the processor, cause the processor to perform the registration by performing at least one of shifting, rotating, or scaling of the third microscopy image relative to the fourth microscopy image based on the registration information.

12. The non-transitory computer-readable medium of claim 11, wherein the instructions, when executed by the processor, cause the processor to overlay the third microscopy image on the fourth microscopy image after the third microscopy image has been shifted, rotated, or scaled based on the registration information.

13. The non-transitory computer-readable medium of claim 10, wherein the instructions, when executed by the processor, cause the processor to determine the registration information by using an intensity-based registration process that performs intensity matching between the predicted fluorescence image and the third microscopy image.

14. A computing device, comprising:
a communication interface configured to receive microscopy images;
a processor; and
a non-transitory computer-readable medium communicatively coupled to the processor and storing computer-executable instructions that, when executed by the processor, causes the processor to:
receive, via the communication interface, a first set of three-dimensional (3D) microscopy images and a second set of 3D microscopy images, wherein the first set of 3D microscopy images are 3D confocal laser scanning microscopy (CLSM) fluorescence images of a plurality of tissue samples each having a plurality of cells, and wherein the second set of 3D microscopy images are 3D transmitted light images of the same plurality of tissue samples, wherein fluorescence labeling is applied to the plurality of cells in the first set of 3D microscopy images, and wherein no fluorescence labeling is included in the second set of 3D microscopy images;

generate a neural network configured to convert a first type of image that is a 3D transmitted light image of cells to a second type of image that is a predicted 3D CLSM fluorescence image of the cells, wherein no fluorescence labeling is included in the first type of image, and wherein the instructions cause the processor to generate the neural network by training the neural network based on the first set of 3D microscopy images and the second set of 3D microscopy images;

receive, after the neural network is generated and trained, an additional 3D microscopy image that is a transmitted light image of an additional tissue sample having a plurality of cells, wherein no fluorescence labeling is included in the additional 3D microscopy image; and generate, with the neural network and the additional 3D microscopy image, a predicted 3D CLSM fluorescence image that includes predicted fluorescence labeling of the plurality of cells for the additional tissue sample.

15. The computing device of claim 14, wherein the instructions further cause the processor to determine, using the predicted 3D CLSM fluorescence image, a cell characteristic of the plurality of cells of the additional tissue sample, wherein the cell characteristic is at least one of an average or median cell size, a cell count, cell morphology of at least one of the plurality of cells, a cell cycle phase of at least one of the plurality of cells, or the presence or absence a protein biomarker on a surface of at least one of the plurality of cells.

16. The computing device of claim 15, wherein the neural network is a first neural network, wherein the instructions further cause the processor to:
receive an indication of which cell in the plurality of tissue samples have a classification of being a diseased cell,
generate a second neural network configured to convert the second type of image that is the predicted 3D CLSM fluorescence image to a predicted classification of whether the predicted fluorescence 3D CLSM image includes a diseased cell, wherein the instructions cause the processor to generate the second neural network by training the second neural network with predicted 3D CLSM fluorescence images generated by the first neural network and with the received indication of which cell in the plurality of tissue samples is a diseased cell; and
generate, with the second neural network and the predicted 3D CLSM fluorescence image of the additional tissue sample, a predicted classification of whether the additional tissue samples include a diseased cell.

* * * * *

UNITED STATES PATENT AND TRADEMARK OFFICE
CERTIFICATE OF CORRECTION

PATENT NO. : 11,614,610 B2
APPLICATION NO. : 17/148192
DATED : March 28, 2023
INVENTOR(S) : Gregory Johnson et al.

It is certified that error appears in the above-identified patent and that said Letters Patent is hereby corrected as shown below:

In the Specification

In the statement regarding federally-sponsored research and development, Column 1, Lines 25-28:
"This invention was supported by grants from the National Institutes of Health, NIH/NINDS (RO1NS092474) and NIH/NIMH (ROIMH104227). As such, the government may have certain rights in the invention."

Should be replaced by:
"This invention was made with government support under NS092474 and MH104227 awarded by the National Institutes of Health. The government has certain rights in the invention."

Signed and Sealed this
Twenty-third Day of April, 2024

Katherine Kelly Vidal
Director of the United States Patent and Trademark Office